US010590421B2

(12) United States Patent
van Roon-Mom et al.

(10) Patent No.: US 10,590,421 B2
(45) Date of Patent: Mar. 17, 2020

(54) ANTISENSE OLIGONUCLEOTIDE DIRECTED REMOVAL OF PROTEOLYTIC CLEAVAGE SITES, THE HCHWA-D MUTATION, AND TRINUCLEOTIDE REPEAT EXPANSIONS

(71) Applicant: Academisch Ziekenhuis Leiden H.O.D.N. LUMC, Leiden (NL)

(72) Inventors: Wilhelmina M. C. van Roon-Mom, Beverwijk (NL); Melvin Maurice Evers, Utrecht (NL); Barry Antonius Pepers, Leiden (NL); Annemieke Aartsma-Rus, Hoofddorp (NL); Garrit-Jan Boudewijn Van Ommen, Amsterdam (NL)

(73) Assignee: Academisch Ziekenhuis Leiden H.O.D.N. LUMC, Leiden (NL)

( * ) Notice: Subject to any disclaimer, the term of this patent is extended or adjusted under 35 U.S.C. 154(b) by 72 days.

(21) Appl. No.: 15/494,052

(22) Filed: Apr. 21, 2017

(65) Prior Publication Data
US 2017/0226521 A1  Aug. 10, 2017

Related U.S. Application Data

(60) Division of application No. 14/047,876, filed on Oct. 7, 2013, now abandoned, which is a continuation-in-part of application No. 13/814,203, filed as application No. PCT/NL2011/050549 on Aug. 4, 2011, now Pat. No. 9,611,471.

(60) Provisional application No. 61/370,855, filed on Aug. 5, 2010.

(30) Foreign Application Priority Data

Aug. 5, 2010 (EP) ..................................... 10172076

(51) Int. Cl.
C12N 15/11 (2006.01)
C12N 15/113 (2010.01)

(52) U.S. Cl.
CPC ........ *C12N 15/1137* (2013.01); *C12N 15/111* (2013.01); *C12N 15/113* (2013.01); *C12Y 304/19012* (2013.01); *C12N 2310/11* (2013.01); *C12N 2310/315* (2013.01); *C12N 2310/321* (2013.01); *C12N 2310/346* (2013.01); *C12N 2320/33* (2013.01)

(58) Field of Classification Search
CPC ..... C12N 15/11; C12N 15/111; C12N 15/113; C12N 15/1137; C12N 2310/11; C12N 2310/113; C12N 2310/31; C12N 2310/315; C12N 2310/346; C12N 2320/33
See application file for complete search history.

(56) References Cited

U.S. PATENT DOCUMENTS

| | | | |
|---|---|---|---|
| 7,973,015 B2 | 7/2011 | Van et al. | |
| 8,361,979 B2* | 1/2013 | Aartsma-Rus | A61K 48/0016 514/44 A |
| 9,243,245 B2 | 1/2016 | De et al. | |
| 9,611,471 B2 | 4/2017 | Van et al. | |
| 9,926,557 B2 | 3/2018 | De et al. | |
| 2002/0049173 A1 | 4/2002 | Bennett et al. | |
| 2003/0235845 A1 | 12/2003 | van Ommen et al. | |
| 2005/0118625 A1* | 6/2005 | Mounts | B82Y 30/00 435/6.14 |
| 2006/0099616 A1 | 5/2006 | van Ommen et al. | |
| 2006/0147952 A1 | 7/2006 | van Ommen et al. | |
| 2006/0154370 A1 | 7/2006 | Chen | |
| 2006/0172962 A1 | 8/2006 | Vickers et al. | |
| 2007/0299027 A1 | 12/2007 | Hung et al. | |
| 2008/0039418 A1 | 2/2008 | Freier | |
| 2008/0200409 A1* | 8/2008 | Wilson | C12N 15/113 514/44 A |
| 2008/0209581 A1 | 8/2008 | van Ommen et al. | |
| 2009/0011004 A1 | 1/2009 | Lutz et al. | |
| 2009/0076246 A1 | 3/2009 | van Deutekom | |
| 2009/0228998 A1 | 9/2009 | van Ommen et al. | |
| 2010/0069472 A1 | 3/2010 | Hung et al. | |
| 2010/0184833 A1 | 7/2010 | De Kimpe et al. | |
| 2011/0166197 A1* | 7/2011 | Darling | C07K 14/4711 514/44 A |
| 2012/0270930 A1 | 10/2012 | Van Der Maarel et al. | |
| 2013/0198877 A1 | 8/2013 | van Roon-Mom et al. | |

(Continued)

FOREIGN PATENT DOCUMENTS

| | | |
|---|---|---|
| WO | 0224906 A1 | 3/2002 |
| WO | 2004083432 A1 | 9/2004 |
| WO | 2004083446 A2 | 9/2004 |

(Continued)

OTHER PUBLICATIONS

Li et al, Mol. Neurodegeneration 9(28): pp. 1-15, 2014.*

(Continued)

*Primary Examiner* — Kevin K Hill
(74) *Attorney, Agent, or Firm* — TraskBritt

(57) ABSTRACT

Described are methods for removing a proteolytic cleavage site, the HCHWA-D mutation or the amino acids encoded by a trinucleotide repeat expansion from a protein comprising providing a cell that expresses pre-mRNA encoding the protein with an anti-sense oligonucleotide that induces skipping of the exonic sequence that comprises the proteolytic cleavage site, HCHWA-D mutation or trinucleotide repeat expansion, respectively, the method further comprising allowing translation of mRNA produced from the pre-mRNA.

7 Claims, 21 Drawing Sheets
Specification includes a Sequence Listing.

(56) References Cited

U.S. PATENT DOCUMENTS

2014/0039037 A1* 2/2014 Van Roon-Mom .......................... C12N 15/111
514/44 A

FOREIGN PATENT DOCUMENTS

| WO | 2007051045 A2 | 5/2007 |
|---|---|---|
| WO | 2007089584 A2 | 8/2007 |
| WO | 2007089611 A2 | 8/2007 |
| WO | 2007123402 A2 | 11/2007 |
| WO | 2008/018795 A1 | 2/2008 |
| WO | WO 09/105572 * | 8/2009 |
| WO | 2012018257 A1 | 2/2012 |

OTHER PUBLICATIONS

Donev et al, Mol. Psychiatry 12:681-690, 2007.*
Ichikawa et al., The genomic structure and expression of MJD, the Machado-Joseph disease gene, 2001, Journal of Human Genetics 46, pp. 413-422.
Mulders et al., Triplet-repeat oligonucleotide-mediated reversal of RNA toxicity in myotonic dystrophy, Aug. 10, 2009, PNAS 106 (33), pp. 13915-13920.
Nijhawan et al., Apoptosis in neural development and disease, Mar. 2000, Annual Review of Neuroscience, issue 23, pp. 73-87.
Sumantran et al., Overexpression of Bcl-xs Sensitizes MCF7 Cells to Chemotherapy-induced Apoptosis1, 1995, Cancer Resource (55) pp. 2507-2510.
Gregory et al., Differential Regulation of Human Eosinophil IL-3, IL-5, and GM-CSF Receptor a- Chain Expression by Cytokines: IL-3, IL-5, and GM-CSF Down-Regulate IL-5 Receptor a- Expression with Loss of IL-5 Responsiveness, but Up-Regulate IL-3 Receptor a- Expression, Journal Immunology 170, issue 11, pp. 5359-5366.
Karras et al., Peptide Nucleic Acids Are Potent Modulators of Endogenous Pre-mRNA Splicing of the Murine Interleukin-5 Receptor-Alpha Chain, Jun. 5, 2001, Biochemistry 40 (26), pp. 7853-7859.
Kurreck et al., Antisense technologies, Improvement through novel chemical modifications, Apr. 2003, Europe Journal Biochemistry, vol. 270 (8), pp. 1628-1644.
Alessia David et al., Repair of Aberrant Splicing in Growth Hormone Receptor by Antisense Oligonucleotides Targeting the Splice Sites of a Pseudoexon; J Clin Endocrinol Metab, Jul. 2010, 95 (7):3542-3546.
EP Office Action dated May 11, 2017.
Boise et al., bcl-x, A bcl-2-related gene that functions as a dominant regulator of apoptotic cell death, Cell, 74: 4, 597-608, 1993.
Chelly et al, Dystrophin gene transcribed from different promoters in neuronal and glial cells, Nature 344(6261):64-65, 1990; abstract only.
Database Biosis Online, Biosciences Information Service, Philadelphia, PA, Oligonucleotide Therapeutics, 2009.
ExPASy Peptide Cutter, IL-5R Sequence analysis created Sep. 19, 2016.
ExPASy Peptide Cutter, Bcl-x sequence analysis created Sep. 19, 2016.
Gafni et al, Inhibition of Calpain Cleavage of Huntingtin Reduces Toxicity, J. Biol. Chem. 279(19): 20211-20220, Feb. 4, 2004, The American Society for Biochemistry and Molecular Biology, Inc., printed in U.S.A.
GenBank NM_002111.7, Homosapiens huntingtin (HTT), mRNA, Mar. 2015.
Graham et al, Cleavage at the Caspase-6 Site Is Required for Neuronal Dysfunction and Degeneration Due to Mutant Huntingtin, Cell, 125:1179-1191, Jun. 16, 2006, Elsevier Inc.
Kurreck et al., Jens, Antisense technologies, Improvement through novel chemical modificaitons, Eur., J. Biochem., 2003.

McClorey et al, Antisense oligonucleotide-induced exon skipping restores dystrophin expression in vitro in a canine model of DMD, Gene Therapy 13:1373-1381, May 25, 2006, Nature Publishing Group.
Mehler, Mark F., Brain dystrophin, neurogenetics and metal retardation, Brain Research Reviews, Apr. 2000, pp. 277-307, vol. 32, No. 1.
Mineur et al., Newly identified biologically active and proteolysis-resistant VEGF-A isoform VEGF111 is induced by genotoxic agents, Journal of Cell Biology, Dec. 17, 2007, pp. 1261-1273, vol. 179, No. 6.
Owens et al., Current Topics in Micrbiol & Immunol. 336: 105-120, in Toll-like Receptors: Roles in infection and Neuropathy, T. Kielian ed, Springer-Verlag, 2009.
Prosper et al., Peptide Cutter, IL-5R Sequence analysis created Sep. 21, 2016.
Spitali et al., Exon Skipping-Mediated Dystrophin Reading Frame Restoration for Small Mutations, Human Mutation, Nov. 2009, pp. 1527-1534, vol. 30, No. 11.
Wilton et al., Antisense Oligonucleotide-induced Exon Skipping Across the Human Dystrophin Gene Transcript, Molecular Therapy, Jul. 2007, pp. 1288-1296, vol. 15, No. 7.
Gregory et al., Differential Regulation of Human Eosinophil IL-3, IL-5, and GM-CSF Receptor a- Chain Expression by Cytokines: IL-3, IL-5, and GM-CSF Down-Regulate IL-5 Receptor a- Expression with Loss of IL-5 Responsiveness, but Up-Regulate IL-3 Receptor a- Expression, Journal Immunology 170, issue 11, 2013, pp. 5359-5366.
Karras et al., Deletion of Individual Exons and Induction of Soluble Murine Interleukin-5 Receptor-alpha Chain Expression through Antisense Oligonucleotide-Mediated Redirection of Pre-mRNA Splicing, Molecular Pharmacology, 2000, pp. 380-387, vol. 58.
Menon et al., Expansion of amino acid homo-sequences in proteins: Insights into the role of amino acid homo-polymers and of the protein context in aggregation, Cell. Mol. Life Sci., Jun. 22, 2006, 63(14);1677-1685.
Tiscornia et al., Myotonic Dystrophy: The Role of the CUG Triplet Repeats in Splicing of a Novel DMPK Exon and Altered Cytoplasmic DMPK mRNA Isoform Ratios, Molecular Cell, Jun. 2000, pp. 959-967, vol. 5.
Hu et al., Inhibiting Expression of Mutant Huntingtin and Ataxin-3 by Targeting Expanded CAG Repeat RNAs, Nature Biotechnol., May 2009, pp. 478-484, vol. 27, No. 5.
Makeyev et al, The MicroRNA miR-124 Promotes Neuronal Differentiation by Triggering Brain-Specific Alternative Pre-mRNA Splicing, Molecular Cell 27: 435-448, Aug. 3, 2007.
Koenig et al, Detailed Analysis of the Repeat Domain of Dystrophin Reveals Four Potential Hinge Segments That May Confer Flexibility, J. Biol. Chem. 265(8): 4560-4566, Mar. 15, 1990.
Badorff et al, Enteroviral Protease 2A Directly Cleaves Dystrophin and Is Inhibited by a Dystrophin-based Substrate Analogue, J. Biol. Chem. 271(15): 11191-11197, Apr. 14, 2000.
Aartsma-Rus et al. "Guidelines for Antisense Oligonucleotide Design and Insight Into Splice-modulating Mechanisms" Article, vol. 17, Issue 3, p. 548-553, Mar. 1, 2009 (Abstract).
Egholm et al. "PNA hybridizes to complementary oligonucleotides obeying the Watson-Crick Hydrogen-bonding rules", letter Published: Oct. 7, 1993, Nature 365, 566-568 (1993) (Abstract).
Garcia-Calvo et al. "Inhibition of Human Caspases by Peptide-based and Macromolecular Inhibitors", The Journal of Biological Chemistry, vol. 273, No. 49, Issue of Dec. 4, pp. 32608-32613, 1998.
Govindaraju et al. "Backbone-extended pyrrolidine peptide nucleic acids (bepPNA): design, synthesis and DNA/RNA binding studies" Issue 4, 2005, Chemical Communications (Abstract).
Nielsen et al."Sequence-selective recongnition of DNA by strand displacement with a thymine-substituted polyamide" Report, Science Dec. 6, 1991: vol. 254, Issue 5037, pp. 1487-1500.
Real et al. "Gamma-secretase inhibitors reverse glucocorticoid resistance in T-ALL"; Nat Med. Jan. 2009; 15(1): 50-58 (Abstract).
Wellington et al. "Inhibiting Caspase Cleavage of Huntingtin Reduces Toxicity and Aggregate Formation in Heuronal and Nonneuronal

(56) References Cited

OTHER PUBLICATIONS

Cells", The Journal of Biological Chemistry, vol. 275, No. 26, Issue of Jun. 30, pp. 19831-19838, 2000.
Coria et al. Beta-protein deposition: a pathogenetic link between Alzheimer's disease and cerebral amyloid angiopathies. Brain Res. Oct. 25, 1988;463(1): 187-91. (Abstract).

* cited by examiner 421 siveliaygg sscspvlsrk qkqkvllgee ealeddsesr sdvsssalta svkdeisgei
481 aassgvstpg saghdiiteq prsghtlqad svdlascdlt ssatdgdeed ilshssq
541                di nd                          ivldgtdn gylglqlgmp
601 qdedeaatgi lpdeaseafr nsamalqqah llknmshcrq psdssvdkfv lrdeatepgd

FIG. 4

APP751

15: GLTNIKTEEISEVKMDAEFRHDSGYEVHHQKL
16: VFFAEDVGSNKGAIIGLMVGGVVIATVIVITLVMLKKKQYTSIHHGVVE
17: VDAAVTPEERHLSKMQQNGYENPTYKFFEQMQN

APP770

16: SGLTNIKTEEISEVKMDAEFRHDSGYEVHHQKL
17: VFFAEDVGSNKGAIIGLMVGGVVIATVIVITLVMLKKKQYTSIHHGVVE
18: VDAAVTPEERHLSKMQQNGYENPTYKFFEQMQN

APPmouse

14: SGLTNIKTEEISEVKMDAEFGHDSGFEVRHQKL
15: VFFAEDVGSNKGAIIGLMVGGVVIATVIVITLVMLKKKQYTSIHHGVVE
16: VDAAVTPEERHLSKMQQNGYENPTYKFFEQMQN

FIG. 20

ANTISENSE OLIGONUCLEOTIDE DIRECTED REMOVAL OF PROTEOLYTIC CLEAVAGE SITES, THE HCHWA-D MUTATION, AND TRINUCLEOTIDE REPEAT EXPANSIONS

CROSS-REFERENCE TO RELATED APPLICATIONS

This application is a divisional of U.S. patent application Ser. No. 14/047,876, filed Oct. 7, 2013, which is a continuation-in-part of U.S. patent application Ser. No. 13/814,203, filed Apr. 12, 2013, now U.S. Pat. No. 9,611,471, issued Apr. 4, 2017, which application is a national phase entry under 35 U.S.C. § 371 of International Patent Application PCT/NL2011/050549, filed Aug. 4, 2011, designating the United States of America and published in English as International Patent Publication WO 2012/018257 A1 on Feb. 9, 2012, which claims the benefit under Article 8 of the Patent Cooperation Treaty and under 35 U.S.C. § 119(e) to U.S. Provisional Patent Application Ser. No. 61/370,855, filed Aug. 5, 2010, and to European Patent Application Serial No. 10172076.1, filed Aug. 5, 2010, the entire disclosure of each of which is hereby incorporated herein by this reference.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

TECHNICAL FIELD

The disclosure relates to the field of biotechnology and genetic and acquired diseases. The disclosure, in particular, relates to the alteration of mRNA processing of specific pre-mRNA to remove a proteolytic cleavage site, the HCHWA-D mutation, or the amino acids encoded by a trinucleotide repeat expansion from a protein encoded by the pre-mRNA.

BACKGROUND

Proteolytic processing is a major form of post-translational modification that occurs when a protease cleaves one or more bonds in a target protein to modify its activity. This processing may lead to activation, inhibition, alteration or destruction of the protein's activity. Many cellular processes are controlled by proteolytic processing. The attacking protease may remove a peptide segment from either end of the target protein, but it may also cleave internal bonds in the protein that lead to major changes in the structure and function of the protein.

Proteolytic processing is a highly specific process. The mechanism of proteolytic processing varies according to the protein being processed, location of the protein, and the protease.

Proteolytic processing can have various functions. For instance, proteolysis of precursor proteins regulates many cellular processes including gene expression, embryogenesis, the cell cycle, programmed cell death, intracellular protein targeting and endocrine/neural functions. In all of these processes, proteolytic cleavage of precursor proteins is necessary. The proteolysis is often done by serine proteases in the secretory pathways. These proteases are calcium-dependent serine endoproteases and are related to yeast and subtilisin proteases and, therefore, called Subtilisin-like Pro-protein Convertases (SPCs) or PCs. Seven members of this family have been identified & characterized and each have conserved signal peptides, pro-regions, catalytic and P-domains but differ in their C-terminal domains in mammals.

Autocatalytic cleavage of an N-terminal propeptide activates these proteases, which is required for folding, and activity also causes the release of prodomain. Other examples of function associated with proteolytic processing are the blood clotting cascades, the metaloendopeptidases, the secretases and the caspases. Yet other examples are the viral proteases that specifically process viral polyproteins.

The art describes various strategies to inhibit the various proteases. For instance, gamma-secretase inhibitors are presently being developed for the treatment of T cell acute lymphoblastic leukemia (*Nature Medicine* 2009:15:50-58). Caspase inhibitors are being developed for a variety of different applications (*The Journal of Biological Chemistry* 1998, 273:32608-32613), for instance, in the treatment of sepsis (*Nature Immunology* 2000, 1:496-501).

A problem with the use of protease inhibitors is that these proteins typically have a range of targets in the human body and, associated therewith, a range of effects. Inhibiting a protease in the human body through the action of a protease inhibitor thus, not only inhibits the desired effect, but typically also has a range of other effects that may or may not affect the utility of the protease inhibitor for the indicated disease. Another problem associated with protease inhibitors is that it is not always easy to produce an inhibitor that is sufficiently specific for the target protease and, therefore, may also inhibit other proteases.

DISCLOSURE

Provided is an alternative approach to interfere with the proteolytic processing of target proteins. Instead of designing inhibitors to the proteases, the target protein itself is modified. In the art, it is known to modify a protease cleavage site in a target protein. This is typically done by introducing point mutations into the coding region of a protein. These mutations typically break up the recognition sequence of the protease. These types of modification are usually introduced into a cDNA copy of the gene and this altered copy is inserted into the DNA of cells by recombinant DNA technology. Although this can be done in the laboratory, it is difficult to implement such strategies in the clinic, if only because gene therapy applications that rely on the introduction of a complete gene are, at present, not very efficient, and the original gene associated with the problem is not removed.

Provided is a method for removing a proteolytic cleavage site from a protein comprising providing a cell that expresses a pre-mRNA encoding the protein with an antisense oligonucleotide (AON) that induces skipping of the exon sequence that encodes the proteolytic cleavage site, or partially removing the proteolytic cleavage site, rendering it inactive, the method further comprising allowing translation of mRNA produced from the pre-mRNA.

Also provided for are methods for removing exons containing trinucleotide repeat expansions. Such expansions can lead to a number of conditions including fragile X syndrome, fragile XE syndrome, Friedreich ataxia, myotonic dystrophy, spinocerebellar ataxia (SCA) type 8, spinobulbar muscular atrophy (SBMA, also known as Kennedy's disease), Huntington disease (HD), dentatorubral-pallidoluysian atrophy (DRPLA), and the SCA types 1, 2, 3, 6, 7, 12, and 17 (see Tables 1a and 1b). Preferably, the trinucleotide repeat expansion is a CAG repeat expansion, i.e., a polyglutamine expansion.

Polyglutamine (polyQ) diseases are a group of autosomal dominant neurodegenerative disorders caused by CAG triplet repeat expansions in protein coding regions of the genome. This CAG repeat is translated into an extended glutamine stretch in the mutant protein, which causes a gain of toxic function inducing neuronal loss in various regions throughout the brain. A hallmark of all polyQ disorders is the formation of large insoluble protein aggregates containing the expanded disease protein. Exemplary polyQ disorders are listed in Table 1a.

The most prevalent polyQ disorder, Huntington's disease (HD), is caused by a CAG repeat expansion in the first exon of the HTT gene on chromosome 4p16. The expanded CAG transcript is translated into a mutant huntingtin (htt) protein with an expanded polyQ tract at the N-terminus. Carriers of 39 or more CAG repeats will develop HD, whereas people with 35 to 38 repeats show reduced penetrance.

Spinocerebellar ataxia type 3 (SCA3), also known as Machado-Joseph disease (MJD), is another polyglutamine (polyQ) disorder. In SCA3, the CAG repeat is located in the penultimate exon of the ATXN3 gene on chromosome 14q32.1. Healthy individuals have a CAG repeat ranging from 10 to 51, whereas SCA3 patients have an expansion of 55 repeats or more. Transgenic mice expressing either a mutant ataxin-3 cDNA fragment or the mutated full-length genomic sequence showed a clear ataxic phenotype with a more severe phenotype in the animals carrying larger repeats, demonstrating a relationship between CAG repeat length and disease severity. The ATXN3 gene codes for the ataxin-3 protein of 45 kDa, which acts as an isopeptidase and is thought to be involved in deubiquitination and proteasomal protein degradation 8-10. The ataxin-3 protein contains an N-terminal Josephin domain that displays ubiquitin protease activity and a C-terminal tail with two or three ubiquitin interacting motifs (UIMs), depending on the isoform.

Successful allele-specific reduction of the mutant ataxin-3 transcript was shown using lentiviral shRNAs directed against a single nucleotide polymorphism (SNP) in the ATXN3 gene in vitro and in vivo. However, this approach is limited to SCA3 patients carrying a heterozygous SNP in the ATXN3 gene. The disclosure provides a novel way to reduce toxicity of the ataxin-3 protein through protein modification. Using AONs, it is possible to mask sequences in the pre-mRNA from the splicing machinery resulting in exclusion of the targeted exon, either partially or in its entirety. If the reading frame remains intact, subsequent translation yields an internally truncated protein. This has the major advantage that a polyQ-containing part of the protein is removed, while maintaining global ataxin-3 protein levels. This strategy can be used to remove the trinucleotide repeats in other proteins as well.

Attempts at inhibiting the pathogenic effect of trinucleotide repeats have also focused on steric block antisense oligonucleotides. For example, in DM1, the trinucleotide repeat in the RNA sequesters the protein MBNL1 resulting in a loss-of-function phenotype for MBNL1. Small molecule compounds, as well as antisense oligonucleotides, have been used to bind the trinucleotide repeat in an attempt to inhibit the binding of MBNL1. The present disclosure relates to oligonucleotides and methods for skipping an exon, either partially or in its entirety. This is a completely different mechanism than that used by steric blocking antisense oligonucleotides.

Methods are provided for treating trinucleotide repeat expansion disorders and for removing trinucleotide repeats from pre-mRNA, both in vivo and in vitro. In some embodiments, methods are provided for treating a disease in an individual that is associated with a mutant gene that comprises a trinucleotide repeat expansion when compared to the gene of a normal individual. Such diseases are provided in, e.g., Tables 1a and 1b. The methods comprise providing to an individual in need thereof a therapeutically effective amount of one or more anti-sense oligonucleotide that induces skipping of one or more exonic sequences that comprise the amino acids encoded by a trinucleotide repeat expansion. The treatment may comprise administering the anti-sense oligonucleotides or administering cells comprising the oligonucleotides.

A trinucleotide repeat as used herein is at least three, preferably at least four repeating trinucleotides. A trinucleotide repeat expansion refers to an increase in number of trinucleotide repeats over the normal individual. The increase in repeats necessary to cause pathology differs depending on the protein (see, e.g., Tables 1a and 1b).

The methods and compositions described herein are useful for removing trinucleotide repeat expansions. The removal of the expansion is the result of skipping the exonic sequence that comprises the trinucleotide repeat expansion. The skipping of the exonic sequence may be achieved by the removal of the exon in its entirety. Alternatively, the exon may be partially skipped. This can occur, e.g., when an alternative splice site or a cryptic splice site is utilized. For example, the examples in the disclosure describe the partial skipping of exon 9 from ATXN3.

Regardless of whether the skipped exonic sequences represent an entire or partial exon, the trinucleotide repeat expansion is skipped in its entirety, i.e., the skipped exonic sequences fully comprise the trinucleotide repeat expansion. When a wild-type allele is present that lacks a trinucleotide repeat expansion, exon-skipping will result in the removal of the wild-type trinucleotide repeat. Throughout the disclosure, "removal of a trinucleotide repeat expansion" is used to refer to the skipping of the exonic sequences that contain an entire trinucleotide repeat (when in the wild-type form) or an entire trinucleotide repeat expansion (when in the mutant form).

Preferably, the exon containing a trinucleotide repeat expansion does not contain a proteolytic cleavage site. For the ATXN3 gene, it is preferred that for the in-frame removal of trinucleotide repeats, exons 9 and 10 are skipped partially or in their entirety. The disclosure further provides a set of oligonucleotides comprising a first oligonucleotide that induces skipping of exonic sequences of exon 9 and a second oligonucleotide that induces skipping of exonic sequences of exon 10.

For the ATN1 gene, the CAG repeat is located in exon 5. For in-frame removal, sequences from exon 6 should also be removed. It is preferred that an exonic sequence from exon 5 and an exonic sequence from exon 6 are skipped.

For the ATXN1 gene, it is preferred that an exonic sequence from exon 8 is skipped.

For the CACNA1A gene, it is preferred that an exonic sequence from exon 47 is skipped.

For the ATXN7 gene, it is preferred that an exonic sequence from exon 3 is skipped.

For the TBP gene, the CAG repeat is located in exon 3 and for in-frame removal, sequences from exon 4 should also be skipped. It is preferred that an exonic sequence from exon 3 and an exonic sequence from exon 4 are skipped.

Also provided are methods and compounds useful in the treatment of Alzheimer's disease (AD). AD is characterized by the deposition of amyloid in extracellular plaques and intracellular neurofibrillary tangles in the brain. The amyloid plaques are mainly composed of amyloid peptides that originate from the Amyloid Precursor Protein (APP) by a series of proteolytic cleavage steps. Several alternative splicing forms of APP have been identified, of which the most abundant are proteins of 695, 751 and 770 amino acids in length. These are herein referred to as APP695, APP751, and APP770.

The beta peptides are produced from APP through the sequential action of two proteolytic enzymes termed beta and gamma-secretase. Beta-secretase cleaves first in the extracellular domain of APP just outside of the trans-membrane domain to produce a C-terminal fragment of APP containing the trans-membrane domain and cytoplasmic domain. The cytoplasmic domain is the substrate for gamma-secretase, which cleaves at several adjacent positions within the trans-membrane domain to produce the A-beta peptides and the cytoplasmic fragment. Various proteolytic cleavages mediated by gamma-secretase result in A-beta peptides of different chain length. A-beta 42 is regarded to be the more pathogenic amyloid peptide because of its strong tendency to form neurotoxic aggregates.

In preferred embodiments, methods are provided for removing a proteolytic cleavage site from APP comprising providing a cell that expresses pre-mRNA encoding APP with an anti-sense oligonucleotide that induces skipping of the exonic sequence that encodes the proteolytic cleavage site, the method further comprising allowing translation of mRNA produced from the pre-mRNA. Preferably, an exonic sequence corresponding to exon 16 of APP751 is skipped. Preferred oligonucleotides are provided in Table 3.

Further provided is an oligonucleotide of 14-40 nucleotides comprising an AON sequence or a derivative thereof depicted in Table 2 or Table 3 for skipping an exon in a pre-mRNA produced by the corresponding gene of Table 2 or Table 3.

The disclosure further provides an oligonucleotide of 14-40 nucleotides specific for the target sequence depicted in Table 3 for skipping an exon in a pre-mRNA produced by the corresponding gene identified in Table 3.

Preferably, methods for treating Alzheimer's disease that comprise administering to an individual in need thereof an effective amount of an anti-sense oligonucleotide that induces skipping of an APP exonic sequence that encodes a proteolytic cleavage site as described herein.

Mutations in APP are also involved in hereditary cerebral hemorrhage with amyloidosis, Dutch type (HCHWA-D). HCHWA-D is an autosomal dominant condition caused by a single base pair mutation in the APP gene that leads to a single amino acid substitution in APP (glutamine instead of glutamic acid) (Levy et al., *Science* 1990 248:1124-6, corresponding to Abeta E22Q (see FIG. 19).

In HCHWA-D, amyloid protein progressively deposits in cerebral blood vessel walls with subsequent degenerative vascular changes that usually result in spontaneous cerebral hemorrhage, ischemic lesions, and progressive dementia. The principal clinical characteristic is recurring cerebral hemorrhages, sometimes preceded by migrainous headaches or mental changes.

Methods are provided for treating individuals afflicted with HCHWA-D, comprising administering to an individual in need thereof a therapeutically effective amount of one or more anti-sense oligonucleotides that induce skipping of the exonic sequences containing the HCHWA-D mutation. The HCHWA-D mutation is located in exon 16 of the APP751 transcripts isoform (see FIGS. 19 and 20) and exon 17 of the APP770 transcript isoform (FIG. 20). Preferably, the oligonucleotides that induce skipping of the HCHWA-D mutation induce the skipping of exonic sequences corresponding to exon 16 of APP751. As is clear to a skilled person, the exonic sequences corresponding to exon 16 of APP751 correspond to exon 17 in APP770. A skilled person can determine the location of the E22Q mutation in other APP transcripts. The skipping of the exonic sequences may remove an exon in its entirety. Alternatively, an exon may be removed partially, for example, if a cryptic splice site is utilized as a splice acceptor or donor.

While not wishing to be bound by theory, removal of the exon containing the HCHWA-D mutation is thought to reduce the formation or slow the progression of amyloid protein deposits in cerebral blood vessel walls.

The disclosure also provides oligonucleotides that induce the skipping of the exonic sequences comprising the HCHWA-D mutation. Such oligonucleotides are useful for removing the HCHWA-D mutation from the APP mRNA and, in particular, in the treatment of HCHWA-D. Oligonucleotides corresponding to hAPPEx16_1-hAPPEx16_6 of Table 3 are preferred.

The methods hereof are particularly useful for removing proteolytic cleavage sites, the HCHWA-D mutation, and the amino acids encoded by trinucleotide repeat expansions from proteins. It does not require removal or modification of the gene itself, but rather, prevents the incorporation of the genetic code for the proteolytic cleavage site, HCHWA-D mutation, or trinucleotide repeat expansions into the coding region of the protein in the mature mRNA. In this way, the process is reversible. The oligonucleotide has a finite life span in the cell and, therefore, has a finite effect on the removal. Another advantage is that the removal is not absolute. Not all pre-mRNA coding for the target protein that is generated by the cell is typically targeted. It is possible to achieve high levels of skipping. The skipping efficiency depends, for instance, on the particular target, the particular exon sequence to be skipped, the particular AON design, and/or the amount of AON used. Skipping percentages are typically expressed as the ratio of mRNA that does not have the coding part of the proteolytic cleavage site (skipped mRNA) versus the sum of skipped mRNA and unmodified mRNA coding for the unmodified target protein (unmodified mRNA). The possibility of tailoring the percentage of skipping is advantageous; for instance, when the unmodified protein is associated with a toxic phenotype but also has a positive function to perform that is not performed (as well) by the modified protein. By removing the proteolytic cleavage site, HCHWA-D mutation, or the amino acids encoded by trinucleotide repeat expansions only from a fraction of the protein formed, it is possible to reduce the toxic property, while leaving the positive or desired function of the unmodified protein at least partially intact.

The method provided modulates the splicing of a pre-mRNA into an mRNA, such that an exonic sequence that codes for a proteolytic cleavage site, HCHWA-D mutation, or the amino acids encoded by a trinucleotide repeat expansion that is present in the exons encoded by the pre-mRNA is not included in the mature mRNA produced from the pre-mRNA. Protein that is subsequently translated from this mRNA does not contain the proteolytic cleavage site, HCHWA-D mutation, trinucleotide repeat expansion. The method, thus, does not actually remove a proteolytic cleavage site, HCHWA-D mutation, or the amino acids encoded by a trinucleotide repeat expansion from a protein that has already been formed. Rather, it promotes the production of a novel protein that does not contain the proteolytic cleavage site, HCHWA-D mutation, or the amino acids encoded by a trinucleotide repeat expansion. However, when looking at a cell as an entity wherein protein synthesis and degradation are at equilibrium, the result of a method hereof can be seen as removing a proteolytic cleavage site, HCHWA-D mutation, or the amino acids encoded by a trinucleotide repeat expansion from a protein. Unmodified target protein is gradually replaced by target protein that does not contain the proteolytic cleavage site, HCHWA-D mutation, or the amino acids encoded by a trinucleotide repeat expansion. Thus, provided is a method for producing a cell that contains a modified protein that lacks a proteolytic cleavage site, HCHWA-D mutation, or the amino acids encoded by a trinucleotide repeat expansion, when compared to the unmodified protein encoded in the genome, the method comprising providing a cell that expresses pre-mRNA encoding the protein with an AON that induces skipping of the exon sequence or part of the exon sequence that encodes the proteolytic cleavage site, HCHWA-D mutation, or the amino acids encoded by a trinucleotide repeat expansion, the method further comprising allowing translation of mRNA produced from the pre-mRNA in the cell. The novel mRNA from which the coding sequence for the proteolytic cleavage site, HCHWA-D mutation, or trinucleotide repeat expansion is removed is a shortened or smaller coding sequence that codes for a shorter or smaller version of the unmodified protein. Often, the modified protein is an internally deleted version of the unmodified protein, wherein the internal deletion at least breaks up and, preferably, deletes the proteolytic cleavage site, HCHWA-D mutation, or the amino acids encoded by a trinucleotide expansion. In the case of the trinucleotide expansion, the internally deleted protein lacks all the amino acids encoded by the expansion.

Antisense-mediated modulation of splicing (also referred to as exon-skipping) is one of the fields where AONs have been able to live up to their expectations. In this approach, AONs are implemented to facilitate cryptic splicing, to change levels of alternatively spliced genes, or, in case of Duchenne muscular dystrophy (DMD), to skip an exon in order to restore a disrupted reading frame. The latter allows the generation of internally deleted, but largely functional, dystrophin proteins and would convert a severe DMD into a milder Becker muscular dystrophy phenotype. In fact, exon skipping is currently one of the most promising therapeutic tools for DMD, and a successful first-in-man trial has recently been completed. The antisense-mediated modulation of splicing has been diversified since its first introduction and now many different kinds of manipulations are possible. Apart from classical exon skipping where typically an entire exon is skipped from the mature mRNA, it is, for instance, possible to skip a part of an exon. Exon inclusion is also possible. The latter occurs when AONs targeted toward appropriate intron sequences are coupled to the business end of SR-proteins.

Exon skipping has been used to restore cryptic splicing, to change levels of alternatively spliced genes, and to restore disrupted open reading frames. This approach has been employed with a number of genes including Apolipoprotein B, Bcl-X, Collagen type 7, dystrophin, dysferlin, prostate-specific membrane antigen, IL-5 receptor alpha, MyD88, Tau, TNFalpha2 receptor, Titin, WT1, beta-globulin, and CFTR. Accordingly, in preferred embodiments, methods are provided for removing a proteolytic cleavage site from a protein, wherein the protein is not Apolipoprotein B, Bcl-X, Collagen type 7, dystrophin, dysferlin, prostate-specific membrane antigen, IL-5 receptor alpha, MyD88, Tau, TNFalpha2 receptor, Titin, WT1, beta-globulin, or CFTR; more preferably, the protein is not dystrophin.

In contrast to the previous uses for exon-skipping, provided is a method for removing a proteolytic cleavage site, HCHWA-D mutation, or the amino acids encoded by a trinucleotide repeat expansions in order to treat an individual, restore function to a protein, or reduce toxicity of a protein. The methods and oligonucleotides described herein are particularly useful for removing proteolytic cleavage sites, HCHWA-D mutation, or the amino acids encoded by trinucleotide repeat expansions from a protein, wherein the protein is involved in a neurodegenerative disorder.

Prevention of inclusion of a coding part for a proteolytic cleavage site, HCHWA-D mutation, or the amino acids encoded by a trinucleotide repeat expansion (in particular the polyQ repeat) into mature mRNA is, herein, preferably achieved by means of exon-skipping. Antisense oligonucleotides for exon-skipping typically enable skipping of an exon or the 5' or 3' part of it. Antisense oligonucleotides can be directed toward the 5' splice site, the 3' splice site, to both splice sites, to one or more exon-internal sites and to intron sequences, for instance, specific for the branch point. The latter enables skipping of the upstream exon.

Skipping of the nucleotides that code for the proteolytic cleavage site is typically achieved by skipping the exon that contains the nucleotides that code for the proteolytic cleavage site. This results in removal of the proteolytic recognition motif from the protein. The proteolytic cleavage site comprises the recognition sequence for the specific protease and the two amino acids between which the peptide linkage is cleaved by the protease. The proteolytic cleavage site can overlap the boundary of two adjacent exons or, if a part of the exon is skipped, overlap the exon sequence that contains the cryptic splice acceptor/donor sequence. In this embodiment, it is preferred to skip the exon sequence that codes for the peptide linkage that is cleaved by the protease. Whether or not a recognition sequence for a protease is actually used in nature depends, not only on the presence of the recognition sequence itself, but also on the location of the site in the folded protein. An internally located recognition site is typically not used in nature. Herein, a proteolytic cleavage site is an active proteolytic cleavage site that is actually used in nature.

Skipping of exonic sequences that contain the nucleotides that code for the proteolytic cleavage site, HCHWA-D mutation, or the amino acids encoded by a trinucleotide repeat expansion is preferably achieved by means of an AON that is directed toward an exon internal sequence. An oligonucleotide is said to be directed toward an exon internal sequence if the complementarity region that contains the sequence identity to the reverse complement of the target pre-mRNA is within the exon boundary. Presently, all exons that have been targeted by means of exon-skipping can be induced to be skipped from the mature mRNA, often with one AON and sometimes with two AONs directed toward the exon. However, not all AONs that can be designed induce detectable amounts of skipping. The most experience with exon-skipping has been gained in the DMD system. Using AON directed toward exon-internal sequences, it has been shown that all exons can be skipped (with the exception, of course, of the first and the last exon). However, not all AON designed against an exon-internal sequence actually induce detectable amounts of skipping of the targeted exon. The frequency of randomly selected exon-internal AON that induce skipping is around 30%, depending on the actual exon that is targeted. Since the first trials, however, the experience gained from AON that successfully induced skipping has resulted in a significant improvement of the success ratio of a designed AON (PMID: 18813282, Aartsma-Rus et al., *Mol. Ther.* 17(3):548 (2009). The factors that improve the success ratio include, among others, the predicted structure of the exon RNA at the target site, the exact sequence targeted, and the predicted presence or absence of specific SR-protein binding sites in the target site (ibidem).

Skipping of an exonic sequence encoding a proteolytic cleavage site, HCHWA-D mutation, or the amino acids encoded by a trinucleotide repeat expansion, is preferably such that downstream amino acids of the target protein are present in the newly formed protein. In this way, the proteolytic cleavage site, HCHWA-D mutation, or the amino acids encoded by a trinucleotide repeat expansion is removed while leaving much of the downstream protein intact. In this embodiment, the functionality of the modified protein is at least part of the functionality of the protein as present in normal individuals. Thus, preferably, the modified protein contains an "in-frame" deletion of the proteolytic cleavage site, HCHWA-D mutation, or the amino acids encoded by a trinucleotide repeat expansion. Preferably, the "in-frame" deleted protein has at least 20%, preferably at least 50% of the functionality of the unmodified protein in a normal individual. Thus, in a preferred embodiment, the number of nucleotides that is skipped is dividable by three. Skipping of an exon sequence that codes for a proteolytic cleavage site, HCHWA-D mutation, or the amino acids encoded by a trinucleotide repeat expansion is typically achieved by skipping the exon that contains this sequence. Skipping of the target exon is sufficient if this exon contains a number of nucleotides that is dividable by three. If the exon contains another number, it is preferred to also skip an adjacent exon, such that the total number of skipped nucleotides is again dividable by three. In most cases, the skipping of an adjacent exon is sufficient; however, if this also does not result in a number of skipped nucleotides that is dividable by three, the skipping of yet a further exon, adjacent to the two mentioned, may be necessary. Skipping of four or more exons is possible but often does not yield a lot of the correct protein. Sometimes, it is possible to skip only a part of an exon. This is either the 5' part of the 3' part of the exon. This occurs when the exon contains a cryptic 3' or 5' splice site that can be activated.

The term "pre-mRNA" refers to a non-processed or partly processed precursor mRNA that is synthesized from a DNA template in the cell nucleus by transcription. Within the context hereof, inducing and/or promoting skipping of an exon sequence that codes for a proteolytic cleavage site, as indicated herein, means that at least 1%, 10%, 20%, 30%, 40%, 50%, 60%, 70%, 80%, 90% or more of the mRNA encoding of the targeted protein in a cell will not contain the skipped exon sequence (modified/(modified+unmodified) mRNA). This is preferably assessed by PCR as described in the examples.

An AON hereof that induces skipping of an exon sequence that encodes a proteolytic cleavage site, HCHWA-D mutation, or the amino acids encoded by a trinucleotide repeat expansion, preferably comprises a sequence that is complementary to the exon. In some embodiments, the AON induces skipping of an exon in its entirety. In other embodiments, the AON induces skipping of a part of an exon, preferably the part encodes a proteolytic cleavage site. Preferably, the AON contains a continuous stretch of between 8 and 50 nucleotides that is complementary to the exon. An AON hereof preferably comprises a stretch of at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides that is complementary to the exon. In a preferred embodiment, the AON contains a continuous stretch of between 12 and 45 nucleotides that is complementary to the exon. More preferably, a stretch of between 15 and 41 nucleotides. Depending on the chemical modification introduced into the AON the complementary stretch may be at the smaller side of the range or at the larger side. A preferred antisense oligonucleotide, according disclosure, comprises a T-O alkyl phosphorothioate antisense oligonucleotide, such as 2'-O-methyl modified ribose (RNA), 2'-0-ethyl modified ribose, 2'-O-propyl modified ribose, and/or substituted derivatives of these modifications, such as halogenated derivatives. A most preferred AON, comprises of 2'-0-methyl phosphorothioate ribose. Such AON, typically, do not need to have a very large complementary stretch. Such AON, typically, contain a stretch of between 15 and 25 complementary nucleotides. As described herein below, another preferred AON hereof comprises a morpholino backbone. AON comprising such backbones typically contain somewhat larger stretches of complementarity. Such AON, typically, contain a stretch of between 25 and 40 complementary nucleotides. When in this invention reference is made to the range of nucleotides, this range includes the number(s) mentioned. Thus, by way of example, when reference is made to a stretch of between 8 and 50, this includes 8 and 50.

An AON hereof that is complementary to a target RNA is capable of hybridizing to the target RNA under stringent conditions. Typically, this means that the reverse complement of the AON is at least 90% and, preferably, at least 95% and, more preferably, at least 98% and, most preferably, at least 100% identical to the nucleotide sequence of the target at the targeted sited. An AON hereof, thus preferably, has two or less mismatches with the reverse complement of the target RNA, preferably, it has one or no mismatches with the reverse complement of the target RNA. In another preferred embodiment, the AON may be specifically designed to have one or more mismatches, preferably, one or two mismatches, e.g., in cases where it is necessary to reduce the affinity when the skipping of the 100% complementary AON is more effective than biologically desired in view of the necessary remaining protein activity. A mismatch is defined herein as a nucleotide or nucleotide analogue that does not have the same base pairing capacity in kind, not necessarily in amount, as the nucleotide it replaces. For instance, the base of uracil that replaces a thymine and vice versa, is not a mismatch. A preferred mismatch comprises an inosine. An inosine nucleotide is capable of pairing with any natural base in an RNA, i.e., capable of pairing with an A, C, G or U in the target RNA.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six-membered ring, and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane. One study comparing several of these methods, found that scrape loading was the most efficient method of delivery; however, because the morpholino backbone is uncharged, cationic lipids are not effective mediators of morpholino oligonucleotide uptake in cells. A recent report demonstrated triplex formation by a morpholino oligonucleotide and, because of the non-ionic backbone, these studies showed that the morpholino oligonucleotide was capable of triplex formation in the absence of magnesium. A modified backbone is typically preferred to increase nuclease resistance of the AON, the target RNA or the AON/target RNA hybrid, or a combination thereof. A modified backbone can also be preferred because of its altered affinity for the target sequence compared to an unmodified backbone. An unmodified backbone can be RNA or DNA, preferably it is an RNA backbone.

It is further preferred that the linkage between the residues in a backbone does not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent, comprises a Peptide Nucleic Acid (PNA), having a modified polyamide backbone (Nielsen, et al. (1991), *Science* 254:1497-1500). PNA-based molecules are true mimics of DNA molecules in terms of base-pair recognition. The backbone of the PNA is composed of 7V-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005), *Chem. Commun.*, 495-497). Since the backbone of a PNA molecule contains no charged phosphate groups, PNA-RNA hybrids are usually more stable than RNA-RNA or RNA-DNA hybrids, respectively (Egholm et al. (1993), *Nature* 365:566-568).

A further preferred backbone comprises a morpholino nucleotide analog or equivalent, in which the ribose or deoxyribose sugar is replaced by a six-membered morpholino ring. A most preferred nucleotide analog or equivalent comprises a phosphorodiamidate morpholino oligomer (PMO), in which the ribose or deoxyribose sugar is replaced by a six-membered morpholino ring, and the anionic phosphodiester linkage between adjacent morpholino rings is replaced by a non-ionic phosphorodiamidate linkage.

In yet a further embodiment, a nucleotide analogue or equivalent hereof, comprises a substitution of one of the non-bridging oxygens in the phosphodiester linkage. This modification slightly destabilizes base-pairing but adds significant resistance to nuclease degradation. A preferred nucleotide analogue or equivalent, comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent hereof comprises one or more sugar moieties that are mono- or disubstituted at the 2', 3' and/or 5' position, such as a —OH; —F; substituted or unsubstituted, linear or branched lower (C1—C10) alkyl, alkenyl, alkynyl, alkaryl, allyl, aryl, or aralkyl that may be interrupted by one or more heteroatoms; O-, S-, or N-alkyl; O-, S-, or N-alkenyl; O-, S- or N-alkynyl; O-, S-, or N-allyl; O-alkyl-0-alkyl, -methoxy, -aminopropoxy; -aminoxy; methoxyethoxy; -dimethylaminooxyethoxy; and -dimethylaminoethoxyethoxy. The sugar moiety can be a pyranose or derivative thereof, or a deoxypyranose or derivative thereof, preferably, a ribose or a derivative thereof, or a deoxyribose or a derivative thereof. Such preferred derivatized sugar moieties comprise Locked Nucleic Acid (LNA), in which the 2'-carbon atom is linked to the 3' or 4' carbon atom of the sugar ring, thereby forming a bicyclic sugar moiety. A preferred LNA comprises 2'-0, 4'-C-ethylene-bridged nucleic acid (Morita et al. 2001, *Nucleic Acid Res.*, Supplement No. 1:241-242). These substitutions render the nucleotide analogue, or equivalent RNase H and nuclease, resistant and increase the affinity for the target RNA. As is apparent to one of skill in the art, the substitutions provided herein render the double-stranded complex of the antisense oligonucleotide with its target pre-mRNA RNase H resistant. Accordingly, preferred oligonucleotides bind to the pre-mRNA of the protein to form a double-stranded nucleic acid complex and are chemically modified to render the double-stranded nucleic acid complex RNAse H resistant.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide hereof has at least two different types of analogues or equivalents.

As mentioned hereinabove, a preferred AON hereof comprises a T-O alkyl phosphorothioate antisense oligonucleotide, such as 2'-O-methyl modified ribose (RNA), 2'-O-ethyl modified ribose, 2'-O-propyl modified ribose, and/or substituted derivatives of these modifications, such as halogenated derivatives. A most preferred AON comprises 2'-O-methyl phosphorothioate ribose.

An AON can be linked to a moiety that enhances uptake of the antisense oligonucleotide in cells. Examples of such moieties are cholesterols, carbohydrates, vitamins, biotin, lipids, phospholipids, cell-penetrating peptides including but not limited to antennapedia, TAT, transportan and positively charged amino acids, such as oligoarginine, poly-arginine, oligolysine or polylysine, antigen-binding domains, such as provided by an antibody, a Fab fragment of an antibody, or a single chain antigen binding domain, such as a cameloid single domain antigen-binding domain.

Preferably, additional flanking sequences are used to modify the binding of a protein to the AON, or to modify a thermodynamic property of the AON, more preferably, to modify target RNA binding affinity.

AON administration in humans is typically well tolerated. Clinical manifestations of the administration of AON in human clinical trials have been limited to the local side effects following subcutaneous (SC) injection (on the whole intravenous (i.v.) administration seems to be better tolerated) and generalized side effects, such as fever and chills that similar to the response to interferon administration, respond well to paracetamol. More than 4000 patients with different disorders have been treated so far using systemic delivery of first generation AON (phosphorothioate backbone), and approximately 500 following local administration. The typical dosage used ranged from 0.5 mg/kg every other day for one month in Crohn's disease, to 200 mg twice weekly for three months in rheumatoid arthritis, to higher dosages of 2 mg/kg day in other protocols dealing with malignancies. Fewer patients (approximately 300) have been treated so far using new generation AON (uniform phosphorothioated backbone with flanking 2' methoxyethoxy wing) delivered systemically at doses comprised between 0.5 and 9 mg/kg per week for up to three weeks.

Delivery of AON to cells of the brain can be achieved by various means. For instance, they can be delivered directly to the brain via intracerebral inoculation (Schneider et al., *Journal of Neuroimmunology* 195 (2008) 21-27), intraparenchymal infusion (Broaddus et al., *J Neurosurg.* 1998 April; 88(4):734-42), intrathecal, or intraventricularly. Alternatively, the AON can be coupled to a single domain antibody or the variable domain thereof (VHH) that has the capacity to pass the blood brain barrier. Nanotechnology has also been used to deliver oligonucleotides to the brain, e.g., a nanogel consisting of cross-linked PEG and polyethylenimine. Encapsulation of AON in liposomes is also well known to one of skill in the art. The AONs can also be introduced into the cerebral spinal fluid.

An AON hereof preferably comprises a sequence that is complementary to part of the pre-mRNA, as defined herein. In a more preferred embodiment, the length of the complementary part of the oligonucleotide is of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides. Preferably, additional flanking sequences are used to modify the binding of a protein to the molecule or oligonucleotide, or to modify a thermodynamic property of the oligonucleotide, more preferably, to modify target RNA binding affinity. An AON hereof may further comprise additional nucleotides that are not complementary to the target site on the target pre-mRNA. In a preferred embodiment, an AON contains between 8 and 50 nucleotides. An AON hereof preferably comprises a stretch of at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides. In a preferred embodiment, the AON contains a continuous stretch of between 12 and 45 nucleotides, more preferably, a stretch of between 15 and 41 nucleotides. Depending on the chemistry of the backbone, as indicated hereinabove, an AON hereof contains between 15 and 25 nucleotides. An AON hereof with a morpholino backbone typically contains a stretch of between 25 and 40 nucleotides. In a preferred embodiment, the indicated amounts for the number of nucleotides in the AON refers to the length of the complementarity to the target pre-mRNA, preferably to an exon internal sequence, however, the target sequence can also be a 5' or a 3' splice site of an exon or an intron sequence, such as preferably a branch point. In another preferred embodiment, the indicated amounts refer to the total number of nucleotides in the AON.

Preferably, the complementary part is at least 50% of the length of the oligonucleotide hereof, more preferably, at least 60%, even more preferably, at least 70%, even more preferably, at least 80%, even more preferably, at least 90% or even more preferably, at least 95%, or even more preferably, 98% and most preferably up to 100% of the length of the oligonucleotide hereof, with the putative exception of deliberately introduced specific mismatches, e.g., for downregulating affinity when necessary.

With respect to AON that also contain additional nucleotides, the total number of nucleotides typically does not exceed 50, and the additional nucleotides preferably range in number from between 5 and 25, preferably from 10 and 25, more preferably, from 15 and 25. The additional nucleotides typically are not complementary to the target site on the pre-mRNA but may be complementary to another site on the pre-mRNA or may serve a different purpose and not be complementary to the target pre-mRNA, i.e., less than 95% sequence identity of the additional nucleotides to the reverse complement of the target pre-mRNA.

The proteolytic cleavage site that is to be removed from a protein by a method or AON hereof is preferably a serine endoprotease cleavage site, a metaloendopeptidase cleavage site, a secretase cleavage site and/or a caspase cleavage site. In a particularly preferred embodiment, the cleavage site is a caspase cleavage site or secretase cleavage site. Caspases are a family of intracellular cysteine proteases that play a central role in the initiation and execution of programmed cell death. The term caspases is a short form for Cystein Aspartate-specific Proteases: their catalytical activity depends on a critical cystein-residue within a highly conserved active-site pentapeptide QACRG, and the caspases specifically cleave their substrates after Asp residues (also the serine-protease granzyme B has specificity for Asp in the P1 position of substrates). More than ten different members of the caspase family have been identified in mammals. According to a unified nomenclature, the caspases are referred to in the order of their publication: so Caspase-1 is ICE (Interleukin-1beta-Converting Enzyme), the first aspartate-specific cystein protease described. The secretase family of proteases is subdivided into three groups, the alpha-, beta- and gamma-secretases. In a preferred embodiment, the secretase is a gamma-secretase.

The protein from which the proteolytic cleavage site or one or more trinucleotide repeats is to be removed can be any protein that contains a proteolytic cleavage site or trinucleotide repeat. In a preferred embodiment, the protein is a mammalian protein, more preferably, a primate protein. In a particularly preferred embodiment, the protein is a human protein. In a preferred embodiment, the protein is associated with a disease in humans. In a particularly preferred embodiment, the protein is associated with a triplet repeat disease in humans. Preferably, a polyglutamine repeat disease.

In a preferred embodiment, the protein comprises a caspase cleavage site or secretase cleavage site. Preferably, the protein comprises a caspase-3 or -6 proteolytic cleavage site. Preferably, the protein is a protein that is normally present in the brain of a mammal. In a particularly preferred embodiment, the gene encoding the protein is a mutant gene that encodes a trinucleotide repeat expansion when compared to the gene of a normal individual.

In a particularly preferred embodiment, the protein is a protein encoded by one of the genes listed in Table 1a or 1b. In a particularly preferred embodiment, the gene is a mutant gene that is the causative gene in a polyglutamine disorder, preferably a gene of Table 1a. In a particularly preferred embodiment, the gene is the huntingtin (Htt) gene. Htt is expressed in all mammalian cells. The highest concentrations are found in the brain and testes, with moderate amounts in the liver, heart, and lungs. The function of Htt in humans is as yet not entirely resolved. Htt interacts among others with proteins, which are involved in transcription, cell signaling and intracellular transporting. In humans the gene, and in particular mutants thereof, is associated with Huntington's disease (HD). HD is a progressive neurodegenerative genetic disorder, which affects muscle movement and muscle coordination and leads to cognitive decline and dementia. It typically becomes noticeable in middle age. HD is the most common genetic cause of abnormal involuntary writhing movements called chorea and is much more common in people of Western European descent than in those from Asia or Africa. The disease is caused by an autosomal dominant mutation of the Htt-gene. A child of an affected parent has a 50% risk of inheriting the disease.

For the Htt gene it is preferred that the caspase-6 proteolytic cleavage site encoded by exon Htt exon 12 is removed from the Huntingtin protein. It is preferred that the coding region that codes for the proteolytic cleavage site is removed "in frame," so as to allow incorporation of the normal downstream amino acid sequence into the mutant protein. In one embodiment, the "in-frame" removal is achieved by providing the cell with an AON that enables skipping of exon 12 and an AON that enables skipping of exon 13 of the Htt gene. In another preferred embodiment, the "in-frame" removal is achieved by providing the cell with an AON capable of inducing exon skipping directed toward the region delimited by nucleotides 269-297 of exon 12 of the Htt gene. In a preferred embodiment, the AON is directed toward region delimited by nucleotides 207 until 341 of exon 12. It is preferred that the AON is directed toward the internal region delimited by nucleotides 207 until 341 of exon 12. This includes nucleotides 207 and 341. It has been found that AON directed toward the preferred regions induce skipping of the last 135 nucleotides of exon 12, thereby producing an "in-frame" complete deletion of two active caspase 3 cleavage sites at amino acid 513 and 552, and removal of the first amino acid of an active caspase 6 site, partially located in exon 12 and partially in exon 13. AON HDEx12_1 (Table 2) activates a cryptic splice site at nucleotide 206 in exon 12, leading to the absence of the remainder of exon 12 from the formed mRNA.

Further provided is an isolated and/or recombinant modified Htt mRNA having a deletion of at least nucleotides 207 until 341 of exon 12. The modified Htt mRNA preferably comprises the exons 1-11, the first 206 nucleotides of exon 12 and exons 13-67. In another preferred embodiment, the modified Htt mRNA comprises the exons 1-11, 14-67.

In another embodiment, provided is an isolated and/or recombinant modified Htt protein comprising a deletion of amino acids 538-583. The modified Htt protein preferably comprises the amino acid sequence encoded by exons 1-11, the first 206 nucleotides of exon 12, and exons 13-67. In another preferred embodiment, the modified Htt protein comprises the amino acid sequence encoded by exons 1-11, 14-67.

In yet another embodiment, provided is an isolated and/or recombinant cell comprising a modified Htt mRNA and/or a modified Htt protein as indicated herein above. Preferably, the cell comprises an Htt gene comprising a coding region of a polyglutamine repeat, the length of which is associated with HD.

For the ATXN3 gene, it is preferred that the calpain cleavage sites in exon 7 is removed from the protein. It is preferred that the coding region that codes for the proteolytic cleavage site is removed "in frame," so as to allow incorporation of the normal downstream amino acid into the mutant protein. In one embodiment, the "in-frame" removal is achieved by providing the cell with an AON that enables skipping of exon 7 and an AON that enables skipping of exon 8 of the ATXN3 gene.

For the ATXN3 gene, it is preferred that the calpain and caspase cleavage sites in exons 8 and 9 are removed from the protein. Accordingly, a cell is provided with an anti-sense oligonucleotide(s) that induces skipping of exons 8 and 9, for removing the proteolytic cleavage site from the protein in a cell that produces pre-mRNA encoding the protein.

For the ATN1 gene, it is preferred that the caspase 3 cleavage site near the N-terminus of the protein and the polyglutamine tract ($^{106}$DSLD$^{109}$) in exon 5 is removed from the protein. It is preferred that the coding region that codes for the proteolytic cleavage site is removed "in frame," so as to allow incorporation of the normal downstream amino acid into the mutant protein. In one embodiment, the "in-frame" removal is achieved by providing the cell with an AON that enables skipping of exon 5 and an AON that enables skipping of exon 6 of the ATN1 gene. In a preferred embodiment, the AON comprises a sequence as depicted in Table 2 under DPRLA AON. Dentatorubral-pallidoluysian atrophy (DRPLA) is an autosomal dominant spinocerebellar degeneration caused by an expansion of a CAG repeat encoding a polyglutamine tract in the atrophin-1 protein.

Further provided is an AON hereof, of preferably between 14 and 40 nucleotides, that induces skipping of an exonic sequence that encodes a proteolytic cleavage site in a protein, the HCHWA-D mutation, or the amino acids encoded by a trinucleotide repeat expansion. In a preferred embodiment, provided is an AON, as indicated hereinabove, comprising a sequence as depicted in Table 2. The AON is suitable for skipping the indicated exon of the gene. In a particularly preferred embodiment, the AON comprises the sequence of HDEx12_1 of Table 2. In another preferred embodiment, provided is an AON, as indicated hereinabove, that is specific for the region identified by a sequence of an AON depicted in Table 2. In a preferred embodiment, the AON comprises at least 10 consecutive nucleotides of the region identified by an oligonucleotide as depicted in Table 2. In a particularly preferred embodiment, provided is an AON, as indicated hereinabove, that is specific for the region identified by a sequence of HDEx12_1 of Table 2.

Further provided is the use of exon-skipping in a cell for removing a proteolytic cleavage site from a protein. Further provided is the use of an AON that induces skipping of an exon that encodes a proteolytic cleavage site in a protein, for removing the proteolytic cleavage site from the protein in a cell that produces pre-mRNA encoding the protein. Further provided is an oligonucleotide of between 14 and 40 nucleotides that induces skipping of an exon that encodes a proteolytic cleavage site in a protein for use in the treatment of a disease that is associated with a proteolytic cleavage product of the protein.

In another embodiment, provided is a method for altering the proteolytic processing of a protein that comprises a proteolytic cleavage site comprising providing a cell that produces a pre-mRNA that codes for the protein with an AON that is specific for the pre-mRNA; and that prevents inclusion of the code for the proteolytic cleavage site into mature mRNA produced from the pre-mRNA, the method further comprising allowing translation of the mRNA to produce the protein of which the proteolytic processing is altered.

Further provided is the use of exon-skipping in a cell for removing the amino acids encoded by a trinucleotide repeat expansion from a protein. Further provided is the use of an AON that induces skipping of an exonic sequence that comprises a trinucleotide repeat in a pre-mRNA. Preferably, the protein is encoded by a gene listed in Table 1a or 1b.

Further provided is an oligonucleotide of between 14 and 40 nucleotides that induces skipping of an exonic sequence that comprises a trinucleotide repeat expansion in a pre-mRNA for use in the treatment of a disease that is associated with the amino acids encoded by a trinucleotide repeat expansion of the protein (see, e.g., Tables 1a and 1b).

Further provided is the use of exon-skipping in a cell for removing the HCHWA-D mutation from an APP pre-mRNA. Further provided is the use of an AON that induces skipping of an exonic sequence that contains the HCHWA-D mutation in a mutant APP protein for removing the HCHWA-D mutation from the protein in a cell that produces pre-mRNA encoding the protein. Further provided is an oligonucleotide of between 14 and 40 nucleotides that induces skipping of an exonic sequence that encodes the HCHWA-D mutation in APP protein for use in the treatment of HCHWA-D.

Further provided is a non-human animal comprising an oligonucleotide hereof. Preferably, the non-human animal comprises a mutant gene that encodes a trinucleotide repeat expansion when compared to the gene of a normal individual.

Further provided is a modified human protein from which a proteolytic cleavage site is removed by means of exon skipping. Further provided is an mRNA encoding a modified human protein from which a proteolytic cleavage site is removed by means of exon skipping.

Further provided is a modified human APP protein from which the HCHWA-D mutation is removed by means of exon skipping. Further provided is an mRNA encoding a modified human APP protein from which the HCHWA-D mutation is removed by means of exon skipping.

Further provided is a cell encoding a human protein comprising a proteolytic cleavage site, wherein the cell contains an AON hereof for removing the proteolytic cleavage site from the protein in the cell.

Further provided is a cell encoding a human protein comprising the amino acids encoded by a trinucleotide repeat expansion, wherein the cell contains an AON hereof for removing the amino acids encoded by a trinucleotide repeat expansion from the protein in the cell. Preferably, the protein is encoded by a gene listed in Table 1a or 1b.

Further provided is a cell encoding a human APP protein comprising the HCHWA-D mutation, wherein the cell contains an AON hereof for removing the HCHWA-D mutation from the protein in the cell.

The general nomenclature of cleavage site positions of the substrate were formulated by Schecter and Berger, 1967-68 [Schechter and Berger, 1967], [Schechter and Berger, 1968]. They designate the cleavage site between P1 and P1', incrementing the numbering in the N-terminal direction of the cleaved peptide bond (P2, P3, P4, etc.). On the carboxyl side of the cleavage site numbering are likewise incremented (P1', P2', P3', etc.).

BRIEF DESCRIPTION OF THE DRAWINGS

FIG. 1A) Patient derived HD fibroblasts were treated with 1, 25, 150, and 1000 nM HDEx12_1. β-Actin was taken along as loading control. Increasing the AON concentration from 1 nM to 25 nM resulted in a higher skip percentage from 16% to 92% as was measured by Lab-on-a-Chip. The highest skip percentage of 95% was obtained with 150 nM HDEx12_1. Too high concentration of AON resulted in inefficient skip. In the Mock I control (transfection agent only) no skip is visible as expected. The potency of HDEx12_1 exon 12 skip was also seen in another HD and control fibroblast cell line and human neuroblastoma SH-SY5Y cells. FIG. 1B) Schematic representation of PCR of HD exons 9 to 14. Both schematic representation of normal (top) and shorter, skipped exon 12 (bottom) products are shown.

FIG. 4: Partial amino acid sequence of the huntingtin protein (see SEQ ID NO:227). Underlined are the amino acids encoded by exon 12 and 13. Highlighted in red is the part of the protein that is currently skipped by the exon 12 AON. In bold is the caspase-3 site $^{510}$DSVD$^{513}$, caspase-3 site $^{549}$DLND$^{552}$ and caspase-6 site $^{583}$IVLD$^{586}$.

FIG. 5A) Diagram of complete htt protein. PolyQ indicates the polyglutamine tract. The arrows indicate the caspase cleavage sites and their amino acid positions. FIG. 5B) Amino-terminal part of the htt protein. Htt exon 1 to 17 are depicted. The arrows indicate the caspase cleavage sites and their amino acid positions. FIG. 5C) Schematic representation and amino acid sequence of htt exon 12 and 13 with the caspase cleavage motifs depicted in bold. Exon boundaries are shown with vertical grey bars (SEQ ID NO:230). FIG. 5D) Partial amino acid and nucleotide sequence of htt exon 12 and 13 (SEQ ID NOS:231 and 233). Caspase cleavage motifs are depicted in bold and exon boundary is shown with vertical grey bar. The light grey highlighted sequence denotes the part which is skipped after HDEx12_1 AON treatment.

FIG. 20: APP isoforms in human and mouse. Schematic representation of the exon-intron structure of two different human APP isoforms (APP751 and APP770), and mouse APP (SEQ ID NO:255; NO:254 and NO:256, respectively). The exon containing the HCHWA-D mutation is indicated by the arrow head. Below the exon-intron scheme is the amino acid sequence encoded for by the exons surrounding the HCHWA-D mutation-containing exon, where the HCHWA-D mutation is indicated in italics, and the gamma-secretase cleavage site is indicated by underline.

DETAILED DESCRIPTION

EXAMPLES

Example 1

Figures 1A, 1B:
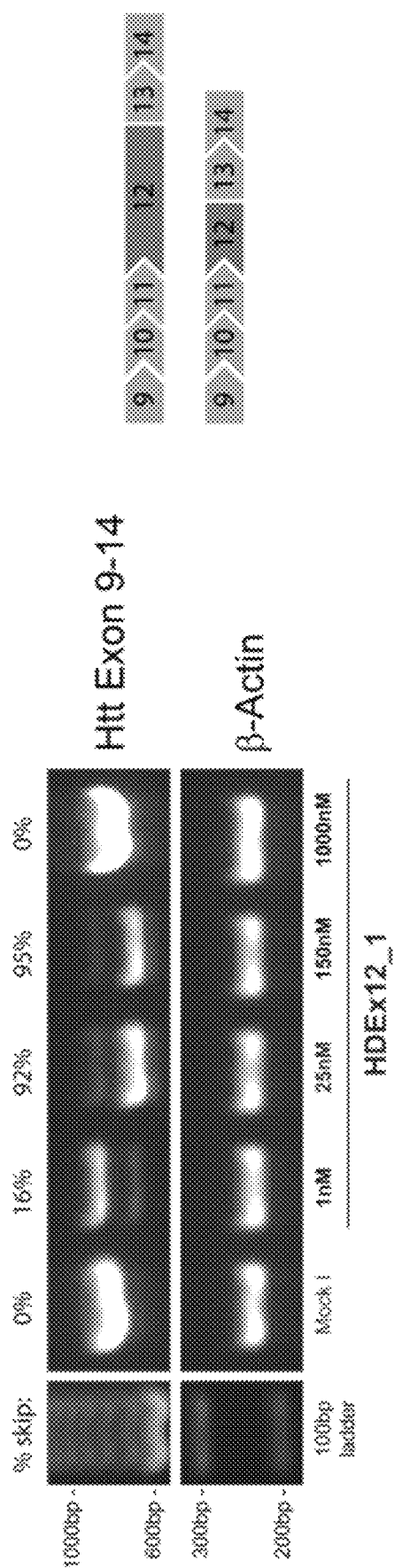
FIGS. 1A and 1B: Exon skipping after transfection with various concentrations HDEx12_1 AON.

AON-mediated exon skipping in neurodegenerative diseases to remove proteolytic cleavage sites. AON-mediated exon skipping in Huntington's disease to remove proteolytic cleavage sites from the huntingtin protein.
Methods
AONs and Primers
All AONs consisted of 2'-O-methyl RNA and full length phosphorothioate backbones.
Cell Cultures and AON Transfection
Patient fibroblast cells and human neuroblastoma cells were transfected with AONs at concentrations ranging between 1 and 1000 nM using Polyethylenemine (PEI) ExGen500 according to the manufacturer's instructions, with 3.3 µl PEI per µg of transfected AON. A second transfection was performed 24 hours after the first transfection. RNA was isolated 24 hours after the second transfection and cDNA was synthesized using random hexamer primers.
Cell Lines Used:
 FLB73 Human Fibroblast Control
 GM04022 Human Fibroblast HD
 GM02173 Human Fibroblast HD
 SH-SY5Y Neuroblastoma Control
Quantitative Real-Time PCR (qRT-PCR) was carried out using the LightCycler® 480 System (Roche) allowing for quantification of gene expression.
Agarose Gel and Sanger Sequencing
All PCR products were run on 2% agarose gel with 100 base pair ladders. Bands were isolated using the QIAgen® PCR purification kit according to manufacturer's instructions. The samples were then sequenced by Sanger sequencing using the Applied Biosystems BigDyeTerminator v3.1 kit.
Lab-On-a-Chip
Lab-on-a-Chip automated electrophoresis was used to quantify the PCR products using a 2100 Bioanalyzer. Samples were made 1 part β-Actin primed product, as a reference transcript, to 5 parts experimental PCR products. The samples were run on a DNA 1000 chip.
Western Blot
Protein was isolated from cells 72 hours after the first transfection and run on a Western blots, transferred onto a PVDF membrane and immunolabeled with primary antibodies recognizing htt, 1H6 or 4C8 (both 1:1,000 diluted)
Materials
AONs and primers were obtained from Eurogentec, Liege, Belgium.
AON sequences:

```
                                        (SEQ ID NO: 1)
    HDEx12_1: CGGUGGUGGUCUGGGAGCUGUCGCUGAUG (SEQ ID NO: 2)
    HDEx12_2: UCACAGCACACACUGCAGG (SEQ ID NO: 3)
    HDEx13_1: GUUCCUGAAGGCCUCCGAGGCUUCAUCA (SEQ ID NO: 4)
    HDEx13_2: GGUCCUACUUCUACUCCUUCGGUGU
```

Figure 2:
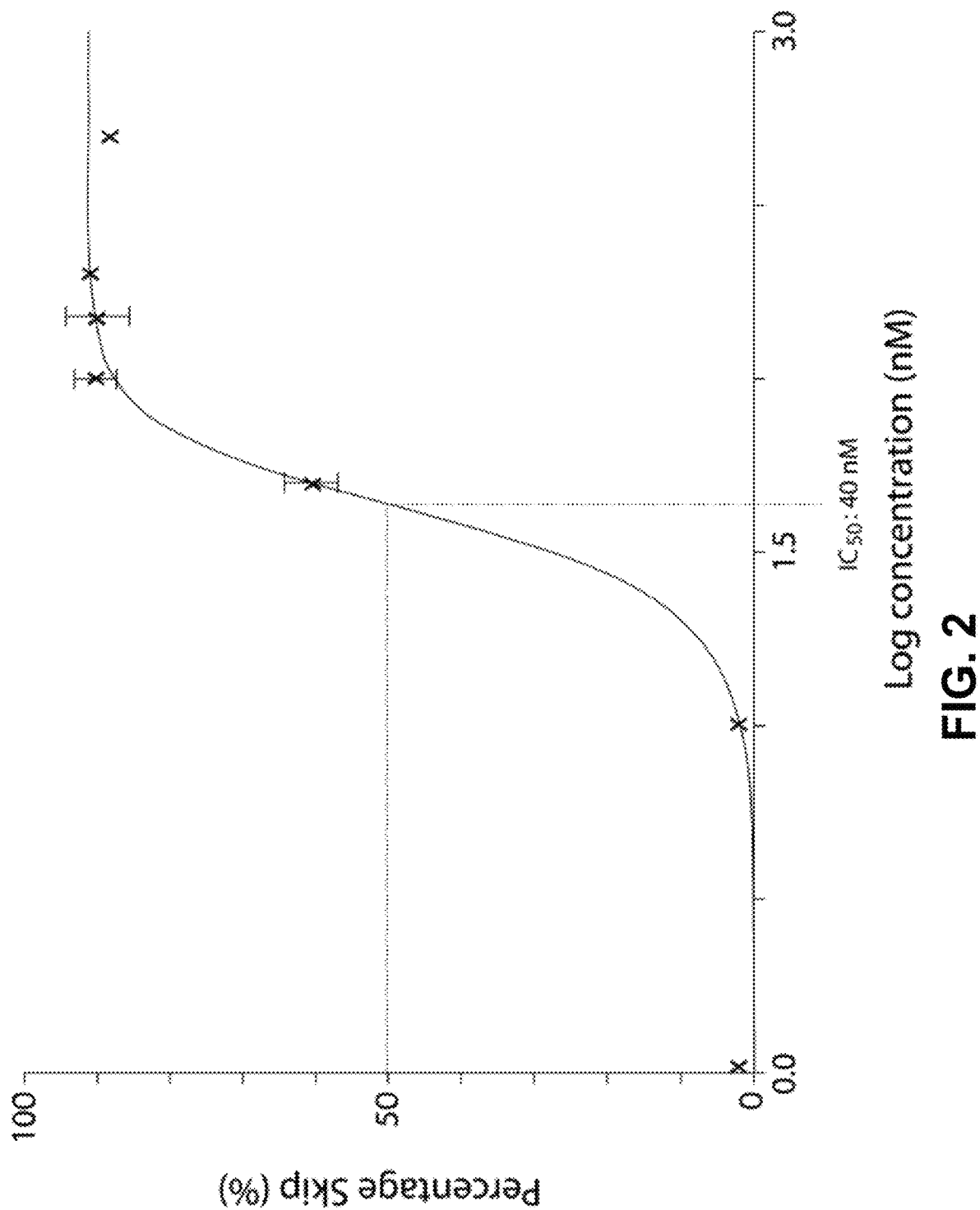
FIG. 2: Log dose response curve of HDEx12_1 AON in a HD fibroblast cell line. X-axis displays the log concentration (nM) and y-axis the percentage of skip. The half maximum inhibitory value (IC50) of the HDEx12_1 AON was found to be 40 nM. The optimal percentage exon 12 skip was achieved with an AON concentration of 150 nM and higher. Results shown as mean±SEM (n=2-3).
Figure 3A:
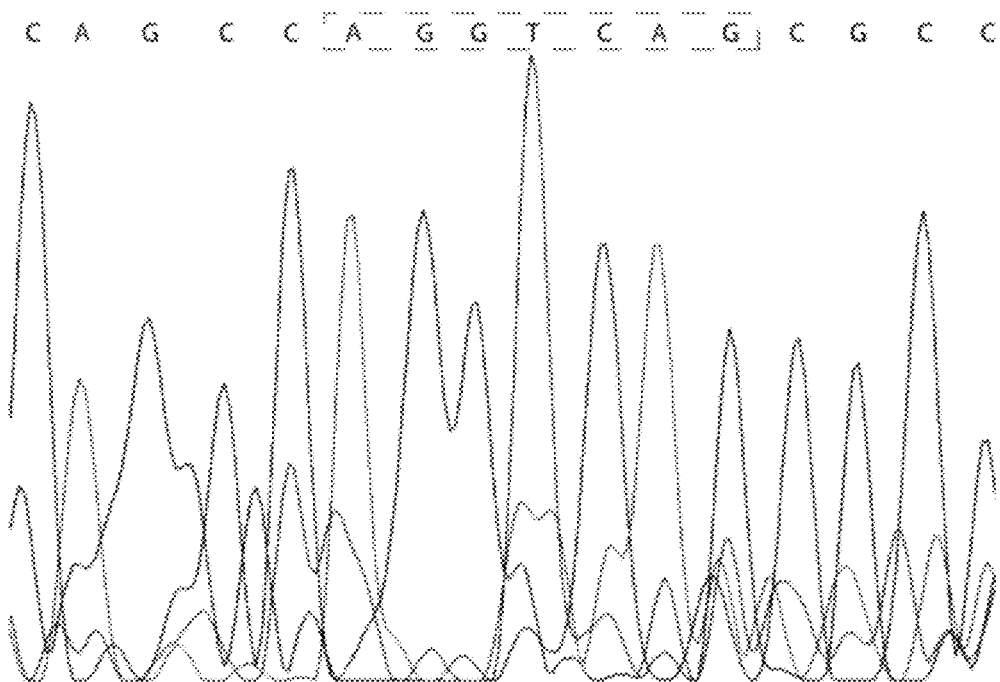
FIGS. 3A and 3B: Sanger sequencing of normal (FIG. 3A) and skipped (SEQ ID NO:228) (FIG. 3B) PCR product (SEQ ID NO:229). HDEx12_1 AON transfection in a HD fibroblast cell line resulted in an in-frame skip of 135 nucleotides, which corresponds with 45 amino acids. The observed skip is caused by the activation of an alternative splice site (AGIGTRAG, see dashed box (positions 6-12 of SEQ ID NO:228)), resulting in an alternative splice site exon isoform. This partial exon 12 skip results in the deletion of an active caspase-3 site $^{549}$DLND$^{552}$ and partial removal of the first amino acid (Isoleucine) of an active caspase-6 site ($^{583}$IVLD$^{586}$).
Figure 3B:
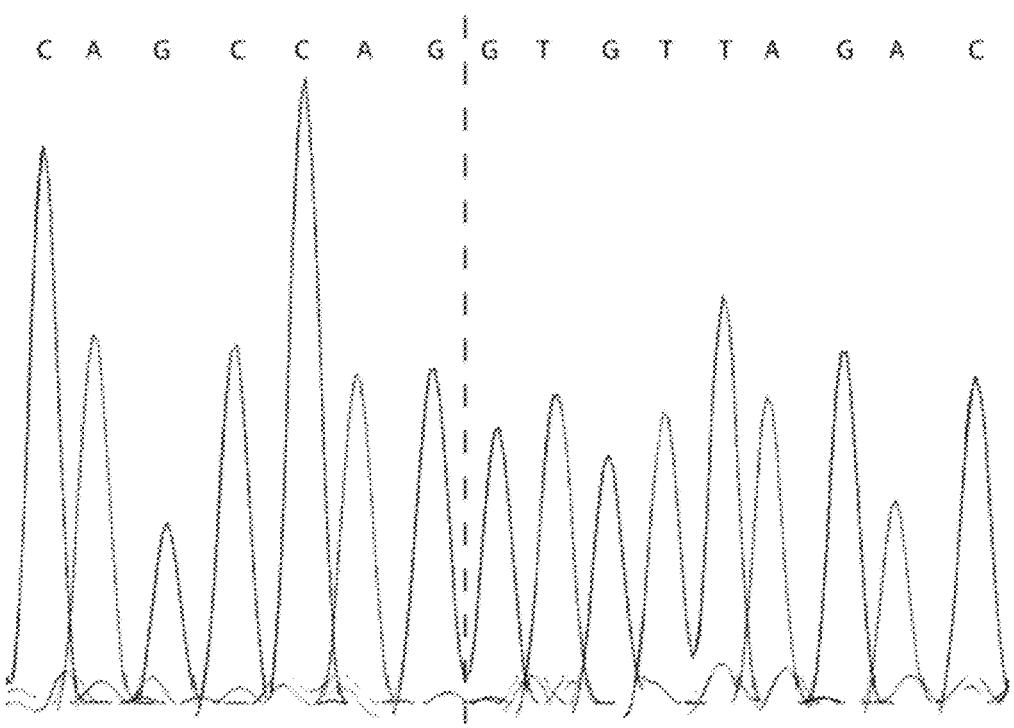
Figure 5A:
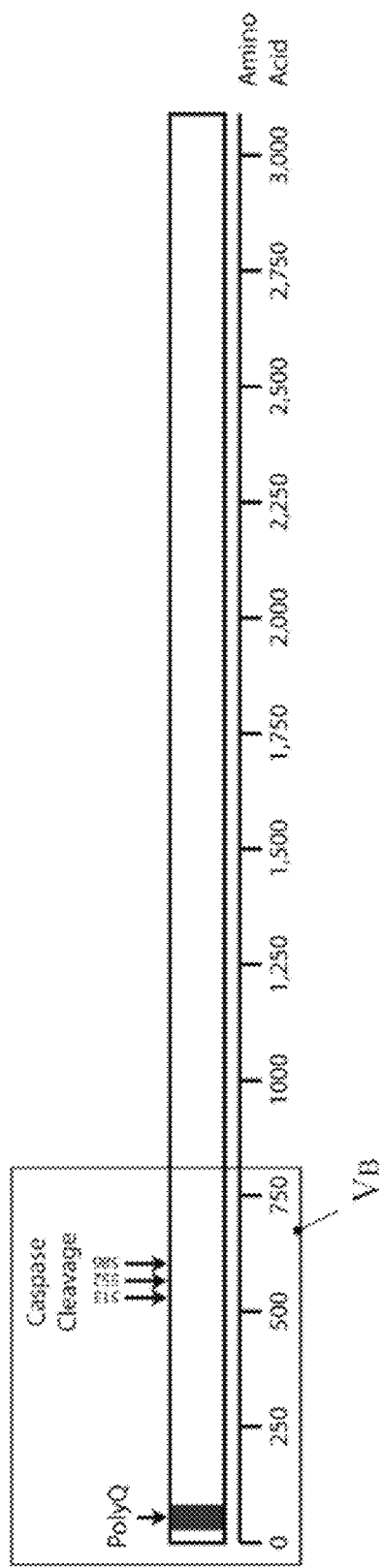
FIGS. 5A-5D: Schematic diagram of huntingtin.
Figure 5B:
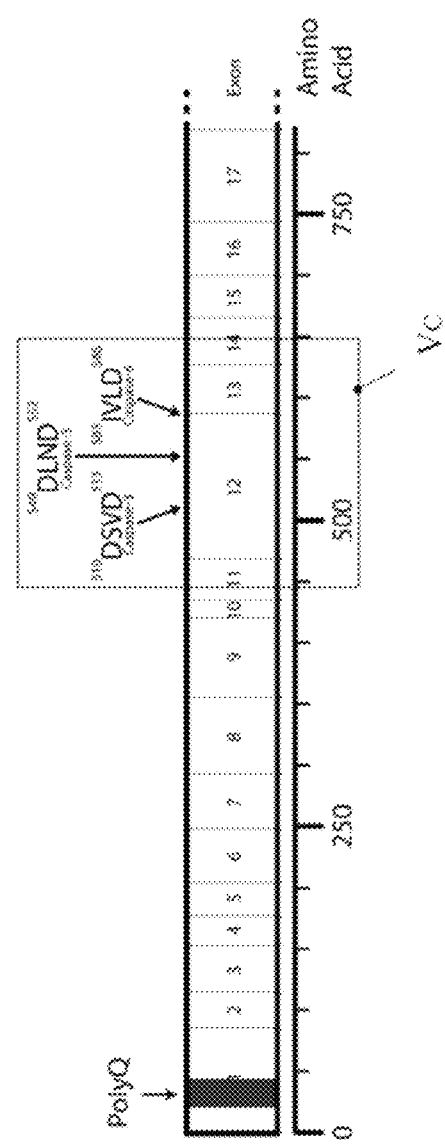
Figures 5C, 5D:
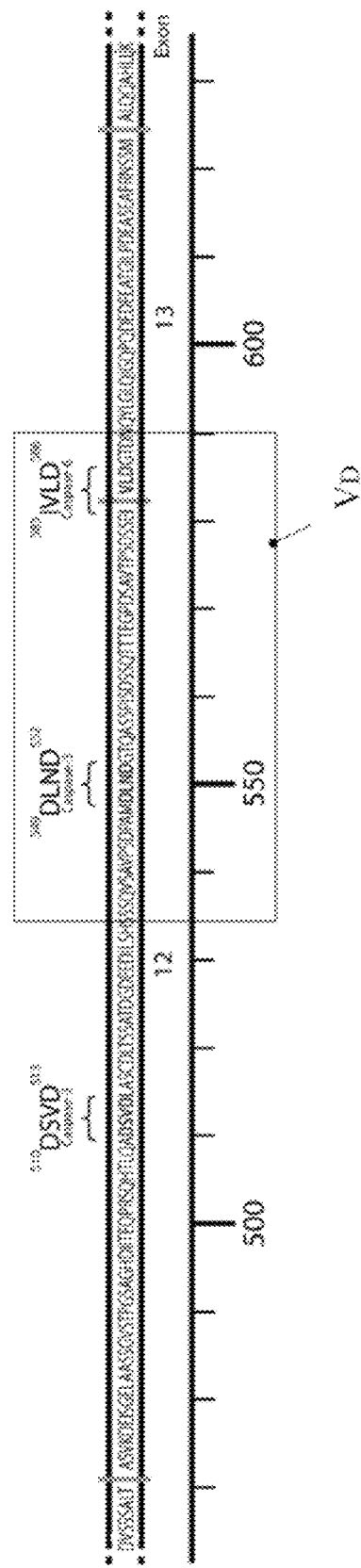

Patient fibroblast cell lines GM04022 and GM02173 were obtained from Coriell, Institute for Medical Research, Camden, USA and control fibroblast cell line FLB73 from Maaike Vreeswijk, LUMC.
Results
Transfection of AON HDEx12_1 in both patient derived HD fibroblast and human neuroblastoma cells showed an efficient skip (see FIGS. 1A and 1B) of exon 12. The optimal percentage exon 12 skip was achieved with a concentration of 150 nM, but a skip was already visible at 1 nM (see FIG. 2). Sanger sequencing confirmed that the last 135 nucleotides of exon 12 were skipped after transfection of the cells with AON HDEx12_1. This corresponded to deletion of 45 amino acids containing two active caspase 3 sites and the first amino acid of an active caspase 6 site (see FIGS. 3A, 3B, and 4). In silico analysis revealed that the observed skip is likely due to the activation of the alternative splice site AGIGTRAG (positions 6-12 of SEQ ID NO:228), resulting in an alternative splice site exon isoform (see FIGS. 3A, 3B).

CONCLUSIONS

With AON HDEx12_1, a partial skip of exon 12 of the huntingtin transcript was shown that results in a truncated but in-frame protein product. Using different cell lines, this partial exon 12 skip was confirmed by Sanger sequencing and in silico analysis revealed an alternative splice site in exon 12 that is likely the cause of this partial skip. This skipped protein product misses two complete caspase-3 cleavage sites located in exon 12, and the first amino acid of the caspase-6 cleavage site that is located on the border of exon 12 and 13. Recent mouse model data showed that the preferred site of in vivo htt cleavage to be at amino acid 552, which is used in vitro by either caspase-3 or caspase-2[1] and that mutation of the last amino acid of the caspase 6 cleavage site at amino acid position 586 reduces toxicity in an HD model[2].

Functional analysis will be performed to determine whether AON HDEx12_1 can reduce the toxicity of mutant huntingtin and to determine the level of prevention of formation of toxic N-terminal huntingtin fragments. Also other AONs will be tested to completely skip exons 12 and 13 of the huntingtin transcript.

Example 2: AON Mediated Skipping of Htt Exon 12 or 13 in Human Fibroblasts

Figure 6:
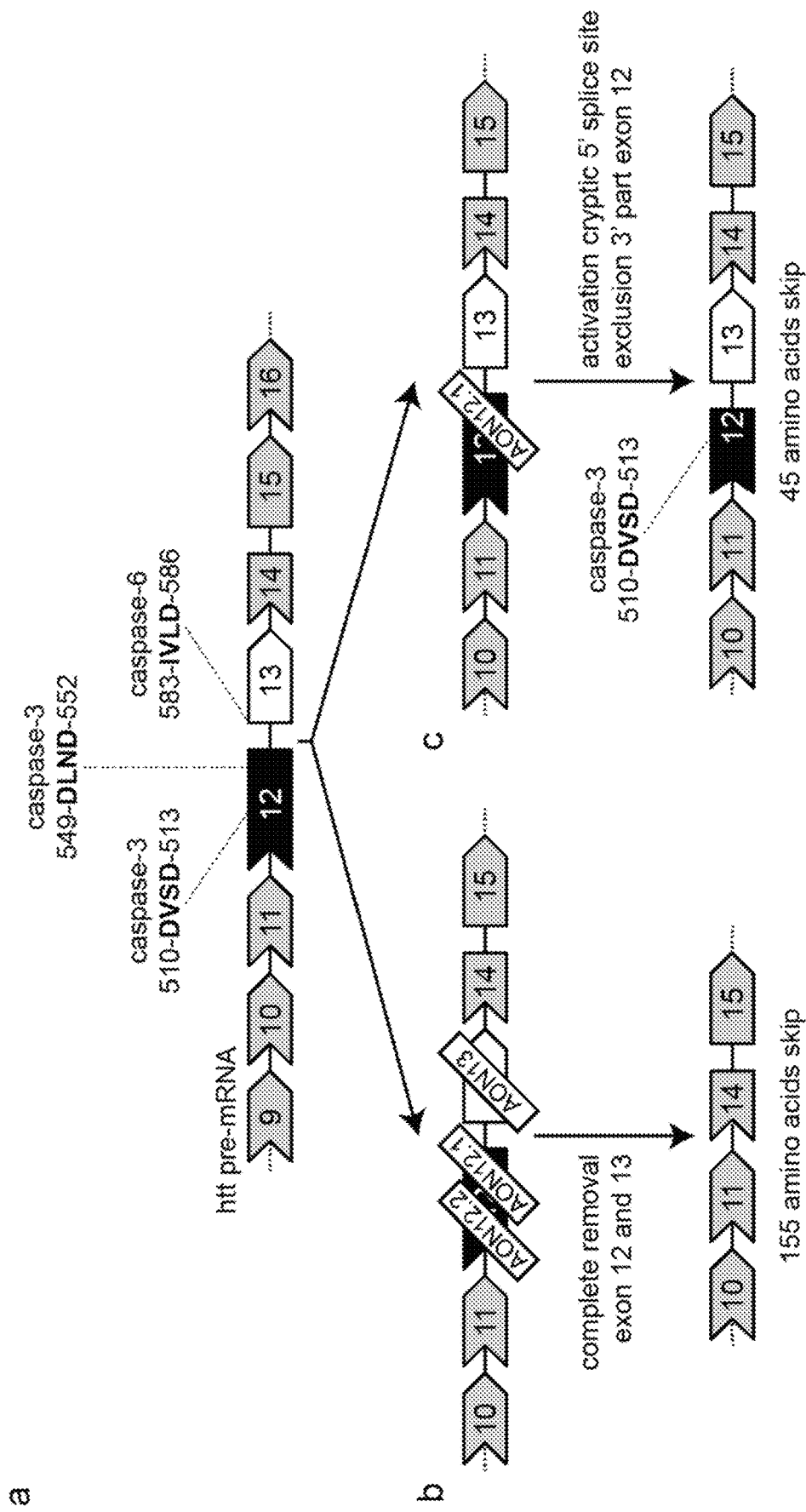
FIG. 6: Schematic representation of caspase motif hotspot in the htt protein and the skipping of exon 12 and 13. (Panel a) The active caspase-6 site at amino acid position 586 (IVLD) is encoded by the last 3 nucleotides of exon 12 and the first 9 nucleotides of exon 13. Exon 12 also encodes two active caspase-3 sites at amino acids 513 (DSVD) and 552 (DLND). (Panel b) To remove all three proteolytic cleavage sites from the htt protein, both exon 12 and 13 have to be skipped by using 3 AONs. (Panel c) AON12.1 targets a region in the 3' part of htt exon 12. This results in the activation of a 5' cryptic splice site and an in-frame exclusion of the 3' part of exon 12. The resulting protein lacks the caspase-3 site at amino acid 552 (DLND), and the isoleucine (I) of the active caspase-6 site at amino acid 586 (IVLD) is replaced by a glutamine (Q).

The caspase-6 site at amino acid position 586 previously shown to be important in disease pathology is encoded partly in exon 12 and partly in exon 13. Exon 12 also encodes two active caspase-3 sites at amino acids 513 and 552 (10, 33). Skipping of both exon 12 and 13 would maintain the open reading frame and therefore is anticipated to generate a shorter htt protein lacking these 3 caspase sites (see FIG. 6). The AONs used in this study are shown below.
AON Name Sequence (5'-3'):

| AON Name | Sequence | SEQ ID NO |
|---|---|---|
| hHTTEx12_7 | GUCCCAUCAUUCAGGUCCAU | 182 |
| hHTTEx12_5 | CUCAAGAUAUCCUCCUCAUC | 178 |
| hHTTEx13_1 | GGCUGUCCAAUCUGCAGG | 190 |
| Control AON | UCCUUUCAUCUCUGGGCUC | 238 |
| mAON12.1 | GGCUCAAGAUGUCCUCCUCAUCC | 239 |
| mAON12.2 | UUUCAGAACUGUCCGAAGGAGUC | 240 |
| mAON13 | GGCUGUCCUAUCUGCAUG | 241 |
| Scrambled AON | CUGAACUGGUCUACAGCUC | 242 |
| Alexa488 AON | GGUACACCUAGCGGAACAAU | 243 |

AONs were transfected in human fibroblasts, total RNA was isolated after 24 hours and cDNA was amplified using htt primers flanking the skipped exons to examine skipping efficiencies. When transfected individually, none of the AONs induced exon 12 skipping. A complete exon 12 skip of 341 base pairs could be achieved by combining two AONs (hHTTEx12_7 and hHTTEx12_5). The most efficient complete exon 12 skip of 30.9% (±0.3%) was achieved by transfecting 100 nM of each hHTTEx12_7 and hHTTEx12_5 (FIG. 7, Panel a).

Figure 7:
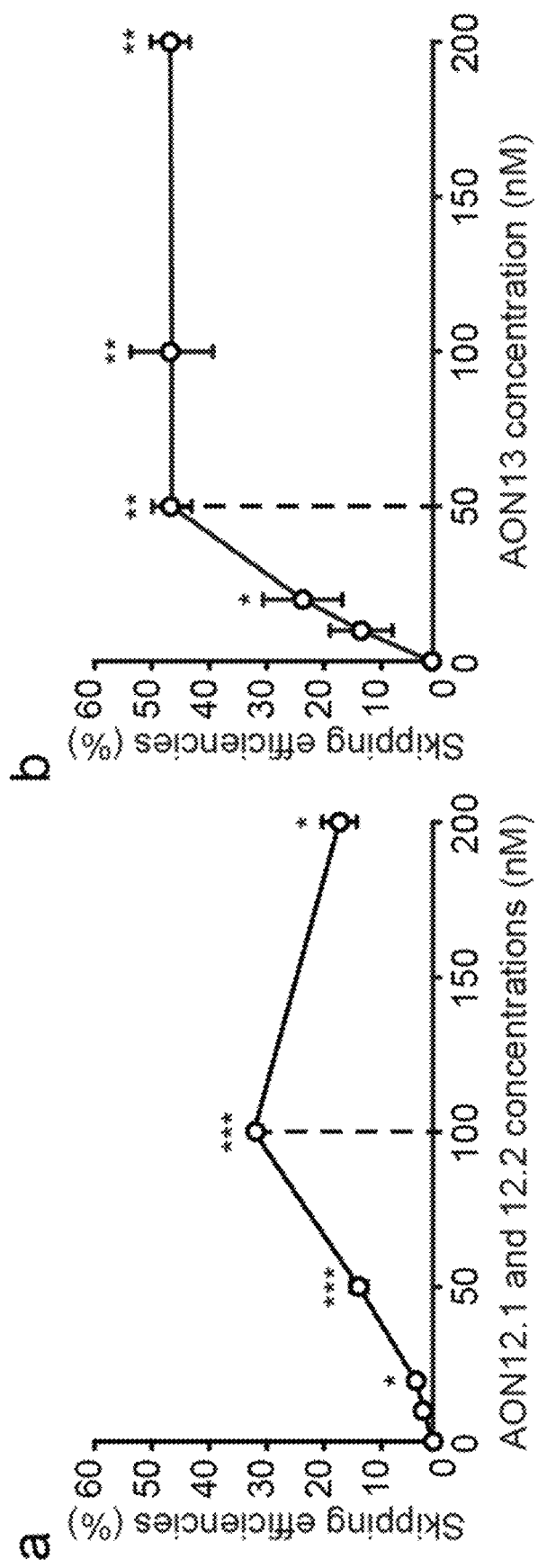
FIG. 7: Optimal AON concentrations. Human fibroblasts were transfected with concentrations ranging from 10 to 200 nM per htt AON. RNA was isolated after 24 hours and Lab-on-a-Chip analysis was performed to calculate exon skip levels for AON12.1 and AON12.2 combined (Panel a), and AON13 (Panel b). (* P<0.05,  P<0.01, * P<0.001, n=4).
Figure 8:
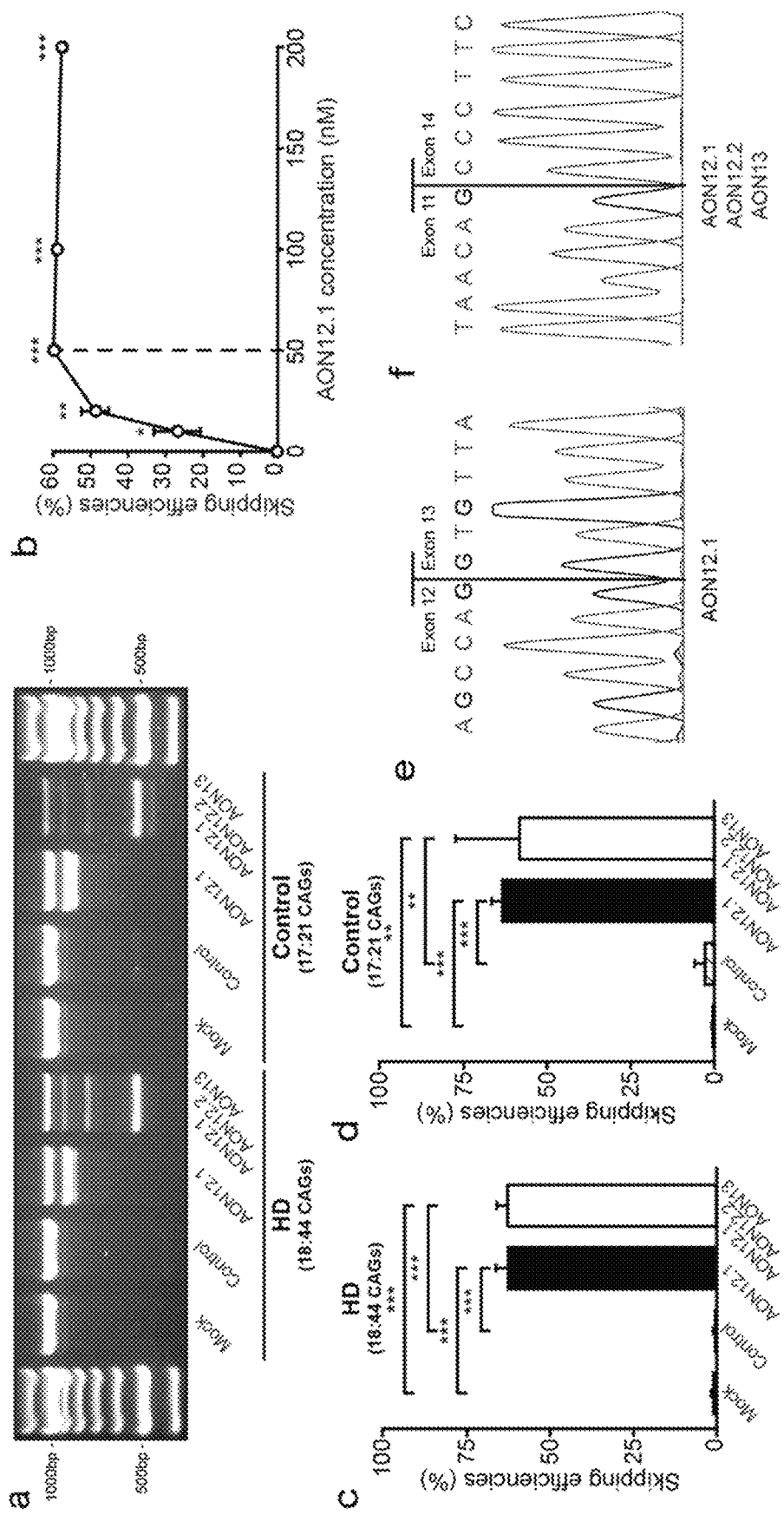
FIG. 8: Transfection to induce double and single exon skipping. Control and HD patient fibroblasts were transfected with htt AONs, control AON, and non-transfected cells (Mock) and RNA was isolated after 24 hours. (Panel a) Agarose gel analysis of the htt transcript with primers flanking exon 12 and 13. Transfection with 100 nM per AON resulted in a product lacking both exon 12 and 13 (AON12.1+12.2+13) or a shorter than expected PCR product after transfection with 100 nM AON12.1, lacking the 3' part of exon 12. (Panel b) Lab-on-a-Chip analysis was performed to calculate partial exon 12 skip levels in control cells transfected with AON12.1 concentrations ranging from 10 to 200 nM. (Panel c) Skip efficiencies determined by Lab-on-a-Chip after 50 nM AON treatment in HD cells. (Panel d) Skip efficiencies determined by Lab-on-a-Chip after 50 nM AON treatment in control cells. Both partial skip (AON12.1) and full skip percentages (AON12.1, AON12.2, and AON13) are shown in Panels c and d ( P<0.01, * P<0.001, n=4). Partial skip (AON12.1) (Panel e) (SEQ ID NO:249) and full skip (AON12.1, AON12.2, and AON13) (Panel f) (SEQ ID NO:250) confirmed by Sanger sequencing.

Skipping efficiency of htt exon 13 by hHTTEx13_1 was (45.2%±3.4%) at a concentration of 50 nM (FIG. 7, Panel b). Skipped products were confirmed by Sanger sequencing. With a full skip of both exon 12 and 13 the mRNA reading frame is maintained. With a combination of three AONs, an efficient skip of htt exon 12 and exon 13 was achieved. This resulted in a skip of 465 base pairs (FIG. 8, Panel a) that was confirmed by Sanger sequencing (FIG. 8, Panel f). The efficiency of this double skip was 62.4% (±3.2%) and 58.0% (±19.1%) in HD and control cells, respectively (FIG. 8, Panels c and d). Partial exon 12 skipping results in a shorter htt protein resistant to caspase 6 cleavage. Interestingly, hHTTEx12_7, targeting the 3' part of exon 12 resulted in a partial skip of exon 12 of 135 base pairs (FIG. 8, Panel a) that was confirmed by Sanger sequencing (FIG. 8, Panel e). The highest skipping percentage of hHTTEx12_7 in control cells was 59.9% (±0.7%) at a concentration of 50 nM (FIG. 8, Panel b). The efficiency of this partial skip in HD cells was 62.2% (±3.6%) (FIG. 8C). This partial exclusion of the 3' part of htt exon 12 can be explained by activation of a cryptic 5' splice site present within exon 12 (AG|GTCAG) (positions 6-12 of SEQ ID NO:228).

Figure 9:
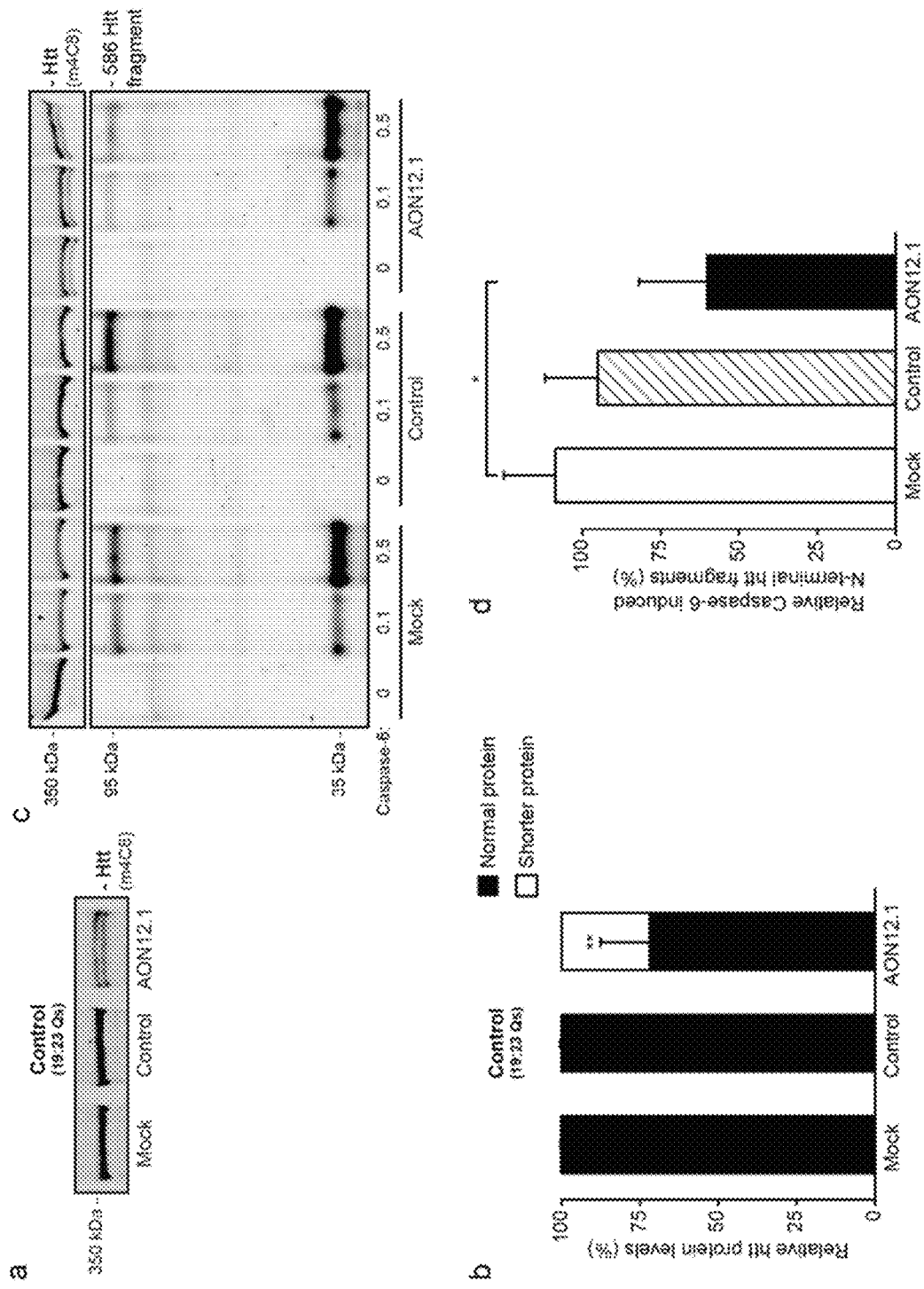
FIG. 9: Formation of modified htt protein after partial exon 12 skipping that is resistant to caspase-6 cleavage. Human control fibroblasts were transfected with 50 nM AON12.1 and control AONs. (Panel a) Transfection with AON12.1 resulted in the appearance of a htt protein that is shorter than the full length protein and runs around 343 kDa. (Panel b) Levels of normal (black bars) and shorter (white bar) htt protein after transfection with AON12.1 determined by Odyssey software quantification (** P<0.01, n=6). (Panel c) In vitro caspase-6 cleavage assay shows a 586 amino acids N-terminal htt fragment appearance of 95 kDa that increases with increasing concentration of caspase-6. In samples from cells treated with AON12.1 this N-terminal htt fragment of 95 kDa is reduced, while an unrelated caspase-6 fragment at 35 kDa remains unchanged. (Panel d) Quantification of Panel c, determined by Odyssey software, using the 35 kDa caspase-6 fragment as reference (* P<0.05, n=4).

Western blot analysis using the 4C8 antibody indeed revealed an additional band of approximately 343 kDa after transfection with hHTTEx12_7 (FIG. 9, Panel a). The 5 kDa shorter htt protein is in concordance with the calculated 45 amino acid skip after AON12.1 transfection. This shorter htt protein represents 27.9% (±15.1%) of total htt protein levels (FIG. 9, Panel b).

To test if the modified htt protein was resistant to caspase-6 cleavage at amino acid position 586, an in vitro caspase-6 assay was performed. Protein was isolated from human fibroblasts three days after treatment with 50 nM of hHTTEx12_7. Htt protein fragments were detected by Western blotting using the 4C8 antibody. After samples were incubated with recombinant active caspase-6, N-terminal htt fragments of 98 kDa were detected (FIG. 9, Panel c). Previous studies showed that these fragments are involved in neuronal dysfunction and neurodegeneration in HD. Samples treated with hHTTEx12_7 resulted in a 31.9% (±21.5%) reduction of these 98 kDa htt fragments, while the shorter htt fragment of 35 kDa, which is not cleaved at amino acid 586, remained unchanged (FIG. 9, Panel d). This shows that mutating the first amino acid of the 586 amino acid caspase-6 motif is sufficient to prevent proteolytic cleavage.

Figure 10:
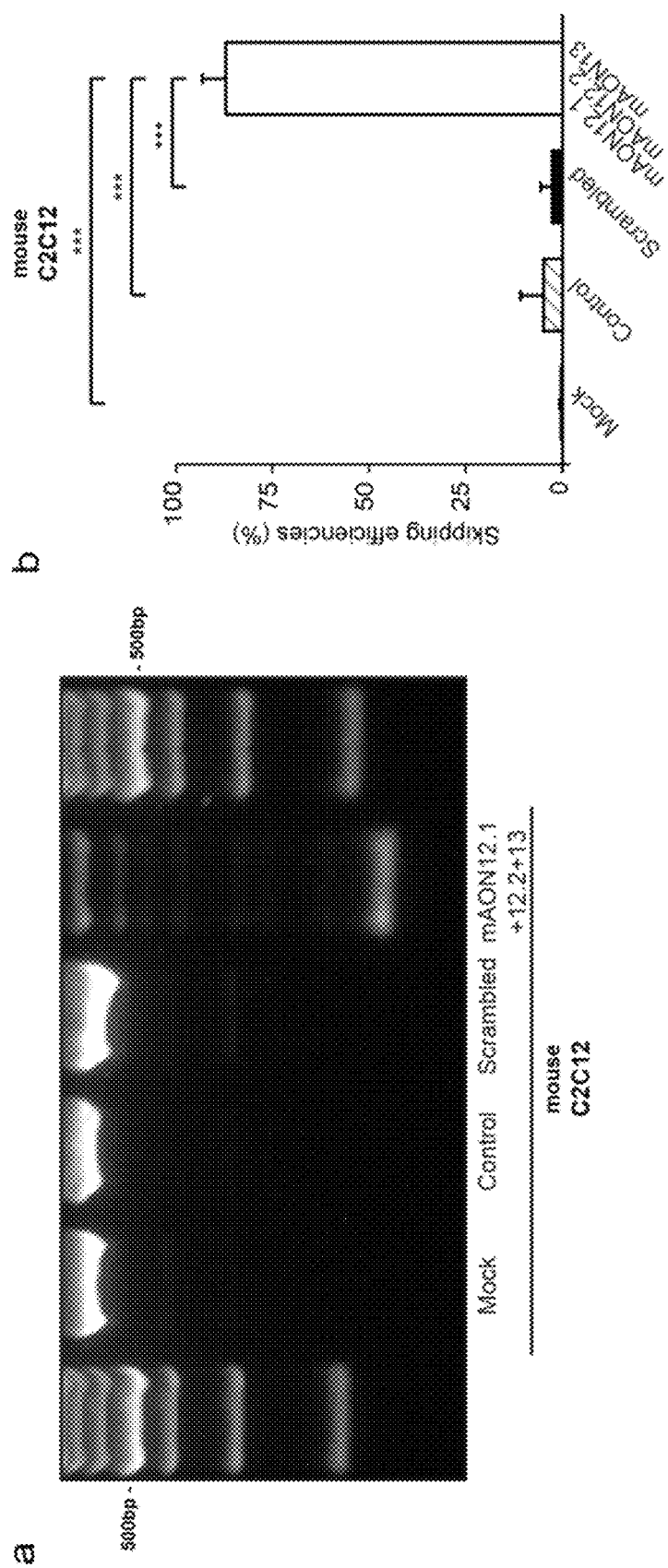
FIG. 10: Skipping murine htt exon 12 and 13 in vitro. Mouse C2C12 cells were transfected with murine htt AONs, control AON, scrambled AON, and not transfected (Mock). (Panel a) Agarose gel analysis of the htt transcript with primers flanking exon 12 and 13. Skipping of htt exon 12 and 13 is seen after transfection with mAON12.1, mAON12.2, and mAON13. (Panel b) Lab-on-a-Chip analysis of double-exon skipping after AON treatment (*** P<0.001, n=4).

Example 3: Removal of the 586 Caspase-6 Cleavage Site from Mouse Htt Protein In Vitro and In Vivo To investigate the potential of htt exon skipping in vivo and to test if removal of the amino acid sequence surrounding the 586 caspase-6 cleavage site could be harmful in vivo, AONs homologues to the mouse sequence was designed. Since mice do not exhibit the cryptic splice site that is responsible for the partial skip in human cells, the full skip of exon 12 and 13 as was described for the human cells was investigated. Transfection of 200 nM of each mouse specific htt AON targeting exon 12 and 13 in mouse C2C12 cells showed a skip of both exons with an efficiency of 86.8% (±5.6) (FIG. 10, Panels a and b).

Figure 11:
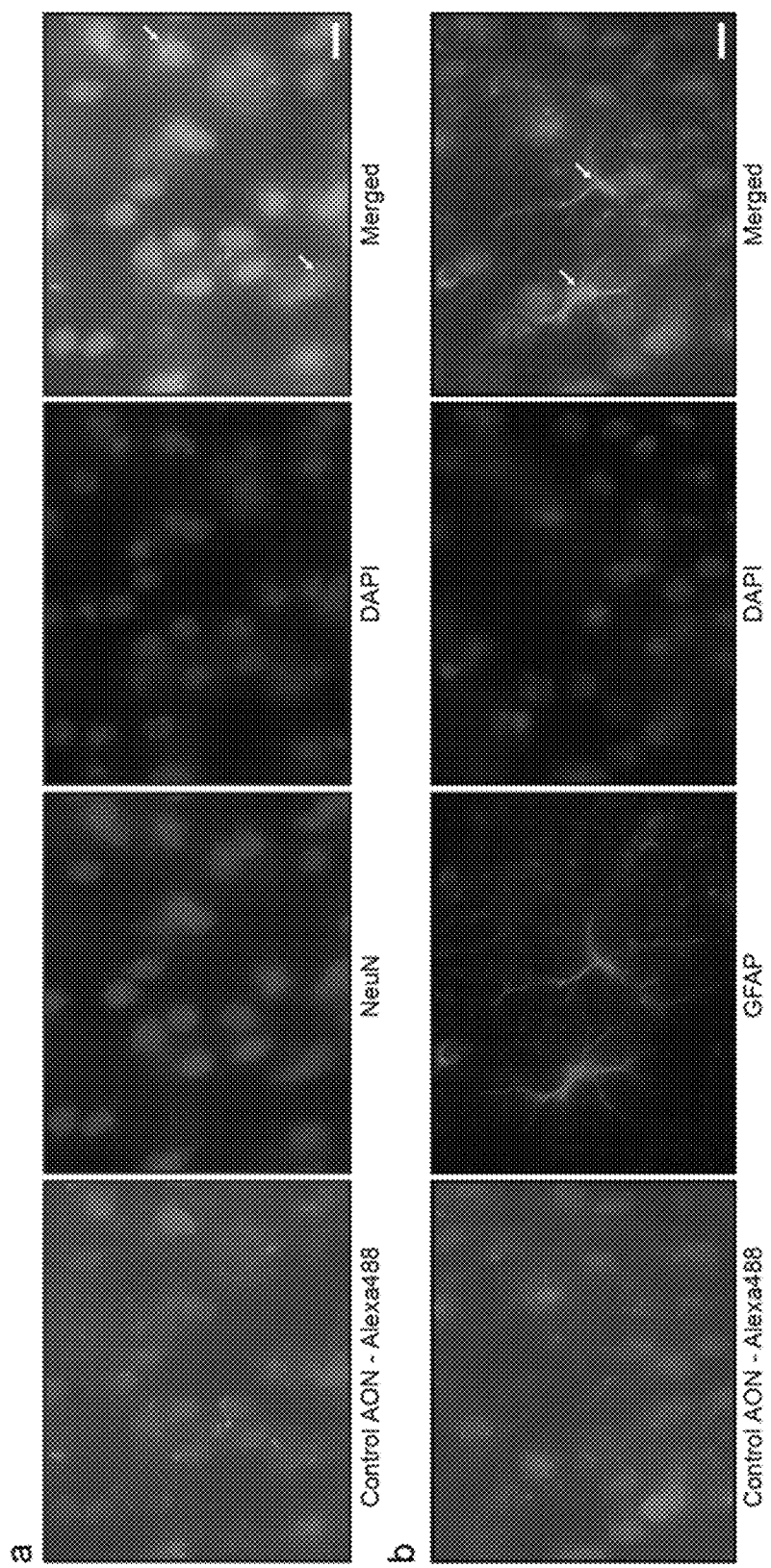
FIG. 11: A single bilateral injection of Alexa488 AON into the striatum resulted in widespread distribution in the mouse midbrain. AON-Alexa488 is shown in green. NeuN (Panel a) and GFAP (Panel b) are shown in red. Nuclei were counterstained with DAPI as shown in blue. Scale bar=10 µm.

To investigate distribution of the AON in the mouse brain, 10 µg of Alexa Fluor 488 labeled control AON was injected bilaterally into the striatum of a control mouse. The mouse was sacrificed after one week, the brain was perfused, and sections were immunolabeled using the neuronal marker NeuN and astrocyte marker glial fibrillary acidic protein (GFAP). Examination under the fluorescence microscope showed AON distribution throughout the midbrain in both astrocytes and neuronal cells (see FIG. 11, Panels a and b).

Figure 12:
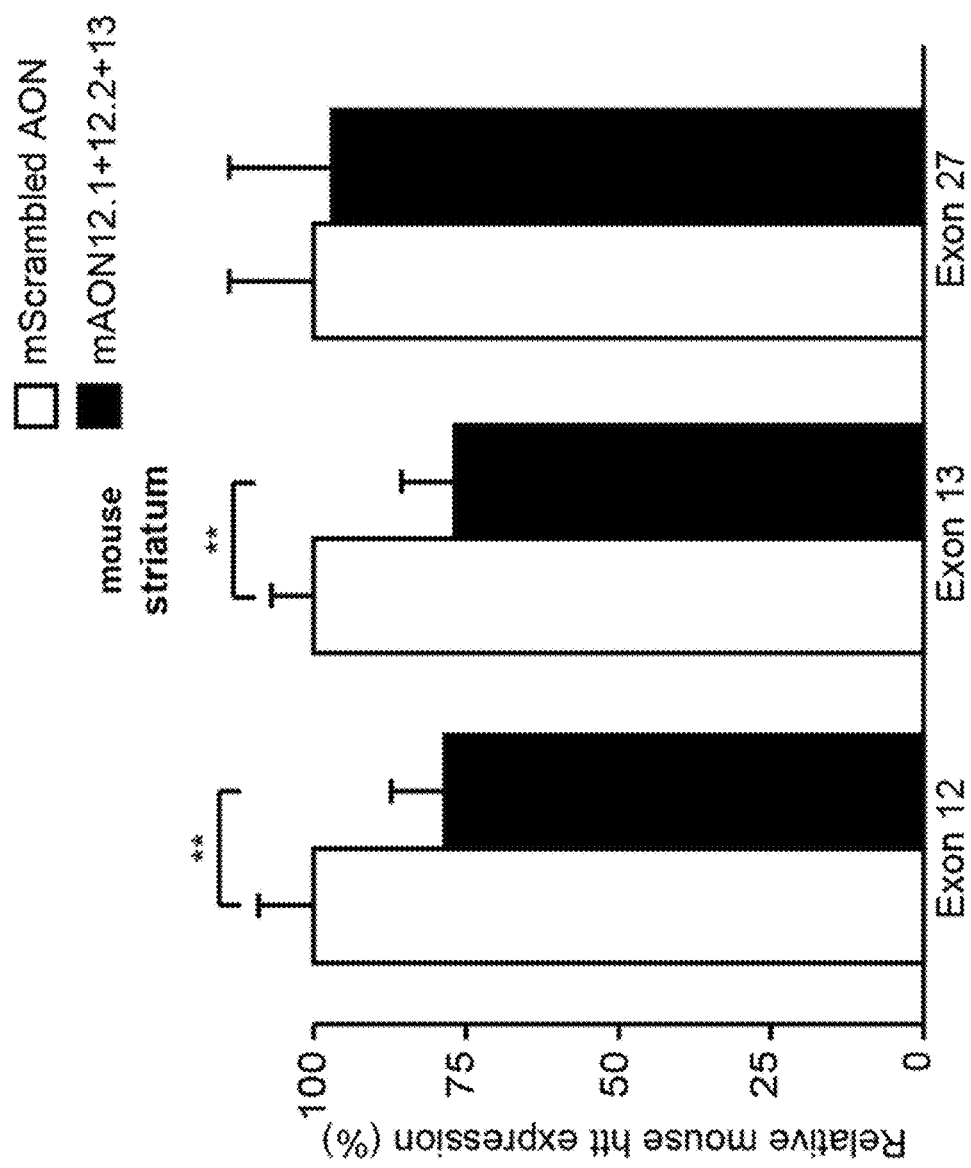
FIG. 12: Reduction of mouse htt exon 12 and 13 after a single local injection into the mouse striatum. A single injection consisting of mAON12.1, mAON12.2 and mAON13 (10 g each) or 30 g scrambled AON was injected bilaterally into the mouse striatum. After seven days, the mice were sacrificed and the presence of exon 12, 13 and 27 in the htt transcript was examined by qRT-PCR. (** P<0.01, n=5).

Next, a single dose of 30 µg scrambled AON or 30 µg AON mix (10 µg per AON) was injected bilaterally into the mouse striatum. After seven days, the mice were sacrificed and expression levels of exon 12 and 13 in the mouse htt transcript were assessed by qRT-PCR (FIG. 12). Exon 12 was significantly reduced by 21.5% (±8.5%) and exon 13 was significantly reduced by 23.1% (±8.3%). Exon 27, downstream of the area targeted for skipping, was not reduced showing that a single intrastriatal administration of AONs already resulted in a skip of htt exon 12 and 13.

Material and Methods
In Vivo Injection into Mice

Mouse htt specific AONs (mAON12.1, mAON12.2, and mAON13) and scrambled control AONs were injected in anesthetized C57bl/6j male mice between the ages of 12 and 14 weeks (Janvier SAS, France). Animals were singly housed in individually ventilated cages (IVC) at a 12 hour light cycle with lights on at 7 a.m. Food and water were available ad libitum. Animals were anesthetized with a cocktail of Hypnorm-Dormicum-demineralized water in a volume ratio of 1.33:1:3. The depth of anesthesia was confirmed by examining the paw and tail reflexes. When mice were deeply anesthetized they were mounted on a Kopf stereotact (David Kopf instruments, Tujunga, USA). A total of 30 µg AON mix diluted in 2.5 µl sterile saline was bilaterally injected at the exact locations 0.50 mm frontal from bregma, ±2.0 mm medio-lateral, and -3.5 mm dorso-ventral. For injections, customized borosilicate glass microcapillary tips of approximately 100 µm in diameter, connected to a Hamilton needle (5 µl, 30 gauge) were used. The Hamilton syringe was connected to an injection pump (Harvard apparatus, Holliston, Mass., USA) which controlled the injection rate set at 0.5 µl/minute. After surgery the animals were returned to the home cage and remained undisturbed until sacrifice, with the exception of daily weighing in order to monitor their recovery from surgery. After seven days, the mice were sacrificed by intraperitoneal injection of overdose Euthasol (ASTfarma, Oudewater, the Netherlands) and brain tissue isolated and snap frozen till further analysis. To determine AON distribution, two mice were injected with 10 g of Alexa Fluor 488 labeled control AON. After seven days, the mice were sacrificed, perfused and brain isolated and frozen till further analysis.

Immunohistochemistry on Mouse Brain Sections

To assess AON distribution, brains were removed and post fixated overnight in 4% paraformaldehyde (PFA) (Sigma, St. Louis, USA) in PBS at 4° C. Subsequently they were cryoprotected in 15% and 30% sucrose in PBS, snap frozen on dry ice and stored at −80° C. Brains were cut into 30 m sections on a Leica cryostat and sections stored in 0.1% sodium azide in PBS. Sections were stained free floating and after three washes in PBS containing 0.2% TRITON® X-100 (PBS-Triton) were incubated overnight at 4° C. with mouse anti-NeuN (Millipore) or rabbit anti-GFAP (Sigma), both diluted 1:5000 in PBS-Triton with 1% normal goat serum and 0.4% Thimerosal (Sigma). Next, sections were washed, incubated for three hours with rabbit anti-Alexa594 (Invitrogen Life Technologies). After three more washes, sections were mounted on glass slides with a DAPI/DABCO solution and examined on a Leica confocal microscope.

Calculations and Statistical Analysis

RNA and protein skipping percentages were calculated using the following formula: Skipping %=(Molarity skipped product/(Total molarity full length product+skipped product))*100%. The 95 kDa N-terminal htt fragment levels were calculated using the 35 kDa caspase-6 fragment as reference. The skipping percentages were analyzed using a paired two-sided Student t test. Differences were considered significant when P<0.05.

Example 4: AON Mediated Skipping of Ataxin-3 Exon 9 and 10 In Vitro

Figure 13:
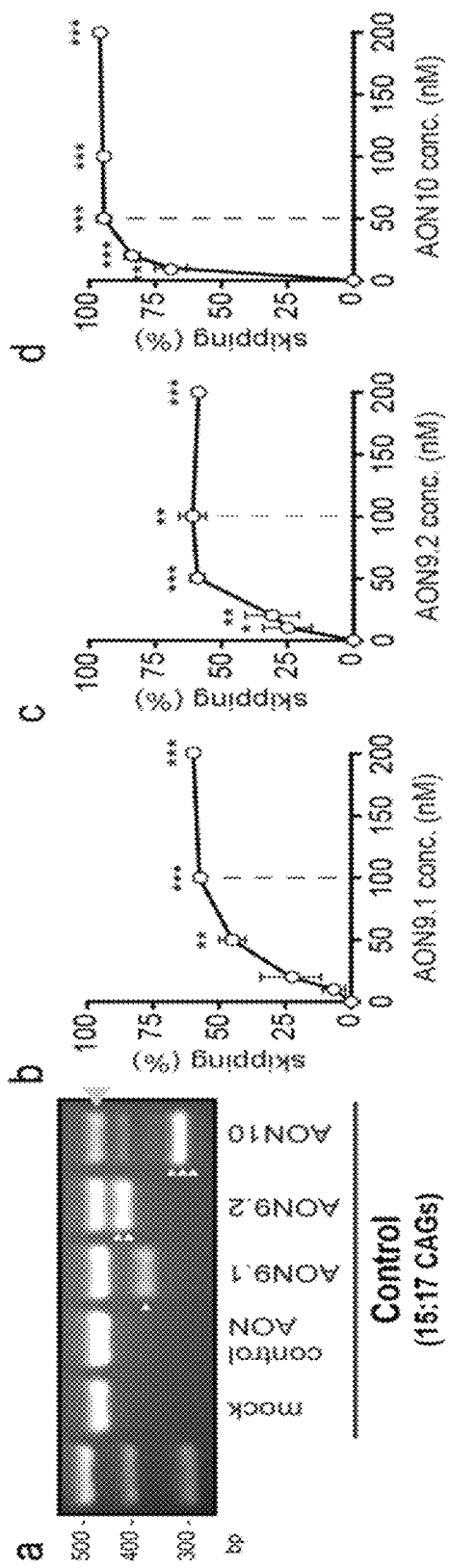
FIG. 13: Single exon skipping of ataxin-3 pre-mRNA in vitro. Control fibroblasts were transfected with ataxin-3 AONs, control AON, and non-transfected (mock) and RNA was isolated after 24 hours. (Panel a) Agarose gel analysis of the ataxin-3 transcript with primers flanking exon 9 and 10 (full-length, grey arrowhead). Transfection with 50 nM AON against exon 9 resulted in a product lacking the entire exon 9 (AON9.1, white arrowhead) or lacking the 3' part of exon 9 (AON9.2, two white arrowheads). Transfection with 50 nM AON10 resulted in a product lacking exon 10 (three white arrowheads). Fibroblasts were transfected with concentrations ranging from 10 to 200 nM per ataxin-3 AON and Lab-on-a-Chip analysis was performed to calculate exon skip levels for (Panel b) AON9.1, (Panel c) AON9.2, and (Panel d) AON10. Mean±SD, data were evaluated using paired student t-test, * P<0.05,  P<0.01, * P<0.001, relative to mock transfection, n=4.
Figure 14:
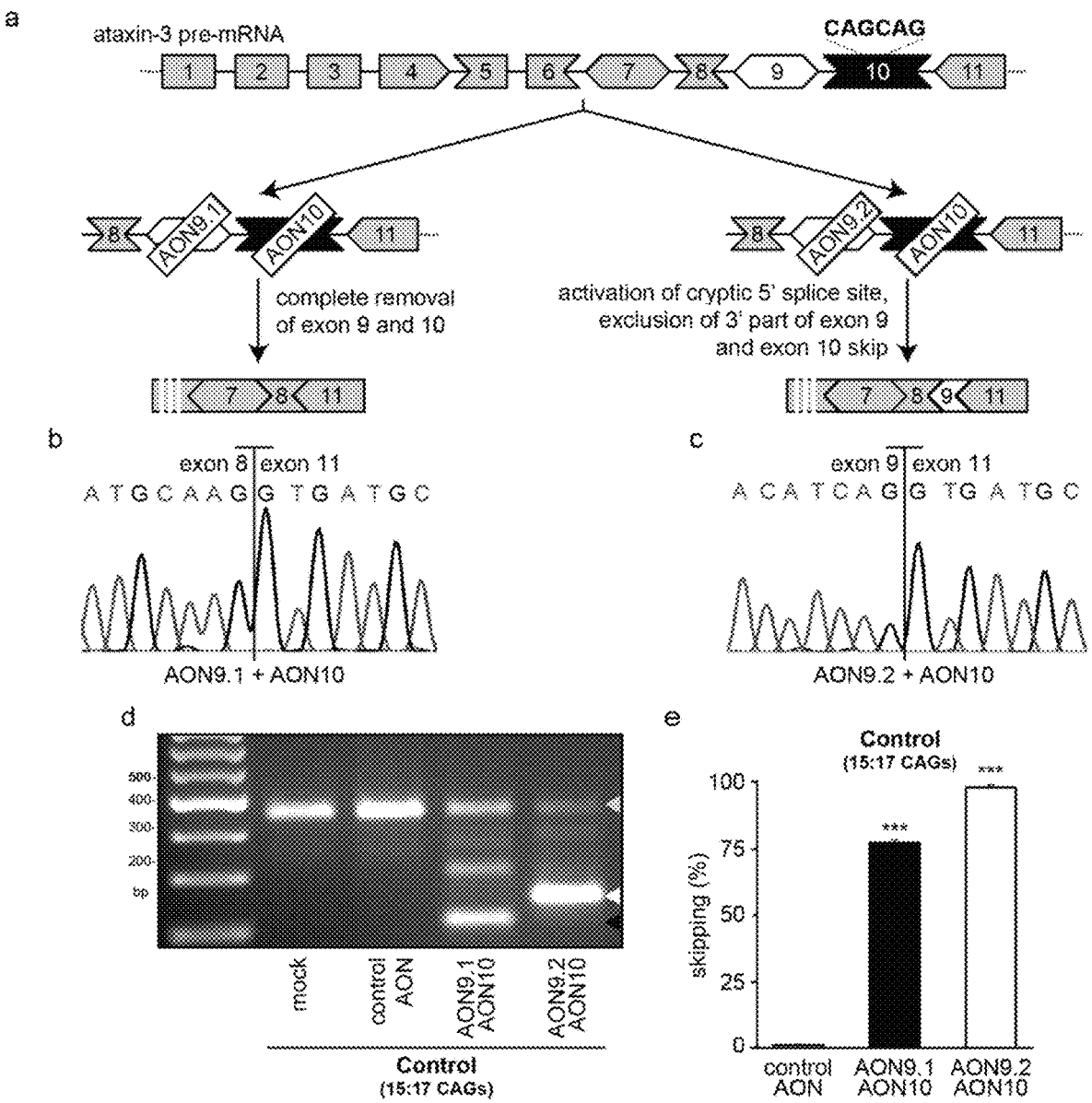
FIG. 14: Double exon skipping of ataxin-3 pre-mRNA in vitro. (Panel a) Schematic representation of two approaches to induce in-frame skipping of the CAG repeat-containing exon. (Panel b) Skip of exon 9 and 10 (AON9.1+AON10) (SEQ ID NO:251) confirmed by Sanger sequencing. (Panel c) Partial skip of exon 9 and complete skip of exon 10 (AON9.2+AON10) (SEQ ID NO:252) confirmed by Sanger sequencing. (Panel d) Agarose gel analysis of the ataxin-3 transcript with primers flanking exon 9 and 10. Transfection of control fibroblasts resulted in a product lacking both exon 9 and 10 (AON9.1+AON10, black arrowhead) or lacking the 3' part of exon 9 and exon 10 (AON9.2+AON10, white arrowhead). (Panel e) Lab-on-a-Chip analysis was performed to calculate exon skip levels in control cells. Mean+SD, data were evaluated using paired student t-test,  P<0.01, * P<0.001, relative to mock, n=4.

The CAG repeat in the ATXN3 gene is located in exon 10, which is 119 nucleotides in length. Thus skipping will disrupt the reading frame. To preserve the reading frame exon 9 (97 nucleotides) and 10 need to be skipped simultaneously (FIG. 14, Panel a). Various AONs were designed targeting exon internal sequences of ataxin-3 exon 9 and 10 and transfected in human fibroblasts (Table 1). PCR analysis revealed a 97 nucleotide skip after transfection with 100 nM of AON9.1 (efficiency=59.2%±1.0%) (FIG. 13, Panels a and b). Sanger sequencing confirmed that this was a skip of exon 9. Transfection with 100 nM AON9.2 resulted in a skip of 55 nucleotides (efficiency=62.3%±3.7%) instead of the anticipated 97 nucleotides (FIG. 13, Panels a and c). Sanger sequencing revealed that this fragment was a partial skip product that still contained the 5' part of exon 9. In silico analysis showed the existence of a cryptic 5' splice site AGIGTCCA in exon 9 that could explain the occurrence of this shorter fragment[24]. Successful skipping of exon 10 was achieved with 50 nM AON10 (efficiency=96.3%±0.3%) (FIG. 13, Panels a and d), as confirmed by Sanger sequencing.

Co-transfection of AON9.1 and AON10 and AON9.2 and AON10 resulted in a skip of respectively 216 and 174 nucleotides (FIG. 14, Panels b and c). The efficiency of the AON9.1 and AON10 induced double skip was 77.0% (±0.9%) in control fibroblasts (FIG. 14, Panels d and e). The efficiency of AON9.2 and AON10 co-transfection was 97.8% (±0.8%) in control fibroblasts (FIG. 14, Panels d and e). The unexpected in-frame partial skip of exon 9 with AON9.2 resulted in an alternative approach to remove the CAG repeat containing exon from the ataxin-3 protein (FIG. 14, Panels a-e).

Modified Ataxin-3 Protein Maintains its Ubiquitin Binding Capacity

To investigate if AON transfection resulted in a modified ataxin-3 protein, control and SCA3 fibroblasts were transfected with AONs targeting exon 9 and 10 and protein was isolated three days after transfection. No negative effect was seen on cell viability after AON treatment in either control or SCA3 fibroblasts. Western blot analysis using an ataxin-3-specific antibody revealed a modified band of approximately 35 kDa after the complete skip of exon 9 and 10 (ataxin-3 Δ72aa) (FIG. 15, Panel a); 11.4% (±5.1%) and 6.2% (±1.9%) of total ataxin-3 protein levels consisted of this modified ataxin-3 Δ72aa protein in, respectively, control and SCA3 fibroblasts (FIG. 15, Panels b and c).

Figure 15:
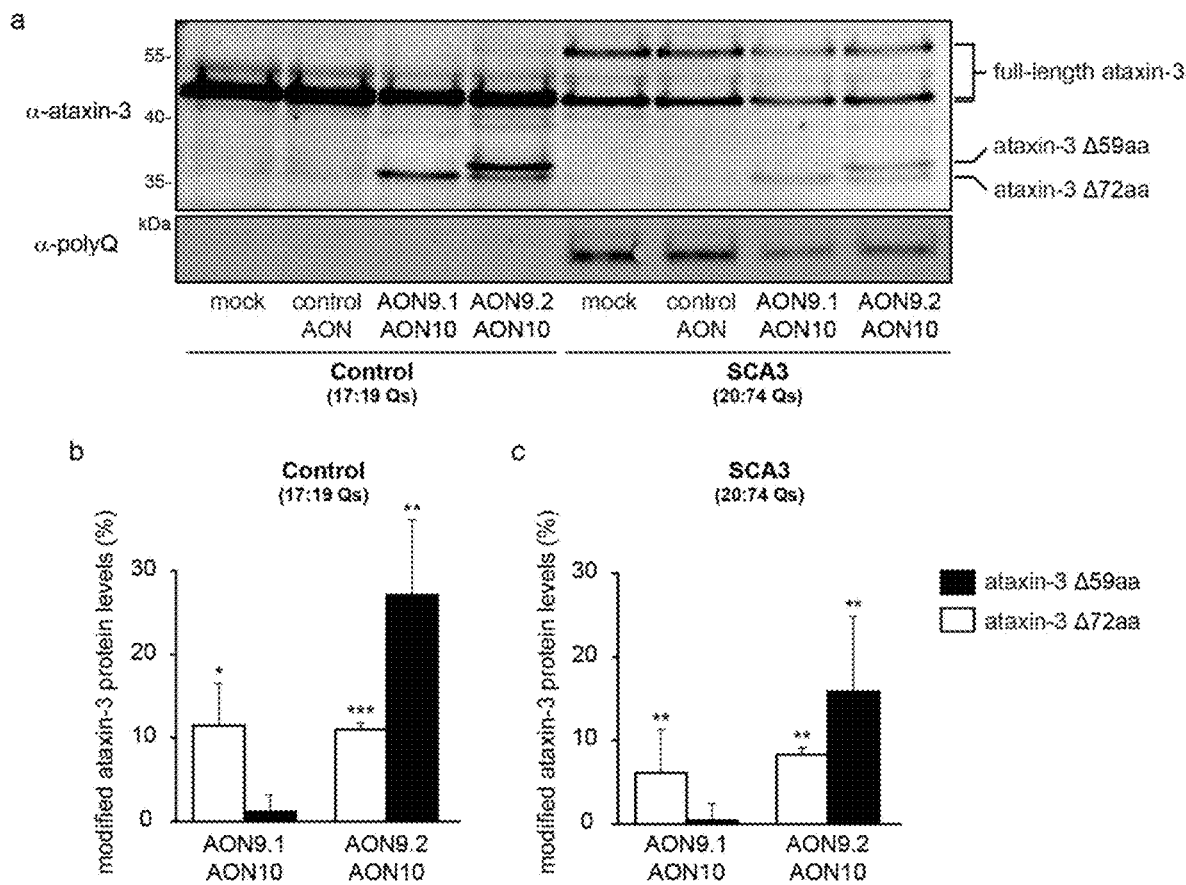
FIG. 15: Modified ataxin-3 protein after exon 9 and 10 skipping. Human control and SCA3 fibroblasts were transfected with 50 nM of each AON. (Panel a) Transfection with AON9.1 and AON10, or AON9.2 and AON10 resulted in modified ataxin-3 proteins of 35 kDa (ataxin-3 Δ72aa) and 37 kDa (ataxin-3 Δ59aa), respectively. The modified protein products were shown using an ataxin-3 specific antibody. The reduction in polyQ-containing mutant ataxin-3 was shown with the polyQ antibody 1C2. Densitometric analysis was used after transfection with AONs. Ataxin-3 Δ72aa (white bars) and ataxin-3 Δ59aa (black bars) in (Panel b) control and (Panel c) SCA3 cells. Mean+SD, data were evaluated using paired student t-test, * P<0.05,  P<0.01, * P<0.001, relative to mock, n=5.

The partial exon skip resulted in a novel 37 kDa protein (ataxin-3 Δ59aa) (FIG. 15, Panel a). 27.1% (±9.0%) and 15.9% (±3.2%) of total ataxin-3 protein levels consisted of this 59 amino acids shorter ataxin-3 protein in, respectively, control and SCA3 cells (FIG. 15, Panels b and c). The ataxin-3 Δ72aa protein was also formed, suggesting that AON9.2 and AON10 transfection also resulted in some ataxin-3 Δ72aa protein. The consistent lower percentage of exon skipping in SCA3 cells were caused by the lower AON transfection efficiencies in the diseased cells as compared to control cells.

A significant reduction in expanded polyQ containing ataxin-3 was shown using the 1C2 antibody that recognizes long glutamine stretches (FIG. 15, Panel a) in the samples with the full and partial exon skip approaches. This indicates a reduction of expanded polyQ-containing ataxin-3 in SCA3 patient derived fibroblasts after AON transfection.

Figure 16:
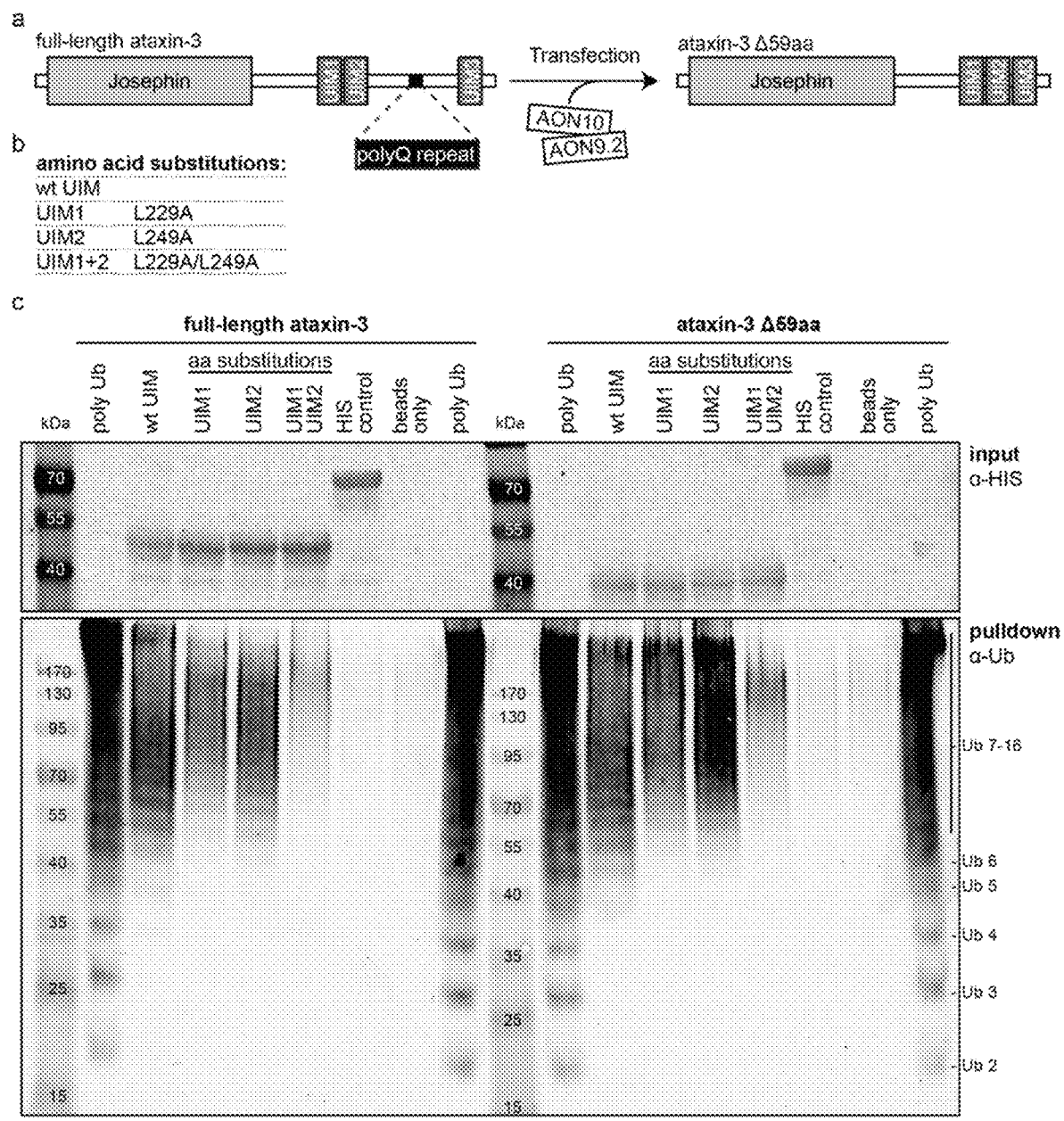
FIG. 16: Full-length and modified ataxin-3 protein displays identical ubiquitin binding. (Panel a) Schematic representation of the known functional domains of the ataxin-3 protein involved in deubiquitination. The ataxin-3 protein consists of an N-terminal (Josephin) domain with ubiquitin protease activity and a C-terminal tail with the polyQ repeat and three ubiquitin interacting motifs (UIMs). After exon skipping (ataxin-3 Δ59aa), the polyQ repeat is removed, leaving the Josephin domain and UIMs intact. (Panel b) Overview of a leucine (L) to alanine (Panel a) substitution in UIM 1 (L229A), UIM 2 (L249A) or both (L229A/L249A) in full-length ataxin-3 and ataxin-3 Δ59aa. (Panel c) Ubiquitin binding assay. HIS-tagged full-length ataxin-3 and ataxin-3 Δ59aa-bound ubiquitylated proteins were analyzed by Western blot. HIS control and beads only were taken along as negative control. The modified ataxin-3 Δ59aa lacking the polyQ repeat showed identical ubiquitylated protein binding as unmodified ataxin-3. (n=3).

The polyQ repeat in the ataxin-3 protein is located between the second and third UIM (FIG. 16, Panel a). Both full and partial exon skip approaches resulted in removal of the polyQ repeat, preserving the Josephin domain, nuclear export signal (NES), and UIMs. To investigate whether the ubiquitin binding capacities of the UIMs in ataxin-3 are still intact after protein modification, poly-ubiquitin chains were incubated with purified cell free produced full-length ataxin-3 and ataxin-3 Δ59aa protein. As negative controls, three different ataxin-3 protein products were produced containing 1 amino acid substitutions from leucine (L) to alanine (A) in UIM 1 (L229A), UIM 2 (L249A), or both (L229A/L249A) (FIG. 4). Single amino acid changes in UIM 1 (L229A) already showed reduced binding of ataxin-3 to poly-ubiquitin chains, whereas double UIM mutated ataxin-3 (L229A/L249A) resulted in a nearly complete elimination poly-ubiquitin binding (FIG. 16, Panel c). The negative HIS control protein did not bind ubiquitylated proteins as expected. Ataxin-3 Δ59aa bound poly-ubiquitin chains comparable to full-length ataxin-3, indicating that its ubiquitin binding capacity after protein modification is still intact (FIG. 16, Panel c).

AON Mediated Skipping of Ataxin-3 Exon 9 and 10 in Mouse

Figure 17:
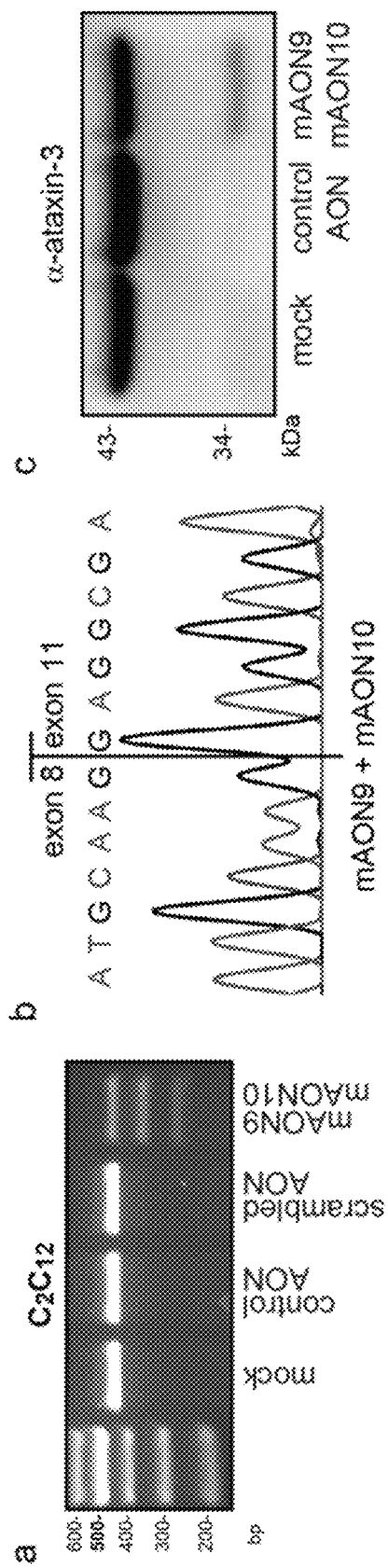
FIG. 17: Double exon skipping of murine ataxin-3 pre-mRNA in vitro. Mouse C2C12 cells were transfected with murine ataxin-3 AONs, control AON, scrambled AON, and not transfected (Mock). (Panel a) Agarose gel analysis of the ataxin-3 transcript with primers flanking exon 9 and 10. Skipping of ataxin-3 exon 9 and 10 was seen after transfection with mAON9.1 and mAON10. (Panel b) Sanger sequencing confirmed the precise skipping of exon 9 and 10 (SEQ ID NO:253). (Panel c) Transfection with mouse AON9.1 and AON10 resulted in the appearance of a modified ataxin-3 protein of 34 kDa.

To examine ataxin-3 exon skipping in the mouse brain and to determine if the modified protein is not harmful, AONs specific to the mouse sequence were designed. Since mice do not exhibit the cryptic splice site that is responsible for the partial exon 9 skip in the human transcript, only the full skip of exon 9 and 10 was investigated. Transfection of 200 nM of each murine AON9 (mAON9) and AON10 (mAON10) in mouse C2C12 cells showed a skip of both exons with an efficiency of 31.7% (±2.4%) (FIG. 17, Panel a). Sanger sequencing confirmed this in-frame double exon skip (FIG. 17, Panel b). Transfection with mAON9 and mAON10 resulted in formation of a modified protein of 34 kDa (FIG. 17, Panel c).

Figure 18:
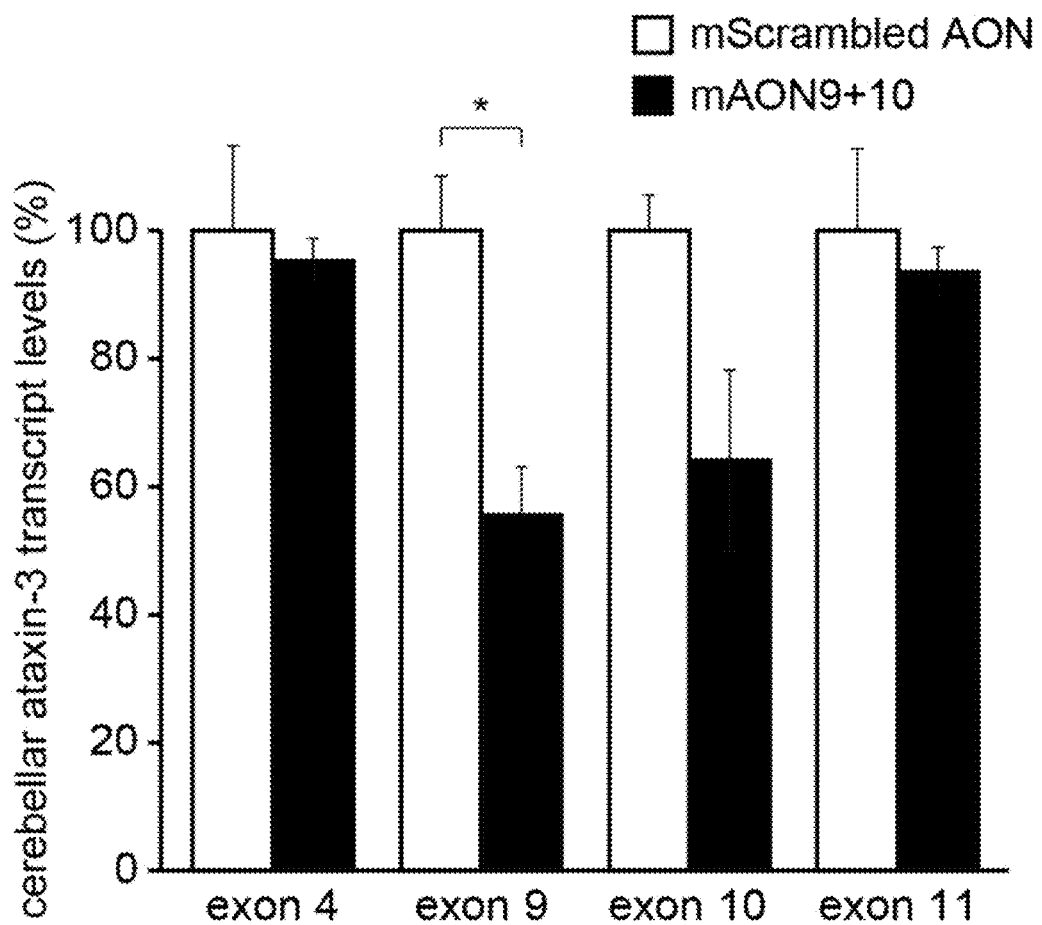
FIG. 18: Reduction of mouse ataxin-3 exon 9 in vivo. Seven days after a single injection consisting of mAON9 and mAON10 (20 g each) into the mouse cerebral ventricle. qRT-PCR analysis of cerebellar tissue showed reduced exon 9 and 10 transcript levels, whereas exon 4 and 11 levels were not affected. Mean+SD, data were evaluated using paired student t-test, * P<0.05, n=3.
Figure 19:
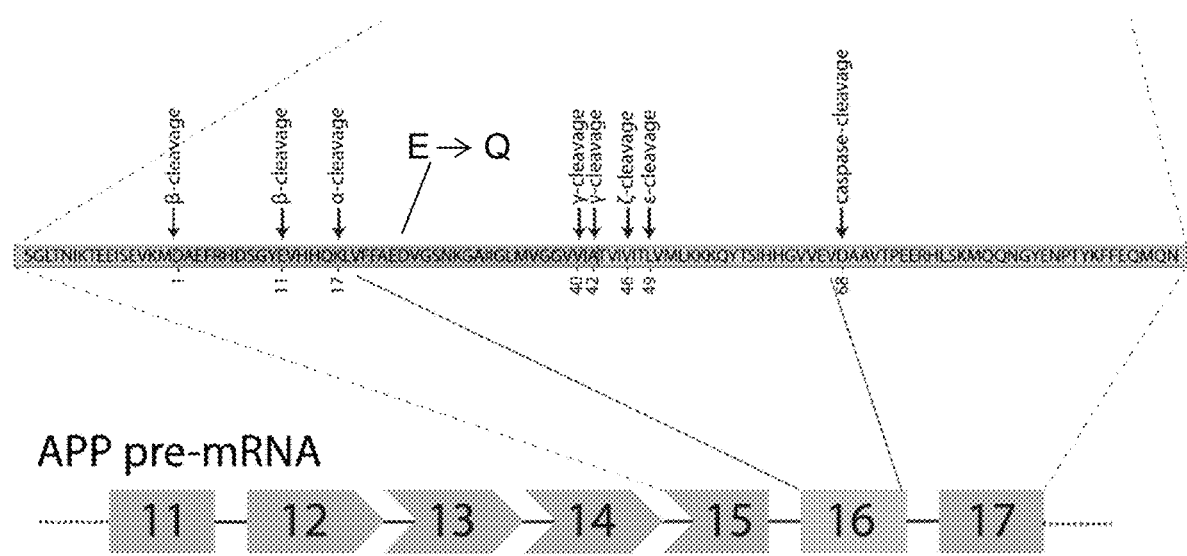
FIG. 19: Schematic of APP pre-mRNA and HCHWA-D mutation. The exon-intron structure of APP751 is depicted in this pre-mRNA schematic representation (SEQ ID NO:254). The shape of the exon-boxes depict the reading frame. The HCHWA-D mutation is located in exon 16 of APP751.

Next, a single intra-cerebral ventricular (ICV) injection was administered of 40 g ataxin-3 AON mix (20 µg per AON) or 40 g scrambled AON. After 7 days, the mice were sacrificed and skipping efficiency in the cerebellum was assessed by qRT-PCR (FIG. 18). Exon 9 was found significantly reduced by 44.5% (±7.6%) and exon 10 was reduced by 35.9% (±14.1%) after a single ICV injection of AONs as compared to scrambled AON. Exon 4, upstream, and exon 11, downstream of the area targeted for skipping were not reduced, demonstrating a specific skip of ataxin-3 exon 9 and 10 in vivo.

In the current study, a novel approach to reduce toxicity of the mutant ataxin-3 protein is shown through skipping of the CAG repeat containing exon in the ataxin-3 transcript. The resulting modified ataxin-3 protein lacks the polyQ repeat that is toxic when expanded, but maintains its ubiquitin binding properties. ICV administration of these AONs in mice resulted in skipping of the CAG repeat-containing exon in the cerebellum of control mice, proving distribution and efficiency of ataxin-3 exon skipping after ICV injection in vivo.

There was no negative effect on cell viability after AON treatment in both control and SCA3 fibroblasts and also no overt toxicity in vivo.

Additional Materials and Methods
Cell Culture and Transfection

Patient derived fibroblasts from SCA3 patients (GM06151, purchased from Coriell Cell Repositories, Camden, USA) and controls (FLB73, a kind gift from Dr. M. P. G. Vreeswijk, LUMC) were cultured at 37° C. and 5% $CO_2$ in Minimal Essential Medium (MEM) (Gibco Invitrogen, Carlsbad, USA) with 15% heat inactivated Fetal Bovine Serum (FBS) (Clontech, Palo Alto, Calif., USA), 1% Glutamax (Gibco) and 100 U/ml penicillin/streptomycin (P/S) (Gibco). Mouse myoblasts $C_2Cl_2$ (ATCC, Teddington, UK) were cultured in Dulbecco's Modified Eagle Medium (DMEM) (Gibco) with 10% FBS, 1% glucose, 2% Glutamax and 100 U/ml P/S.

AON transfection was performed in a six-well plate with 3 µl of Lipofectamine 2000 (Life Technologies, Paisley, UK) per well. AON and Lipofectamine 2000 were diluted in MEM to a total volume of 500 µl and mixtures were prepared according to the manufacturer's instruction. Four different transfection conditions were used: 1) transfection with 1-200 nM AONs, 2) transfection with non-relevant h40AON2 directed against exon 40 of the DMD gene (Control AON)[36], 3) transfection with scrambled AON (Scrambled), and 4) transfection without AON (Mock). For AON sequences, see Table 1. Mixtures were added to a total volume of 1 ml of MEM. Four hours after transfection, medium was replaced with fresh medium containing 5% FBS. All AONs consisted of 2'-O-methyl RNA and contained a full-length phosphorothioate modified backbone (Eurogentec, Liege, Belgium).

TABLE 1

Antisense oligonucleotides sequences used for transfection and injection

| AON Name | Sequence (5' - 3') |
|---|---|
| AON9.1 hATXN3Ex9_1 | GAGAUAUGUUUCUGGAACUACC (SEQ ID NO: 144) |
| AON9.2 hATXN3Ex9_2 | GCUUCUCGUCUCUUCCGAAGC (SEQ ID NO: 146) |
| AON10 hATXN3Ex10_1 | GCUGUUGCUGCUUUUGCUGCUG (SEQ ID NO: 148) |
| Control AON | UCCUUUCAUCUCUGGGCUC (SEQ ID NO: 238) |
| mAON9.1 | GCUUCUCGUCUCCUCCGCAGC (SEQ ID NO: 247) |
| mAON10 | GAACUUGUGGUCGGUCUUUCAC (SEQ ID NO: 248) |
| Scrambled AON | CUGAACUGGUCUACAGCUC (SEQ ID NO: 242) |

TABLE 1a

Polyglutamine (PolyQ) Diseases

| Type | Gene | Normal PolyQ repeats | Pathogenic PolyQ repeats |
|---|---|---|---|
| DRPLA (Dentatorubropallidoluysian atrophy) | ATN1 or DRPLA | 6-35 | 49-88 |
| HD (Huntington's disease) | Htt (Huntingtin) | 10-35 | 35+ |
| SBMA (Spinobulbar muscular atrophy or Kennedy disease) | Androgen receptor on the X chromosome. | 9-36 | 38-62 |

TABLE 1a-continued

Polyglutamine (PolyQ) Diseases

| Type | Gene | Normal PolyQ repeats | Pathogenic PolyQ repeats |
|---|---|---|---|
| SCA1 (Spinocerebellar ataxia Type 1) | ATXN1 | 6-35 | 49-88 |
| SCA2 (Spinocerebellar ataxia Type 2) | ATXN2 | 14-32 | 33-77 |
| SCA3 (Spinocerebellar ataxia Type 3 or Machado-Joseph disease) | ATXN3 | 12-40 | 55-86 |
| SCA6 (Spinocerebellar ataxia Type 6) | CACNA1A | 4-18 | 21-30 |
| SCA7 (Spinocerebellar ataxia Type 7) | ATXN7 | 7-17 | 38-120 |
| SCA17 (Spinocerebellar ataxia Type 17) | TBP | 25-42 | 47-63 |

TABLE 1b

Non-Polyglutamine Diseases
Unstable repeat disorders caused by loss-of-function, RNA-mediated, or unknown mechanism

| Disease | MIM Number | Repeat unit | Gene product | Normal repeat | Expanded repeat | Main clinical features length |
|---|---|---|---|---|---|---|
| *Loss of function mechanism* | | | | | | |
| FRAXA | 309550 | (CGC)$_n$ | FMRP | 6-60 | >200 (full mutation) | Mental retardation, macroorchidsm, connective tissue defects, behavioral abnormalities |
| FRAXE | 309548 | (CCG)$_n$ | FMR2 | 4-39 | 200-900 | Mental retardation |
| FRDA | 229300 | (GAA)$_n$ | Frataxin | 6-32 | 200-1700 | Sensory ataxia, cardiomyopathy, diabetes |
| *RNA-mediated pathogenesis* | | | | | | |
| DM1 | 160900 | (CTG)$_n$ | DMPK | 5-37 | 50-10,000 | Myotonia, weakness, cardiac conduction defects, insulin resistance, cataracts, testicular atrophy, and mental retardation in congenital form |
| FXTAS | 309550 | (CGG)$_n$ | FMR1 RNA | 6-60 | 60-200 (premutation) | Ataxia, tremor, Parkinsonism, and dementia |
| *Unknown pathogenic mechanism* | | | | | | |
| SCA8 | 608768 | (CTG)$_n$ | SCA8 RNA | 16-34 | >74 | Ataxia, slurred speech, nystagmus |
| SCA12 | 604326 | (CAG)$_n$ | PPP2R2B | 7-45 | 55-78 | Ataxia and seizures |
| HDL2 | 606438 | (CTG)$_n$ | Junctophilin | 7-28 | 66-78 | Similar to HD |

*Annual Review of Neuroscience*, Vol. 30: 575-621 (Volume publication date July 2007)
*Trinucleotide Repeat Disorders*, Harry T. Orr and Huda Y. Zoghbi

TABLE 2

List of AON

HDEx12_1: CGGUGGUGGUCUGGGAGCUGUCGCUGAUG
(SEQ ID NO: 1)

HDEx12_2: UCACAGCACACACUGCAGG
(SEQ ID NO: 2)

HDEx13_1: GUUCCUGAAGGCCUCCGAGGCUUCAUCA
(SEQ ID NO: 3)

HDEx13_2: GGUCCUACUUCUACUCCUUCGGUGU
(SEQ ID NO: 4)

HDEx12_2 is a comparative example of an oligonucleotide having the nucleotide sequence of Htt in the sense strand.

DRPLA AONs:

| | | | |
|---|---|---|---|
| 1 | DRPLAEx5_18 | GUC GCU GCU GCC AUC AUC AU | (SEQ ID NO: 5) |
| 2 | DRPLAEx5_128 | AAG AGG AAG CAG GAG GCA GA | (SEQ ID NO: 6) |
| 3 | DRPLAEx5_81 | GGA GGA GCC UGG AAC AUU CG | (SEQ ID NO: 7) |
| 1 | DRPLAEx6_80 | AAG CUC GCG CUC CUU CUC GC | (SEQ ID NO: 8) |
| 2 | DRPLAEx6_1 | CGA GUU GAA GCC GCG AUC CA | (SEQ ID NO: 9) |
| 3 | DRPLAEx6_84 | GUU CAA GCU CGC GCU CCU UC | (SEQ ID NO: 10) |

HDEx AON are oligonucleotides for skipping exons 12 or 13 of the Htt gene.

DRPLA AON are oligonucleotides for skipping exons 5 or 6 of the DRPLA/ATN1 gene.

Table 3 provides further oligonucleotides for exon skipping.

APP: amyloid precursor protein in Alzheimer's disease (AD); ATN1: Atrophin 1 in DRPLA; ATNX3: Ataxin 3 for SCA3; ATXN7: Ataxin 7 in SCA7; TBP: TATA binding protein for SCA17; and HTT in Huntington's disease (HD)

TABLE 3

AON sequences targeting proteins involved in neurodegenerative diseases

| Disease | AON Name | Target Sequence | AON Sequence |
|---|---|---|---|
| AD | hAPPEx15_1 | GTTCTGGGTTGACAAATATCAAG (SEQ ID NO: 11) | CUUGAUAUUUGUCAACCCAGAAC (SEQ ID NO: 12) |
| AD | hAPPEx15_2 | CGGAGGAGATCTCTGAAGTGAAG (SEQ ID NO: 13) | CUUCACUUCAGAGAUCUCCUCCG (SEQ ID NO: 14) |
| AD | hAPPEx15_3 | GATGCAGAATTCCGACATGAC (SEQ ID NO: 15) | GUCAUGUCGGAAUUCUGCAUC (SEQ ID NO: 16) |
| AD | hAPPEx15_4 | CTCAGGATATGAAGTTCATCATC (SEQ ID NO: 17) | GAUGAUGAACUUCAUAUCCUGAG (SEQ ID NO: 18) |
| AD | hAPPEx16_1 | GCAATCATTGGACTCATGGT (SEQ ID NO: 19) | ACCAUGAGUCCAAUGAUUGC (SEQ ID NO: 20) |
| AD | hAPPEx16_2 | GATCGTCATCACCTTGGTGA (SEQ ID NO: 21) | UCACCAAGGUGAUGACGAUC (SEQ ID NO: 22) |
| AD | hAPPEx16_3 | GTACACATCCATTCATCATGGTG (SEQ ID NO: 23) | CACCAUGAUGAAUGGAUGUGUAC (SEQ ID NO: 24) |
| AD | hAPPEx16_4 | GCAGAAGATGTGGGTTCAAAC (SEQ ID NO: 25) | GUUUGAACCCACAUCUUCUGC (SEQ ID NO: 26) |
| AD | hAPPEx16_5 | GGTGATGCTGAAGAAGAAACAG (SEQ ID NO: 27) | CUGUUUCUUCUUCAGCAUCACC (SEQ ID NO: 28) |
| AD | hAPPEx16_6 | TCATCATGGTGTGGTGGAGGTAG (SEQ ID NO: 29) | CUACCUCCACCACACCAUGAUGA (SEQ ID NO: 30) |
| DRPLA | hATN1Ex5_1 | CTCCCTCGGCCACAGTCTCCCT (SEQ ID NO: 31) | AGGGAGACUGUGGCCGAGGGAG (SEQ ID NO: 32) |
| DRPLA | hATN1Ex5_2 | GCGGAGCCTTAATGATGATGGC (SEQ ID NO: 33) | GCCAUCAUCAUUAAGGCUCCGC (SEQ ID NO: 34) |
| DRPLA | hATN1Ex5_3 | AGCAGCGACCCTAGGGATATCG (SEQ ID NO: 35) | CGAUAUCCCUAGGGUCGCUGCU (SEQ ID NO: 36) |
| DRPLA | hATN1Ex5_4 | AGGACAACCGAAGCACGTCCC (SEQ ID NO: 37) | GGGACGUGCUUCGGUUGUCCU (SEQ ID NO: 38) |
| DRPLA | hATN1Ex5_5 | TGGAAGTGTGGAGAATGACTCTG (SEQ ID NO: 39) | CAGAGUCAUUCUCCACACUUCCA (SEQ ID NO: 40) |
| DRPLA | hATN1Ex5_6 | ATCTTCTGGCCTGTCCCAGGGC (SEQ ID NO: 41) | GCCCUGGGACAGGCCAGAAGAU (SEQ ID NO: 42) |
| DRPLA | hATN1Ex5_7 | CGACAGCCAGAGGCTAGCTTTGA (SEQ ID NO: 43) | UCAAAGCUAGCCUCUGGCUGUCG (SEQ ID NO: 44) |
| DRPLA | hATN1Ex5_8 | CTCGAATGTTCCAGGCTCCTCC (SEQ ID NO: 45) | GGAGGAGCCUGGAACAUUCGAG (SEQ ID NO: 46) |
| DRPLA | hATN1Ex5_9 | TCTATCCTGGGGGCACTGGTGG (SEQ ID NO: 47) | CCACCAGUGCCCCCAGGAUAGA (SEQ ID NO: 48) |
| DRPLA | hATN1Ex5_10 | TGGACCCCCAATGGGTCCCAAG (SEQ ID NO: 49) | CUUGGGACCCAUUGGGGGUCCA (SEQ ID NO: 50) |
| DRPLA | hATN1Ex5_11 | AGGGGCTGCCTCATCAGTGG (SEQ ID NO: 51) | CCACUGAUGAGGCAGCCCCU (SEQ ID NO: 52) |

TABLE 3-continued

AON sequences targeting proteins involved in neurodegenerative diseases

| Disease | AON Name | Target Sequence | AON Sequence |
|---|---|---|---|
| DRPLA | hATN1Ex5_12 | AAGCTCTGGGGCTAGTGGTGCTC (SEQ ID NO: 53) | GAGCACCACUAGCCCCAGAGCUU (SEQ ID NO: 54) |
| DRPLA | hATN1Ex5_13 | ACAAAGCCGCCTACCACTCCAG (SEQ ID NO: 55) | CUGGAGUGGUAGGCGGCUUUGU (SEQ ID NO: 56) |
| DRPLA | hATN1Ex5_14 | CTCCACCACCAGCCAACTTCC (SEQ ID NO: 57) | GGAAGUUGGCUGGUGGUGGAG (SEQ ID NO: 58) |
| DRPLA | hATN1Ex5_15 | CCAACCACTACCTGGTCATCTG (SEQ ID NO: 59) | CAGAUGACCAGGUAGUGGUUGG (SEQ ID NO: 60) |
| DRPLA | hATN1Ex5_16 | TGGCCCAGAGAAGGGCCCAAC (SEQ ID NO: 61) | GUUGGGCCCUUCUCUGGGCCA (SEQ ID NO: 62) |
| DRPLA | hATN1Ex5_17 | TTCCTCTTCTGCTCCAGCGCC (SEQ ID NO: 63) | GGCGCUGGAGCAGAAGAGGAA (SEQ ID NO: 64) |
| DRPLA | hATN1Ex5_18 | GTTTCCTTATTCATCCTCTAG (SEQ ID NO: 65) | CUAGAGGAUGAAUAAGGAAAC (SEQ ID NO: 66) |
| DRPLA | hATN1Ex5_19 | GCCTCTCTGTCTCCAATCAGC (SEQ ID NO: 67) | GCUGAUUGGAGACAGAGAGGC (SEQ ID NO: 68) |
| DRPLA | hATN1Ex5_20 | CCATCCCAGGCTGTGTGGAG (SEQ ID NO: 69) | CUCCACACAGCCUGGGAUGG (SEQ ID NO: 70) |
| DRPLA | hATN1Ex5_21 | TCTACTGGGGCCCAGTCCACCG (SEQ ID NO: 71) | CGGUGGACUGGGCCCCAGUAGA (SEQ ID NO: 72) |
| DRPLA | hATN1Ex5_22 | GCATCACGGAAACTCTGGGCC (SEQ ID NO: 73) | GGCCCAGAGUUUCCGUGAUGC (SEQ ID NO: 74) |
| DRPLA | hATN1Ex5_23 | CCACTGGAGGGCGGTAGCTCC (SEQ ID NO: 75) | GGAGCUACCGCCCUCCAGUGG (SEQ ID NO: 76) |
| DRPLA | hATN1Ex5_24 | CTCCCTGGGGTCTCTGAGGCC (SEQ ID NO: 77) | GGCCUCAGAGACCCCAGGGAG (SEQ ID NO: 78) |
| DRPLA | hATN1Ex5_25 | CACCAGGGCCAGCACACCTGC (SEQ ID NO: 79) | GCAGGUGUGCUGGCCCUGGUG (SEQ ID NO: 80) |
| DRPLA | hATN1Ex5_26 | GTGTCCTACAGCCAAGCAGGCC (SEQ ID NO: 81) | GGCCUGCUUGGCUGUAGGACAC (SEQ ID NO: 82) |
| DRPLA | hATN1Ex5_27 | CAAGGGTCCTACCCATGTTCAC (SEQ ID NO: 83) | GUGAACAUGGGUAGGACCCUUG (SEQ ID NO: 84) |
| DRPLA | hATN1Ex5_28 | CACCGGTGCCTACGGTCACCAC (SEQ ID NO: 85) | GUGGUGACCGUAGGCACCGGUG (SEQ ID NO: 86) |
| DRPLA | hATN1Ex5_29 | CTCTTCGGCTACCCTTTCCAC (SEQ ID NO: 87) | GUGGAAAGGGUAGCCGAAGAG (SEQ ID NO: 88) |
| DRPLA | hATN1Ex5_30 | GGTCATTGCCACCGTGGCTTC (SEQ ID NO: 89) | GAAGCCACGGUGGCAAUGACC (SEQ ID NO: 90) |
| DRPLA | hATN1Ex5_31 | CCACCGTACGGAAAGAGAGCC (SEQ ID NO: 91) | GGCUCUCUUUCCGUACGGUGG (SEQ ID NO: 92) |
| DRPLA | hATN1Ex5_32 | CCACCGGGCTATCGAGGAACCTC (SEQ ID NO: 93) | GAGGUUCCUCGAUAGCCCGGUGG (SEQ ID NO: 94) |
| DRPLA | hATN1Ex5_33 | CAGGCCCAGGGACCTTCAAGCC (SEQ ID NO: 95) | GGCUUGAAGGUCCCUGGGCCUG (SEQ ID NO: 96) |
| DRPLA | hATN1Ex5_34 | CCACCGTGGGACCTGGGCCCCTG (SEQ ID NO: 97) | CAGGGGCCCAGGUCCCACGGUGG (SEQ ID NO: 98) |
| DRPLA | hATN1Ex5_35 | GCCACCTGCGGGGCCCTCAGGC (SEQ ID NO: 99) | GCCUGAGGGCCCCGCAGGUGGC (SEQ ID NO: 100) |
| DRPLA | hATN1Ex5_36 | CCATCGCTGCCACCACCACCT (SEQ ID NO: 101) | AGGUGGUGGUGGCAGCGAUGG (SEQ ID NO: 102) |

TABLE 3-continued

AON sequences targeting proteins involved in neurodegenerative diseases

| Disease | AON Name | Target Sequence | AON Sequence |
|---|---|---|---|
| DRPLA | hATN1Ex5_37 | CCTGCCTCAGGGCCGCCCCTG (SEQ ID NO: 103) | CAGGGGCGGCCCUGAGGCAGG (SEQ ID NO: 104) |
| DRPLA | hATN1Ex5_38 | GCCGGCTGAGGAGTATGAGACC (SEQ ID NO: 105) | GGUCUCAUACUCCUCAGCCGGC (SEQ ID NO: 106) |
| DRPLA | hATN1Ex5_39 | CCAAGGTGGTAGATGTACCCA (SEQ ID NO: 107) | UGGGUACAUCUACCACCUUGG (SEQ ID NO: 108) |
| DRPLA | hATN1Ex5_40 | GCCATGCCAGTCAGTCTGCCAG (SEQ ID NO: 109) | CUGGCAGACUGACUGGCAUGGC (SEQ ID NO: 110) |
| DRPLA | hATN1Ex6_1 | CCTGGATCGCGGCTTCAACTC (SEQ ID NO: 111) | GAGUUGAAGCCGCGAUCCAGG (SEQ ID NO: 112) |
| DRPLA | hATN1Ex6_2 | CCTGTACTTCGTGCCACTGGAGG (SEQ ID NO: 113) | CCUCCAGUGGCACGAAGUACAGG (SEQ ID NO: 114) |
| DRPLA | hATN1Ex6_3 | GACCTGGTGGAGAAGGTGCGGCG (SEQ ID NO: 115) | CGCCGCACCUUCUCCACCAGGUC (SEQ ID NO: 116) |
| DRPLA | hATN1Ex6_4 | CGCGAAGAAAAGGAGCGCGAGCG (SEQ ID NO: 117) | CGCUCGCGCUCCUUUUCUUCGCG (SEQ ID NO: 118) |
| DRPLA | hATN1Ex6_5 | GCGAGCGGGAACGCGAGAAAG (SEQ ID NO: 119) | CUUUCUCGCGUUCCCGCUCGC (SEQ ID NO: 120) |
| DRPLA | hATN1Ex6_6 | GCGAGAAGGAGCGCGAGCTTG (SEQ ID NO: 121) | CAAGCUCGCGCUCCUUCUCGC (SEQ ID NO: 122) |
| SCA3 | hATXN3Ex7_1 | TTGTCGTTAAGGGTGATCTGC (SEQ ID NO: 123) | GCAGAUCACCCUUAACGACAA (SEQ ID NO: 124) |
| SCA3 | hATXN3Ex7_2 | CTGCCAGATTGCGAAGCTGA (SEQ ID NO: 125) | UCAGCUUCGCAAUCUGGCAG (SEQ ID NO: 126) |
| SCA3 | hATXN3Ex7_3 | GACCAACTCCTGCAGATGATT (SEQ ID NO: 127) | AAUCAUCUGCAGGAGUUGGUC (SEQ ID NO: 128) |
| SCA3 | hATXN3Ex7_4 | GGTCCAACAGATGCATCGAC (SEQ ID NO: 129) | GUCGAUGCAUCUGUUGGACC (SEQ ID NO: 130) |
| SCA3 | hATXN3Ex7_5 | GCACAACTAAAAGAGCAAAG (SEQ ID NO: 131) | CUUUGCUCUUUUAGUUGUGC (SEQ ID NO: 132) |
| SCA3 | hATXN3Ex8_1 | GTTAGAAGCAAATGATGGCTC (SEQ ID NO: 133) | GAGCCAUCAUUUGCUUCUAAC (SEQ ID NO: 134) |
| SCA3 | hATXN3Ex8_2 | CTCAGGAATGTTAGACGAAG (SEQ ID NO: 135) | CUUCGUCUAACAUUCCUGAG (SEQ ID NO: 136) |
| SCA3 | hATXN3Ex8_3 | GAGGAGGATTTGCAGAGGGC (SEQ ID NO: 137) | GCCCUCUGCAAAUCCUCCUC (SEQ ID NO: 138) |
| SCA3 | hATXN3Ex8_4 | GAGGAAGCAGATCTCCGCAG (SEQ ID NO: 139) | CUGCGGAGAUCUGCUUCCUC (SEQ ID NO: 140) |
| SCA3 | hATXN3Ex8_5 | GGCTATTCAGCTAAGTATGCAAG (SEQ ID NO: 141) | CUUGCAUACUUAGCUGAAUAGCC (SEQ ID NO: 142) |
| SCA3 | hATXN3Ex9_1 | GGTAGTTCCAGAAACATATCTC (SEQ ID NO: 143) | GAGAUAUGUUUCUGGAACUACC (SEQ ID NO: 144) |
| SCA3 | hATXN3Ex9_2 | GCTTCGGAAGAGACGAGAAGC (SEQ ID NO: 145) | GCUUCUCGUCUCUUCCGAAGC (SEQ ID NO: 146) |
| SCA3 | hATXN3Ex10_1 | CAGCAGCAAAAGCAGCAACAGC (SEQ ID NO: 147) | GCUGUUGCUGCUUUUGCUGCUG (SEQ ID NO: 148) |
| SCA3 | hATXN3Ex10_2 | GACCTATCAGGACAGAGTTC (SEQ ID NO: 149) | GAACUCUGUCCUGAUAGGUC (SEQ ID NO: 150) |
| SCA7 | hATXN7Ex3_1 | GAGCGGAAAGAATGTCGGAGC (SEQ ID NO: 151) | GCUCCGACAUUCUUUCCGCUC (SEQ ID NO: 152) |

TABLE 3-continued

AON sequences targeting proteins involved in neurodegenerative diseases

| Disease | AON Name | Target Sequence | AON Sequence |
|---|---|---|---|
| SCA7 | hATXN7Ex3_2 | AGCGGGCCGCGGATGACGTCA (SEQ ID NO: 153) | UGACGUCAUCCGCGGCCCGCU (SEQ ID NO: 154) |
| SCA7 | hATXN7Ex3_3 | AGCAGCCGCCGCCTCCGCAG (SEQ ID NO: 155) | CUGCGGAGGCGGCGGCUGCU (SEQ ID NO: 156) |
| SCA7 | hATXN7Ex3_4 | ACACGGCCGGAGGACGGCG (SEQ ID NO: 157) | CGCCGUCCUCCGGCCGUGU (SEQ ID NO: 158) |
| SCA7 | hATXN7Ex3_5 | GCGCCGCCTCCACCTCGGCCG (SEQ ID NO: 159) | CGGCCGAGGUGGAGGCGGCGC (SEQ ID NO: 160) |
| SCA7 | hATXN7Ex3_6 | ACCTCGGCCGCCGCAATGGCGA (SEQ ID NO: 161) | UCGCCAUUGCGGCGGCCGAGGU (SEQ ID NO: 162) |
| SCA7 | hATXN7Ex3_7 | GGCCTCTGCCCAGTCCTGAAGT (SEQ ID NO: 163) | ACUUCAGGACUGGGCAGAGGCC (SEQ ID NO: 164) |
| SCA7 | hATXN7Ex3_8 | TGATGCTGGGACAGTCGTGGAAT (SEQ ID NO: 165) | AUUCCACGACUGUCCCAGCAUCA (SEQ ID NO: 166) |
| SCA7 | hATXN7Ex3_9 | AGGCTTCCAAACTTCCTGGGAAG (SEQ ID NO: 167) | CUUCCCAGGAAGUUUGGAAGCCU (SEQ ID NO: 168) |
| HD | hHTTEx12_1 | CATCAGCGACAGCTCCCAGACCACCACCG (SEQ ID NO: 169) | CGGUGGUGGUCUGGGAGCUGUCGCUGAUG (SEQ ID NO: 170) |
| HD | hHTTEx12_2 | TCACAGCACACACTGCAGGC (SEQ ID NO: 171) | GCCUGCAGUGUGUGCUGUGA (SEQ ID NO: 172) |
| HD | hHTTEx12_3 | GGTCAGCAGGTCATGACATCAT (SEQ ID NO: 173) | AUGAUGUCAUGACCUGCUGACC (SEQ ID NO: 174) |
| HD | hHTTEx12_4 | AGAGCTGGCTGCTTCTTCAG (SEQ ID NO: 175) | CUGAAGAAGCAGCCAGCUCU (SEQ ID NO: 176) |
| HD | hHTTEx12_5 | GATGAGGAGGATATCTTGAG (SEQ ID NO: 177) | CUCAAGAUAUCCUCCUCAUC (SEQ ID NO: 178) |
| HD | hHTTEx12_6 | TCAGTGAAGGATGAGATCAGTGG (SEQ ID NO: 179) | CCACUGAUCUCAUCCUUCACUGA (SEQ ID NO: 180) |
| HD | hHTTEx12_7 | ATGGACCTGAATGATGGGAC (SEQ ID NO: 181) | GUCCCAUCAUUCAGGUCCAU (SEQ ID NO: 182) |
| HD | hHTTEx12_8 | TGACAAGCTCTGCCACTGAT (SEQ ID NO: 183) | AUCAGUGGCAGAGCUUGUCA (SEQ ID NO: 184) |
| HD | hHTTEx12_9 | TCCAGCCAGGTCAGCGCCGT (SEQ ID NO: 185) | ACGGCGCUGACCUGGCUGGA (SEQ ID NO: 186) |
| HD | hHTTEx12_10 | ACTCAGTGGATCTGGCCAGCT (SEQ ID NO: 187) | AGCUGGCCAGAUCCACUGAGU (SEQ ID NO: 188) |
| HD | hHTTEx13_1 | CCTGCAGATTGGACAGCC (SEQ ID NO: 189) | GGCUGUCCAAUCUGCAGG (SEQ ID NO: 190) |
| HD | hHTTEx13_2 | GGTACCGACAACCAGTATTT (SEQ ID NO: 191) | AAAUACUGGUUGUCGGUACC (SEQ ID NO: 192) |
| HD | hHTTEx14_1 | AACATGAGTCACTGCAGGCAG (SEQ ID NO: 193) | CUGCCUGCAGUGACUCAUGUU (SEQ ID NO: 194) |
| HD | hHTTEx14_2 | GCCTTCTGACAGCAGTGTTGAT (SEQ ID NO: 195) | AUCAACACUGCUGUCAGAAGGC (SEQ ID NO: 196) |
| HD | hHTTEx14_3 | GTTGAGAGATGAAGCTACTG (SEQ ID NO: 197) | CAGUAGCUUCAUCUCUCAAC (SEQ ID NO: 198) |
| SCA17 | hTBPEx3_1: | GCCATGACTCCCGGAATCCCTA (SEQ ID NO: 199) | UAGGGAUUCCGGGAGUCAUGGC (SEQ ID NO: 200) |
| SCA17 | hTBPEx3_2: | CCTATCTTTAGTCCAATGATGC (SEQ ID NO: 201) | GCAUCAUUGGACUAAAGAUAGG (SEQ ID NO: 202) |

TABLE 3-continued

AON sequences targeting proteins involved in neurodegenerative diseases

| Disease | AON Name | Target Sequence | AON Sequence |
|---------|----------|-----------------|--------------|
| SCA17 | hTBPEx3_3: | TATGGCACTGGACTGACCCCAC (SEQ ID NO: 203) | GUGGGGUCAGUCCAGUGCCAUA (SEQ ID NO: 204) |
| SCA17 | hTBPEx3_4: | GCAGCTGCAGCCGTTCAGCAG (SEQ ID NO: 205) | CUGCUGAACGGCUGCAGCUGC (SEQ ID NO: 206) |
| SCA17 | hTBPEx3_5: | GTTCAGCAGTCAACGTCCCAGC (SEQ ID NO: 207) | GCUGGGACGUUGACUGCUGAAC (SEQ ID NO: 208) |
| SCA17 | hTBPEx3_6: | AACCTCAGGCCAGGCACCACAG (SEQ ID NO: 209) | CUGUGGUGCCUGGCCUGAGGUU (SEQ ID NO: 210) |
| SCA17 | hTBPEx3_7: | GCACCACAGCTCTTCCACTCA (SEQ ID NO: 211) | UGAGUGGAAGAGCUGUGGUGC (SEQ ID NO: 212) |
| SCA17 | hTBPEx3_8: | CTCACAGACTCTCACAACTGC (SEQ ID NO: 213) | GCAGUUGUGAGAGUCUGUGAG (SEQ ID NO: 214) |
| SCA17 | hTBPEx3_9: | GGCACCACTCCACTGTATCCCT (SEQ ID NO: 215) | AGGGAUACAGUGGAGUGGUGCC (SEQ ID NO: 216) |
| SCA17 | hTBPEx3_10: | CATCACTCCTGCCACGCCAGCT (SEQ ID NO: 217) | AGCUGGCGUGGCAGGAGUGAUG (SEQ ID NO: 218) |
| SCA17 | hTBPEx3_11: | AGAGTTCTGGGATTGTACCGCA (SEQ ID NO: 219) | UGCGGUACAAUCCCAGAACUCU (SEQ ID NO: 220) |
| SCA17 | hTBPEx4_1: | TGTATCCACAGTGAATCTTGGT (SEQ ID NO: 221) | ACCAAGAUUCACUGUGGAUACA (SEQ ID NO: 222) |
| SCA17 | hTBPEx4_2: | GGTTGTAAACTTGACCTAAAG (SEQ ID NO: 223) | CUUUAGGUCAAGUUUACAACC (SEQ ID NO: 224) |
| SCA17 | hTBPEx4_3: | CATTGCACTTCGTGCCCGAAACG (SEQ ID NO: 225) | CGUUUCGGGCACGAAGUGCAAUG (SEQ ID NO: 226) |

REFERENCES CITED

1. Wellington, C. L. et al. Inhibiting caspase cleavage of huntingtin reduces toxicity and aggregate formation in neuronal and non-neuronal cells. *J. Biol. Chem.* 275, 19831-19838 (2000).
2. Graham, R. K. et al. Cleavage at the Caspase-6 Site Is Required for Neuronal Dysfunction and Degeneration Due to Mutant Huntingtin. *Cell* 125, 1179-1191 (2006).

---

What is claimed is:

1. At least one isolated oligonucleotide of between 14-40 nucleotides that induces skipping of an exonic sequence that comprises the HCHWA-D mutation from mutant human APP protein, wherein the oligonucleotide induces skipping of an exonic sequence corresponding to exon 16 of APP751, wherein the oligonucleotide is selected from the group consisting of SEQ ID NO:20, SEQ ID NO:22, SEQ ID NO:24, SEQ ID NO:26, SEQ ID NO:28, and SEQ ID NO:30.

2. The at least one isolated oligonucleotide of claim 1, wherein the oligonucleotide is SEQ ID NO:20.

3. The at least one isolated oligonucleotide of claim 1, wherein the oligonucleotide is SEQ ID NO:22.

4. The at least one isolated oligonucleotide of claim 1, wherein the oligonucleotide is SEQ ID NO:24.

5. The at least one isolated oligonucleotide of claim 1, wherein the oligonucleotide is SEQ ID NO:26.

6. The at least one isolated oligonucleotide of claim 1, wherein the oligonucleotide is SEQ ID NO:28.

7. The at least one isolated oligonucleotide of claim 1, wherein the oligonucleotide is SEQ ID NO:30.

* * * * *

SEQUENCE LISTING

<160> NUMBER OF SEQ ID NOS: 256

<210> SEQ ID NO 1
<211> LENGTH: 29
<212> TYPE: RNA
<213> ORGANISM: Artificial
<220> FEATURE:
<223> OTHER INFORMATION: AON HDEx12_1

<400> SEQUENCE: 1
cggugguggu cugggagcug ucgcugaug                              29

<210> SEQ ID NO 2
<211> LENGTH: 19
<212> TYPE: RNA
<213> ORGANISM: Artificial
<220> FEATURE:
<223> OTHER INFORMATION: AON HDEx12_2

```
<400> SEQUENCE: 2
ucacagcaca cacugcagg                                                      19

<210> SEQ ID NO 3
<211> LENGTH: 28
<212> TYPE: RNA
<213> ORGANISM: Artificial
<220> FEATURE:
<223> OTHER INFORMATION: AON HDEx13_1

<400> SEQUENCE: 3
guuccugaag gccuccgagg cuucauca                                            28

<210> SEQ ID NO 4
<211> LENGTH: 25
<212> TYPE: RNA
<213> ORGANISM: Artificial
<220> FEATURE:
<223> OTHER INFORMATION: AON HDEx13_2

<400> SEQUENCE: 4
gguccuacuu cuacuccuuc ggugu                                               25

<210> SEQ ID NO 5
<211> LENGTH: 20
<212> TYPE: RNA
<213> ORGANISM: Artificial
<220> FEATURE:
<223> OTHER INFORMATION: AON DRPLAEx5_18

<400> SEQUENCE: 5
gucgcugcug ccaucaucau                                                     20

<210> SEQ ID NO 6
<211> LENGTH: 20
<212> TYPE: RNA
<213> ORGANISM: Artificial
<220> FEATURE:
<223> OTHER INFORMATION: AON DRPLAEx5_128

<400> SEQUENCE: 6
aagaggaagc aggaggcaga                                                     20

<210> SEQ ID NO 7
<211> LENGTH: 20
<212> TYPE: RNA
<213> ORGANISM: Artificial
<220> FEATURE:
<223> OTHER INFORMATION: AON DRPLAEx5_81

<400> SEQUENCE: 7
ggaggagccu ggaacauucg                                                     20

<210> SEQ ID NO 8
<211> LENGTH: 20
<212> TYPE: RNA
<213> ORGANISM: Artificial
<220> FEATURE:
<223> OTHER INFORMATION: AON DRPLAEx6_80

<400> SEQUENCE: 8
aagcucgcgc uccuucucgc                                                     20

<210> SEQ ID NO 9
<211> LENGTH: 20
```

```
<212> TYPE: RNA
<213> ORGANISM: Artificial
<220> FEATURE:
<223> OTHER INFORMATION: AON DRPLAEx6_1

<400> SEQUENCE: 9
cgaguugaag ccgcgaucca                                               20

<210> SEQ ID NO 10
<211> LENGTH: 20
<212> TYPE: RNA
<213> ORGANISM: Artificial
<220> FEATURE:
<223> OTHER INFORMATION: AON DRPLAEx6_84

<400> SEQUENCE: 10
guucaagcuc gcgccuuc                                                 20

<210> SEQ ID NO 11
<211> LENGTH: 23
<212> TYPE: DNA
<213> ORGANISM: Artificial
<220> FEATURE:
<223> OTHER INFORMATION: target hAPPEx15_1

<400> SEQUENCE: 11
gttctgggtt gacaaatatc aag                                           23

<210> SEQ ID NO 12
<211> LENGTH: 23
<212> TYPE: RNA
<213> ORGANISM: Artificial
<220> FEATURE:
<223> OTHER INFORMATION: AON hAPPEx15_1

<400> SEQUENCE: 12
cuugauauuu gucaacccag aac                                           23

<210> SEQ ID NO 13
<211> LENGTH: 23
<212> TYPE: DNA
<213> ORGANISM: Artificial
<220> FEATURE:
<223> OTHER INFORMATION: target hAPPEx15_2

<400> SEQUENCE: 13
cggaggagat ctctgaagtg aag                                           23

<210> SEQ ID NO 14
<211> LENGTH: 23
<212> TYPE: RNA
<213> ORGANISM: Artificial
<220> FEATURE:
<223> OTHER INFORMATION: AON hAPPEx15_2

<400> SEQUENCE: 14
cuucacuuca gagaucuccu ccg                                           23

<210> SEQ ID NO 15
<211> LENGTH: 21
<212> TYPE: DNA
<213> ORGANISM: Artificial
<220> FEATURE:
<223> OTHER INFORMATION: target hAPPEx15_3

<400> SEQUENCE: 15
```

```
gatgcagaat tccgacatga c                                              21

<210> SEQ ID NO 16
<211> LENGTH: 21
<212> TYPE: RNA
<213> ORGANISM: Artificial
<220> FEATURE:
<223> OTHER INFORMATION: AON hAPPEx15_3

<400> SEQUENCE: 16
gucaugucgg aauucugcau c                                              21

<210> SEQ ID NO 17
<211> LENGTH: 23
<212> TYPE: DNA
<213> ORGANISM: Artificial
<220> FEATURE:
<223> OTHER INFORMATION: target hAPPEx15_4

<400> SEQUENCE: 17
ctcaggatat gaagttcatc atc                                            23

<210> SEQ ID NO 18
<211> LENGTH: 23
<212> TYPE: RNA
<213> ORGANISM: Artificial
<220> FEATURE:
<223> OTHER INFORMATION: AON hAPPEx15_4

<400> SEQUENCE: 18
gaugaugaac uucauauccu gag                                            23

<210> SEQ ID NO 19
<211> LENGTH: 20
<212> TYPE: DNA
<213> ORGANISM: Artificial
<220> FEATURE:
<223> OTHER INFORMATION: target hAPPEx16_1

<400> SEQUENCE: 19
gcaatcattg gactcatggt                                                20

<210> SEQ ID NO 20
<211> LENGTH: 20
<212> TYPE: RNA
<213> ORGANISM: Artificial
<220> FEATURE:
<223> OTHER INFORMATION: AON hAPPEx16_1

<400> SEQUENCE: 20
accaugaguc caaugauugc                                                20

<210> SEQ ID NO 21
<211> LENGTH: 20
<212> TYPE: DNA
<213> ORGANISM: Artificial
<220> FEATURE:
<223> OTHER INFORMATION: target hAPPEx16_2

<400> SEQUENCE: 21
gatcgtcatc accttggtga                                                20

<210> SEQ ID NO 22
<211> LENGTH: 20
<212> TYPE: RNA
<213> ORGANISM: Artificial
```

-continued

```
<220> FEATURE:
<223> OTHER INFORMATION: AON hAPPEx16_2

<400> SEQUENCE: 22
ucaccaaggu gaugacgauc                                                    20

<210> SEQ ID NO 23
<211> LENGTH: 23
<212> TYPE: DNA
<213> ORGANISM: Artificial
<220> FEATURE:
<223> OTHER INFORMATION: target hAPPEx16_3

<400> SEQUENCE: 23
gtacacatcc attcatcatg gtg                                                23

<210> SEQ ID NO 24
<211> LENGTH: 23
<212> TYPE: RNA
<213> ORGANISM: Artificial
<220> FEATURE:
<223> OTHER INFORMATION: AON hAPPEx16_3

<400> SEQUENCE: 24
caccaugaug aauggaugug uac                                                23

<210> SEQ ID NO 25
<211> LENGTH: 21
<212> TYPE: DNA
<213> ORGANISM: Artificial
<220> FEATURE:
<223> OTHER INFORMATION: target hAPPEx16_4

<400> SEQUENCE: 25
gcagaagatg tgggttcaaa c                                                  21

<210> SEQ ID NO 26
<211> LENGTH: 21
<212> TYPE: RNA
<213> ORGANISM: Artificial
<220> FEATURE:
<223> OTHER INFORMATION: AON hAPPEx16_4

<400> SEQUENCE: 26
guuugaaccc acaucuucug c                                                  21

<210> SEQ ID NO 27
<211> LENGTH: 22
<212> TYPE: DNA
<213> ORGANISM: Artificial
<220> FEATURE:
<223> OTHER INFORMATION: target hAPPEx16_5

<400> SEQUENCE: 27
ggtgatgctg aagaagaaac ag                                                 22

<210> SEQ ID NO 28
<211> LENGTH: 22
<212> TYPE: RNA
<213> ORGANISM: Artificial
<220> FEATURE:
<223> OTHER INFORMATION: AON hAPPEx16_5

<400> SEQUENCE: 28
cuguuucuuc uucagcauca cc                                                 22
```

```
<210> SEQ ID NO 29
<211> LENGTH: 23
<212> TYPE: DNA
<213> ORGANISM: Artificial
<220> FEATURE:
<223> OTHER INFORMATION: target hAPPEx16_6

<400> SEQUENCE: 29
tcatcatggt gtggtggagg tag                                              23

<210> SEQ ID NO 30
<211> LENGTH: 23
<212> TYPE: RNA
<213> ORGANISM: Artificial
<220> FEATURE:
<223> OTHER INFORMATION: AON hAPPEx16_6

<400> SEQUENCE: 30
cuaccuccac cacaccauga uga                                              23

<210> SEQ ID NO 31
<211> LENGTH: 22
<212> TYPE: DNA
<213> ORGANISM: Artificial
<220> FEATURE:
<223> OTHER INFORMATION: target hATN1Ex5_1

<400> SEQUENCE: 31
ctccctcggc cacagtctcc ct                                               22

<210> SEQ ID NO 32
<211> LENGTH: 22
<212> TYPE: RNA
<213> ORGANISM: Artificial
<220> FEATURE:
<223> OTHER INFORMATION: AON hATN1Ex5_1

<400> SEQUENCE: 32
agggagacug uggccgaggg ag                                               22

<210> SEQ ID NO 33
<211> LENGTH: 22
<212> TYPE: DNA
<213> ORGANISM: Artificial
<220> FEATURE:
<223> OTHER INFORMATION: target hATN1Ex5_2

<400> SEQUENCE: 33
gcggagcctt aatgatgatg gc                                               22

<210> SEQ ID NO 34
<211> LENGTH: 22
<212> TYPE: RNA
<213> ORGANISM: Artificial
<220> FEATURE:
<223> OTHER INFORMATION: AON hATN1Ex5_2

<400> SEQUENCE: 34
gccaucauca uuaaggcucc gc                                               22

<210> SEQ ID NO 35
<211> LENGTH: 22
<212> TYPE: DNA
<213> ORGANISM: Artificial
<220> FEATURE:
<223> OTHER INFORMATION: target hATN1Ex5_3
```

```
<400> SEQUENCE: 35
agcagcgacc ctagggatat cg                                      22

<210> SEQ ID NO 36
<211> LENGTH: 22
<212> TYPE: RNA
<213> ORGANISM: Artificial
<220> FEATURE:
<223> OTHER INFORMATION: AON hATN1Ex5_3

<400> SEQUENCE: 36
cgauaucccu aggucgcug cu                                       22

<210> SEQ ID NO 37
<211> LENGTH: 21
<212> TYPE: DNA
<213> ORGANISM: Artificial
<220> FEATURE:
<223> OTHER INFORMATION: target hATN1Ex5_4

<400> SEQUENCE: 37
aggacaaccg aagcacgtcc c                                       21

<210> SEQ ID NO 38
<211> LENGTH: 21
<212> TYPE: RNA
<213> ORGANISM: Artificial
<220> FEATURE:
<223> OTHER INFORMATION: AON hATN1Ex5_4

<400> SEQUENCE: 38
gggacgugcu ucgguugucc u                                       21

<210> SEQ ID NO 39
<211> LENGTH: 23
<212> TYPE: DNA
<213> ORGANISM: Artificial
<220> FEATURE:
<223> OTHER INFORMATION: target hATN1Ex5_5

<400> SEQUENCE: 39
tggaagtgtg gagaatgact ctg                                     23

<210> SEQ ID NO 40
<211> LENGTH: 23
<212> TYPE: RNA
<213> ORGANISM: Artificial
<220> FEATURE:
<223> OTHER INFORMATION: AON hATN1Ex5_5

<400> SEQUENCE: 40
cagagucauu cuccacacuu cca                                     23

<210> SEQ ID NO 41
<211> LENGTH: 22
<212> TYPE: DNA
<213> ORGANISM: Artificial
<220> FEATURE:
<223> OTHER INFORMATION: target hATN1Ex5_6

<400> SEQUENCE: 41
atcttctggc ctgtcccagg gc                                      22

<210> SEQ ID NO 42
```

```
<211> LENGTH: 22
<212> TYPE: RNA
<213> ORGANISM: Artificial
<220> FEATURE:
<223> OTHER INFORMATION: AON hATN1Ex5_6

<400> SEQUENCE: 42
gcccugggac aggccagaag au                                              22

<210> SEQ ID NO 43
<211> LENGTH: 23
<212> TYPE: DNA
<213> ORGANISM: Artificial
<220> FEATURE:
<223> OTHER INFORMATION: target hATN1Ex5_7

<400> SEQUENCE: 43
cgacagccag aggctagctt tga                                             23

<210> SEQ ID NO 44
<211> LENGTH: 23
<212> TYPE: RNA
<213> ORGANISM: Artificial
<220> FEATURE:
<223> OTHER INFORMATION: AON hATN1Ex5_7

<400> SEQUENCE: 44
ucaaagcuag ccucuggcug ucg                                             23

<210> SEQ ID NO 45
<211> LENGTH: 22
<212> TYPE: DNA
<213> ORGANISM: Artificial
<220> FEATURE:
<223> OTHER INFORMATION: target hATN1Ex5_8

<400> SEQUENCE: 45
ctcgaatgtt ccaggctcct cc                                              22

<210> SEQ ID NO 46
<211> LENGTH: 22
<212> TYPE: RNA
<213> ORGANISM: Artificial
<220> FEATURE:
<223> OTHER INFORMATION: AON hATN1Ex5_8

<400> SEQUENCE: 46
ggaggagccu ggaacauucg ag                                              22

<210> SEQ ID NO 47
<211> LENGTH: 22
<212> TYPE: DNA
<213> ORGANISM: Artificial
<220> FEATURE:
<223> OTHER INFORMATION: target hATN1Ex5_9

<400> SEQUENCE: 47
tctatcctgg gggcactggt gg                                              22

<210> SEQ ID NO 48
<211> LENGTH: 22
<212> TYPE: RNA
<213> ORGANISM: Artificial
<220> FEATURE:
<223> OTHER INFORMATION: AON hATN1Ex5_9

<400> SEQUENCE: 48
```

```
ccaccagugc ccccaggaua ga                                              22

<210> SEQ ID NO 49
<211> LENGTH: 22
<212> TYPE: DNA
<213> ORGANISM: Artificial
<220> FEATURE:
<223> OTHER INFORMATION: target hATN1Ex5_10

<400> SEQUENCE: 49
tggaccccca atgggtccca ag                                              22

<210> SEQ ID NO 50
<211> LENGTH: 22
<212> TYPE: RNA
<213> ORGANISM: Artificial
<220> FEATURE:
<223> OTHER INFORMATION: AON hATN1Ex5_10

<400> SEQUENCE: 50
cuugggaccc auuggggguc ca                                              22

<210> SEQ ID NO 51
<211> LENGTH: 20
<212> TYPE: DNA
<213> ORGANISM: Artificial
<220> FEATURE:
<223> OTHER INFORMATION: target hATN1Ex5_11

<400> SEQUENCE: 51
aggggctgcc tcatcagtgg                                                 20

<210> SEQ ID NO 52
<211> LENGTH: 20
<212> TYPE: RNA
<213> ORGANISM: Artificial
<220> FEATURE:
<223> OTHER INFORMATION: AON hATN1Ex5_11

<400> SEQUENCE: 52
ccacugauga ggcagccccu                                                 20

<210> SEQ ID NO 53
<211> LENGTH: 23
<212> TYPE: DNA
<213> ORGANISM: Artificial
<220> FEATURE:
<223> OTHER INFORMATION: target hATN1Ex5_12

<400> SEQUENCE: 53
aagctctggg gctagtggtg ctc                                             23

<210> SEQ ID NO 54
<211> LENGTH: 23
<212> TYPE: RNA
<213> ORGANISM: Artificial
<220> FEATURE:
<223> OTHER INFORMATION: AON hATN1Ex5_12

<400> SEQUENCE: 54
gagcaccacu agccccagag cuu                                             23

<210> SEQ ID NO 55
<211> LENGTH: 22
<212> TYPE: DNA
```

<213> ORGANISM: Artificial
<220> FEATURE:
<223> OTHER INFORMATION: target hATN1Ex5_13

<400> SEQUENCE: 55
acaaagccgc ctaccactcc ag                                              22

<210> SEQ ID NO 56
<211> LENGTH: 22
<212> TYPE: RNA
<213> ORGANISM: Artificial
<220> FEATURE:
<223> OTHER INFORMATION: AON hATN1Ex5_13

<400> SEQUENCE: 56
cuggaguggu aggcggcuuu gu                                              22

<210> SEQ ID NO 57
<211> LENGTH: 21
<212> TYPE: DNA
<213> ORGANISM: Artificial
<220> FEATURE:
<223> OTHER INFORMATION: target hATN1Ex5_14

<400> SEQUENCE: 57
ctccaccacc agccaacttc c                                               21

<210> SEQ ID NO 58
<211> LENGTH: 21
<212> TYPE: RNA
<213> ORGANISM: Artificial
<220> FEATURE:
<223> OTHER INFORMATION: AON hATN1Ex5_14

<400> SEQUENCE: 58
ggaaguuggc ugguggugga g                                               21

<210> SEQ ID NO 59
<211> LENGTH: 22
<212> TYPE: DNA
<213> ORGANISM: Artificial
<220> FEATURE:
<223> OTHER INFORMATION: target hATN1Ex5_15

<400> SEQUENCE: 59
ccaaccacta cctggtcatc tg                                              22

<210> SEQ ID NO 60
<211> LENGTH: 22
<212> TYPE: RNA
<213> ORGANISM: Artificial
<220> FEATURE:
<223> OTHER INFORMATION: AON hATN1Ex5_15

<400> SEQUENCE: 60
cagaugacca gguagugguu gg                                              22

<210> SEQ ID NO 61
<211> LENGTH: 21
<212> TYPE: DNA
<213> ORGANISM: Artificial
<220> FEATURE:
<223> OTHER INFORMATION: target hATN1Ex5_16

<400> SEQUENCE: 61
tggcccagag aagggcccaa c                                               21

<210> SEQ ID NO 62
<211> LENGTH: 21
<212> TYPE: RNA
<213> ORGANISM: Artificial
<220> FEATURE:
<223> OTHER INFORMATION: AON hATN1Ex5_16

<400> SEQUENCE: 62
guugggcccu ucucugggcc a					21

<210> SEQ ID NO 63
<211> LENGTH: 21
<212> TYPE: DNA
<213> ORGANISM: Artificial
<220> FEATURE:
<223> OTHER INFORMATION: target hATN1Ex5_17

<400> SEQUENCE: 63
ttcctcttct gctccagcgc c					21

<210> SEQ ID NO 64
<211> LENGTH: 21
<212> TYPE: RNA
<213> ORGANISM: Artificial
<220> FEATURE:
<223> OTHER INFORMATION: AON hATN1Ex5_17

<400> SEQUENCE: 64
ggcgcuggag cagaagagga a					21

<210> SEQ ID NO 65
<211> LENGTH: 21
<212> TYPE: DNA
<213> ORGANISM: Artificial
<220> FEATURE:
<223> OTHER INFORMATION: target hATN1Ex5_18

<400> SEQUENCE: 65
gtttccttat tcatcctcta g					21

<210> SEQ ID NO 66
<211> LENGTH: 21
<212> TYPE: RNA
<213> ORGANISM: Artificial
<220> FEATURE:
<223> OTHER INFORMATION: AON hATN1Ex5_18

<400> SEQUENCE: 66
cuagaggaug aauaaggaaa c					21

<210> SEQ ID NO 67
<211> LENGTH: 21
<212> TYPE: DNA
<213> ORGANISM: Artificial
<220> FEATURE:
<223> OTHER INFORMATION: target hATN1Ex5_19

<400> SEQUENCE: 67
gcctctctgt ctccaatcag c					21

<210> SEQ ID NO 68
<211> LENGTH: 21
<212> TYPE: RNA
<213> ORGANISM: Artificial
<220> FEATURE:

<223> OTHER INFORMATION: AON hATN1Ex5_19

<400> SEQUENCE: 68
gcugauugga gacagagagg c     21

<210> SEQ ID NO 69
<211> LENGTH: 20
<212> TYPE: DNA
<213> ORGANISM: Artificial
<220> FEATURE:
<223> OTHER INFORMATION: target hATN1Ex5_20

<400> SEQUENCE: 69
ccatcccagg ctgtgtggag     20

<210> SEQ ID NO 70
<211> LENGTH: 20
<212> TYPE: RNA
<213> ORGANISM: Artificial
<220> FEATURE:
<223> OTHER INFORMATION: AON hATN1Ex5_20

<400> SEQUENCE: 70
cuccacacag ccugggaugg     20

<210> SEQ ID NO 71
<211> LENGTH: 22
<212> TYPE: DNA
<213> ORGANISM: Artificial
<220> FEATURE:
<223> OTHER INFORMATION: target hATN1Ex5_21

<400> SEQUENCE: 71
tctactgggg cccagtccac cg     22

<210> SEQ ID NO 72
<211> LENGTH: 22
<212> TYPE: RNA
<213> ORGANISM: Artificial
<220> FEATURE:
<223> OTHER INFORMATION: AON hATN1Ex5_21

<400> SEQUENCE: 72
cgguggacug ggcccagua ga     22

<210> SEQ ID NO 73
<211> LENGTH: 21
<212> TYPE: DNA
<213> ORGANISM: Artificial
<220> FEATURE:
<223> OTHER INFORMATION: target hATN1Ex5_22

<400> SEQUENCE: 73
gcatcacgga aactctgggc c     21

<210> SEQ ID NO 74
<211> LENGTH: 21
<212> TYPE: RNA
<213> ORGANISM: Artificial
<220> FEATURE:
<223> OTHER INFORMATION: AON hATN1Ex5_22

<400> SEQUENCE: 74
ggcccagagu uuccgugaug c     21

```
<210> SEQ ID NO 75
<211> LENGTH: 21
<212> TYPE: DNA
<213> ORGANISM: Artificial
<220> FEATURE:
<223> OTHER INFORMATION: target hATN1Ex5_23

<400> SEQUENCE: 75
ccactggagg gcggtagctc c                                              21

<210> SEQ ID NO 76
<211> LENGTH: 21
<212> TYPE: RNA
<213> ORGANISM: Artificial
<220> FEATURE:
<223> OTHER INFORMATION: AON hATN1Ex5_23

<400> SEQUENCE: 76
ggagcuaccg cccuccagug g                                              21

<210> SEQ ID NO 77
<211> LENGTH: 21
<212> TYPE: DNA
<213> ORGANISM: Artificial
<220> FEATURE:
<223> OTHER INFORMATION: target hATN1Ex5_24

<400> SEQUENCE: 77
ctccctgggg tctctgaggc c                                              21

<210> SEQ ID NO 78
<211> LENGTH: 21
<212> TYPE: RNA
<213> ORGANISM: Artificial
<220> FEATURE:
<223> OTHER INFORMATION: AON hATN1Ex5_24

<400> SEQUENCE: 78
ggccucagag accccaggga g                                              21

<210> SEQ ID NO 79
<211> LENGTH: 21
<212> TYPE: DNA
<213> ORGANISM: Artificial
<220> FEATURE:
<223> OTHER INFORMATION: target hATN1Ex5_25

<400> SEQUENCE: 79
caccagggcc agcacacctg c                                              21

<210> SEQ ID NO 80
<211> LENGTH: 21
<212> TYPE: RNA
<213> ORGANISM: Artificial
<220> FEATURE:
<223> OTHER INFORMATION: AON hATN1Ex5_25

<400> SEQUENCE: 80
gcaggugugc uggcccuggu g                                              21

<210> SEQ ID NO 81
<211> LENGTH: 22
<212> TYPE: DNA
<213> ORGANISM: Artificial
<220> FEATURE:
<223> OTHER INFORMATION: target hATN1Ex5_26
```

<400> SEQUENCE: 81
gtgtcctaca gccaagcagg cc                                              22

<210> SEQ ID NO 82
<211> LENGTH: 22
<212> TYPE: RNA
<213> ORGANISM: Artificial
<220> FEATURE:
<223> OTHER INFORMATION: AON hATN1Ex5_26

<400> SEQUENCE: 82
ggccugcuug gcuguaggac ac                                              22

<210> SEQ ID NO 83
<211> LENGTH: 22
<212> TYPE: DNA
<213> ORGANISM: Artificial
<220> FEATURE:
<223> OTHER INFORMATION: target hATN1Ex5_27

<400> SEQUENCE: 83
caagggtcct acccatgttc ac                                              22

<210> SEQ ID NO 84
<211> LENGTH: 22
<212> TYPE: RNA
<213> ORGANISM: Artificial
<220> FEATURE:
<223> OTHER INFORMATION: AON hATN1Ex5_27

<400> SEQUENCE: 84
gugaacaugg guaggacccu ug                                              22

<210> SEQ ID NO 85
<211> LENGTH: 22
<212> TYPE: DNA
<213> ORGANISM: Artificial
<220> FEATURE:
<223> OTHER INFORMATION: target hATN1Ex5_28

<400> SEQUENCE: 85
caccggtgcc tacggtcacc ac                                              22

<210> SEQ ID NO 86
<211> LENGTH: 22
<212> TYPE: RNA
<213> ORGANISM: Artificial
<220> FEATURE:
<223> OTHER INFORMATION: AON hATN1Ex5_28

<400> SEQUENCE: 86
guggugaccg uaggcaccgg ug                                              22

<210> SEQ ID NO 87
<211> LENGTH: 21
<212> TYPE: DNA
<213> ORGANISM: Artificial
<220> FEATURE:
<223> OTHER INFORMATION: target hATN1Ex5_29

<400> SEQUENCE: 87
ctcttcggct acccttccca c                                               21

<210> SEQ ID NO 88
<211> LENGTH: 21

```
<212> TYPE: RNA
<213> ORGANISM: Artificial
<220> FEATURE:
<223> OTHER INFORMATION: AON hATN1Ex5_29

<400> SEQUENCE: 88
guggaaaggg uagccgaaga g                                             21

<210> SEQ ID NO 89
<211> LENGTH: 21
<212> TYPE: DNA
<213> ORGANISM: Artificial
<220> FEATURE:
<223> OTHER INFORMATION: target hATN1Ex5_30

<400> SEQUENCE: 89
ggtcattgcc accgtggctt c                                             21

<210> SEQ ID NO 90
<211> LENGTH: 21
<212> TYPE: RNA
<213> ORGANISM: Artificial
<220> FEATURE:
<223> OTHER INFORMATION: AON hATN1Ex5_30

<400> SEQUENCE: 90
gaagccacgg uggcaaugac c                                             21

<210> SEQ ID NO 91
<211> LENGTH: 21
<212> TYPE: DNA
<213> ORGANISM: Artificial
<220> FEATURE:
<223> OTHER INFORMATION: target hATN1Ex5_31

<400> SEQUENCE: 91
ccaccgtacg gaaagagagc c                                             21

<210> SEQ ID NO 92
<211> LENGTH: 21
<212> TYPE: RNA
<213> ORGANISM: Artificial
<220> FEATURE:
<223> OTHER INFORMATION: AON hATN1Ex5_31

<400> SEQUENCE: 92
ggcucucuuu ccguacggug g                                             21

<210> SEQ ID NO 93
<211> LENGTH: 23
<212> TYPE: DNA
<213> ORGANISM: Artificial
<220> FEATURE:
<223> OTHER INFORMATION: target hATN1Ex5_32

<400> SEQUENCE: 93
ccaccgggct atcgaggaac ctc                                           23

<210> SEQ ID NO 94
<211> LENGTH: 23
<212> TYPE: RNA
<213> ORGANISM: Artificial
<220> FEATURE:
<223> OTHER INFORMATION: AON hATN1Ex5_32

<400> SEQUENCE: 94
```

-continued

```
gagguuccuc gauagcccgg ugg                                              23

<210> SEQ ID NO 95
<211> LENGTH: 22
<212> TYPE: DNA
<213> ORGANISM: Artificial
<220> FEATURE:
<223> OTHER INFORMATION: target hATN1Ex5_33

<400> SEQUENCE: 95
caggcccagg gaccttcaag cc                                               22

<210> SEQ ID NO 96
<211> LENGTH: 22
<212> TYPE: RNA
<213> ORGANISM: Artificial
<220> FEATURE:
<223> OTHER INFORMATION: AON hATN1Ex5_33

<400> SEQUENCE: 96
ggcuugaagg ucccugggcc ug                                               22

<210> SEQ ID NO 97
<211> LENGTH: 23
<212> TYPE: DNA
<213> ORGANISM: Artificial
<220> FEATURE:
<223> OTHER INFORMATION: target hATN1Ex5_34

<400> SEQUENCE: 97
ccaccgtggg acctgggccc ctg                                              23

<210> SEQ ID NO 98
<211> LENGTH: 23
<212> TYPE: RNA
<213> ORGANISM: Artificial
<220> FEATURE:
<223> OTHER INFORMATION: AON hATN1Ex5_34

<400> SEQUENCE: 98
caggggccca ggucccacgg ugg                                              23

<210> SEQ ID NO 99
<211> LENGTH: 22
<212> TYPE: DNA
<213> ORGANISM: Artificial
<220> FEATURE:
<223> OTHER INFORMATION: target hATN1Ex5_35

<400> SEQUENCE: 99
gccacctgcg gggccctcag gc                                               22

<210> SEQ ID NO 100
<211> LENGTH: 22
<212> TYPE: RNA
<213> ORGANISM: Artificial
<220> FEATURE:
<223> OTHER INFORMATION: AON hATN1Ex5_35

<400> SEQUENCE: 100
gccugagggc cccgcaggug gc                                               22

<210> SEQ ID NO 101
<211> LENGTH: 21
<212> TYPE: DNA
<213> ORGANISM: Artificial
```

```
<220> FEATURE:
<223> OTHER INFORMATION: target hATN1Ex5_36

<400> SEQUENCE: 101
ccatcgctgc caccaccacc t                                              21

<210> SEQ ID NO 102
<211> LENGTH: 21
<212> TYPE: RNA
<213> ORGANISM: Artificial
<220> FEATURE:
<223> OTHER INFORMATION: AON hATN1Ex5_36

<400> SEQUENCE: 102
aggugguggu ggcagcgaug g                                              21

<210> SEQ ID NO 103
<211> LENGTH: 21
<212> TYPE: DNA
<213> ORGANISM: Artificial
<220> FEATURE:
<223> OTHER INFORMATION: target hATN1Ex5_37

<400> SEQUENCE: 103
cctgcctcag ggccgcccct g                                              21

<210> SEQ ID NO 104
<211> LENGTH: 21
<212> TYPE: RNA
<213> ORGANISM: Artificial
<220> FEATURE:
<223> OTHER INFORMATION: AON hATN1Ex5_37

<400> SEQUENCE: 104
caggggcggc ccugaggcag g                                              21

<210> SEQ ID NO 105
<211> LENGTH: 22
<212> TYPE: DNA
<213> ORGANISM: Artificial
<220> FEATURE:
<223> OTHER INFORMATION: target hATN1Ex5_38

<400> SEQUENCE: 105
gccggctgag gagtatgaga cc                                             22

<210> SEQ ID NO 106
<211> LENGTH: 22
<212> TYPE: RNA
<213> ORGANISM: Artificial
<220> FEATURE:
<223> OTHER INFORMATION: AON hATN1Ex5_38

<400> SEQUENCE: 106
ggucucauac uccucagccg gc                                             22

<210> SEQ ID NO 107
<211> LENGTH: 21
<212> TYPE: DNA
<213> ORGANISM: Artificial
<220> FEATURE:
<223> OTHER INFORMATION: target hATN1Ex5_39

<400> SEQUENCE: 107
ccaaggtggt agatgtaccc a                                              21
```

```
<210> SEQ ID NO 108
<211> LENGTH: 21
<212> TYPE: RNA
<213> ORGANISM: Artificial
<220> FEATURE:
<223> OTHER INFORMATION: AON  hATN1Ex5_

<400> SEQUENCE: 108
uggguacauc uaccaccuug g                                              21

<210> SEQ ID NO 109
<211> LENGTH: 22
<212> TYPE: DNA
<213> ORGANISM: Artificial
<220> FEATURE:
<223> OTHER INFORMATION: target hATN1Ex5_40

<400> SEQUENCE: 109
gccatgccag tcagtctgcc ag                                             22

<210> SEQ ID NO 110
<211> LENGTH: 22
<212> TYPE: RNA
<213> ORGANISM: Artificial
<220> FEATURE:
<223> OTHER INFORMATION: AON hATN1Ex5_40

<400> SEQUENCE: 110
cuggcagacu gacuggcaug gc                                             22

<210> SEQ ID NO 111
<211> LENGTH: 21
<212> TYPE: DNA
<213> ORGANISM: Artificial
<220> FEATURE:
<223> OTHER INFORMATION: target hATN1Ex6_1

<400> SEQUENCE: 111
cctggatcgc ggcttcaact c                                              21

<210> SEQ ID NO 112
<211> LENGTH: 21
<212> TYPE: RNA
<213> ORGANISM: Artificial
<220> FEATURE:
<223> OTHER INFORMATION: AON hATN1Ex6_1

<400> SEQUENCE: 112
gaguugaagc cgcgauccag g                                              21

<210> SEQ ID NO 113
<211> LENGTH: 23
<212> TYPE: DNA
<213> ORGANISM: Artificial
<220> FEATURE:
<223> OTHER INFORMATION: target hATN1Ex6_2

<400> SEQUENCE: 113
cctgtacttc gtgccactgg agg                                            23

<210> SEQ ID NO 114
<211> LENGTH: 23
<212> TYPE: RNA
<213> ORGANISM: Artificial
<220> FEATURE:
<223> OTHER INFORMATION: AON hATN1Ex6_2
```

-continued

<400> SEQUENCE: 114
ccuccagugg cacgaaguac agg                                              23

<210> SEQ ID NO 115
<211> LENGTH: 23
<212> TYPE: DNA
<213> ORGANISM: Artificial
<220> FEATURE:
<223> OTHER INFORMATION: target hATN1Ex6_3

<400> SEQUENCE: 115
gacctggtgg agaaggtgcg gcg                                              23

<210> SEQ ID NO 116
<211> LENGTH: 23
<212> TYPE: RNA
<213> ORGANISM: Artificial
<220> FEATURE:
<223> OTHER INFORMATION: AON hATN1Ex6_3

<400> SEQUENCE: 116
cgccgcaccu ucuccaccag guc                                              23

<210> SEQ ID NO 117
<211> LENGTH: 23
<212> TYPE: DNA
<213> ORGANISM: Artificial
<220> FEATURE:
<223> OTHER INFORMATION: target hATN1Ex6_4

<400> SEQUENCE: 117
cgcgaagaaa aggagcgcga gcg                                              23

<210> SEQ ID NO 118
<211> LENGTH: 23
<212> TYPE: RNA
<213> ORGANISM: Artificial
<220> FEATURE:
<223> OTHER INFORMATION: AON hATN1Ex6_4

<400> SEQUENCE: 118
cgcucgcgcu ccuuuucuuc gcg                                              23

<210> SEQ ID NO 119
<211> LENGTH: 21
<212> TYPE: DNA
<213> ORGANISM: Artificial
<220> FEATURE:
<223> OTHER INFORMATION: target hATN1Ex6_5

<400> SEQUENCE: 119
gcgagcggga acgcgagaaa g                                                21

<210> SEQ ID NO 120
<211> LENGTH: 21
<212> TYPE: RNA
<213> ORGANISM: Artificial
<220> FEATURE:
<223> OTHER INFORMATION: AON hATN1Ex6_5

<400> SEQUENCE: 120
cuuucucgcg uucccgcucg c                                                21

<210> SEQ ID NO 121

-continued

<210> SEQ ID NO 121
<211> LENGTH: 21
<212> TYPE: DNA
<213> ORGANISM: Artificial
<220> FEATURE:
<223> OTHER INFORMATION: target hATN1Ex6_6

<400> SEQUENCE: 121
gcgagaagga gcgcgagctt g                                              21

<210> SEQ ID NO 122
<211> LENGTH: 21
<212> TYPE: RNA
<213> ORGANISM: Artificial
<220> FEATURE:
<223> OTHER INFORMATION: AON hATN1Ex6_6

<400> SEQUENCE: 122
caagcucgcg cuccuucucg c                                              21

<210> SEQ ID NO 123
<211> LENGTH: 21
<212> TYPE: DNA
<213> ORGANISM: Artificial
<220> FEATURE:
<223> OTHER INFORMATION: target hATXN3Ex7_1

<400> SEQUENCE: 123
ttgtcgttaa gggtgatctg c                                              21

<210> SEQ ID NO 124
<211> LENGTH: 21
<212> TYPE: RNA
<213> ORGANISM: Artificial
<220> FEATURE:
<223> OTHER INFORMATION: AON hATXN3Ex7_1

<400> SEQUENCE: 124
gcagaucacc cuuaacgaca a                                              21

<210> SEQ ID NO 125
<211> LENGTH: 20
<212> TYPE: DNA
<213> ORGANISM: Artificial
<220> FEATURE:
<223> OTHER INFORMATION: target hATXN3Ex7_2

<400> SEQUENCE: 125
ctgccagatt gcgaagctga                                                20

<210> SEQ ID NO 126
<211> LENGTH: 20
<212> TYPE: RNA
<213> ORGANISM: Artificial
<220> FEATURE:
<223> OTHER INFORMATION: AON hATXN3Ex7_2

<400> SEQUENCE: 126
ucagcuucgc aaucuggcag                                                20

<210> SEQ ID NO 127
<211> LENGTH: 21
<212> TYPE: DNA
<213> ORGANISM: Artificial
<220> FEATURE:
<223> OTHER INFORMATION: target hATXN3Ex7_3

<400> SEQUENCE: 127
gaccaactcc tgcagatgat t                                              21

<210> SEQ ID NO 128
<211> LENGTH: 21
<212> TYPE: RNA
<213> ORGANISM: Artificial
<220> FEATURE:
<223> OTHER INFORMATION: AON hATXN3Ex7_3

<400> SEQUENCE: 128
aaucaucugc aggaguuggu c                                              21

<210> SEQ ID NO 129
<211> LENGTH: 20
<212> TYPE: DNA
<213> ORGANISM: Artificial
<220> FEATURE:
<223> OTHER INFORMATION: target hATXN3Ex7_4

<400> SEQUENCE: 129
ggtccaacag atgcatcgac                                                20

<210> SEQ ID NO 130
<211> LENGTH: 20
<212> TYPE: RNA
<213> ORGANISM: Artificial
<220> FEATURE:
<223> OTHER INFORMATION: AON hATXN3Ex7_4

<400> SEQUENCE: 130
gucgaugcau cuguuggacc                                                20

<210> SEQ ID NO 131
<211> LENGTH: 20
<212> TYPE: DNA
<213> ORGANISM: Artificial
<220> FEATURE:
<223> OTHER INFORMATION: target hATXN3Ex7_5

<400> SEQUENCE: 131
gcacaactaa aagagcaaag                                                20

<210> SEQ ID NO 132
<211> LENGTH: 20
<212> TYPE: RNA
<213> ORGANISM: Artificial
<220> FEATURE:
<223> OTHER INFORMATION: AON hATXN3Ex7_5

<400> SEQUENCE: 132
cuuugcucuu uuaguugugc                                                20

<210> SEQ ID NO 133
<211> LENGTH: 21
<212> TYPE: DNA
<213> ORGANISM: Artificial
<220> FEATURE:
<223> OTHER INFORMATION: target hATXN3Ex8_1

<400> SEQUENCE: 133
gttagaagca aatgatggct c                                              21

<210> SEQ ID NO 134
<211> LENGTH: 21
<212> TYPE: RNA

<213> ORGANISM: Artificial
<220> FEATURE:
<223> OTHER INFORMATION: AON hATXN3Ex8_1

<400> SEQUENCE: 134
gagccaucau uugcuucuaa c                                              21

<210> SEQ ID NO 135
<211> LENGTH: 20
<212> TYPE: DNA
<213> ORGANISM: Artificial
<220> FEATURE:
<223> OTHER INFORMATION: target hATXN3Ex8_2

<400> SEQUENCE: 135
ctcaggaatg ttagacgaag                                                20

<210> SEQ ID NO 136
<211> LENGTH: 20
<212> TYPE: RNA
<213> ORGANISM: Artificial
<220> FEATURE:
<223> OTHER INFORMATION: AON hATXN3Ex8_2

<400> SEQUENCE: 136
cuucgucuaa cauuccugag                                                20

<210> SEQ ID NO 137
<211> LENGTH: 20
<212> TYPE: DNA
<213> ORGANISM: Artificial
<220> FEATURE:
<223> OTHER INFORMATION: target hATXN3Ex8_3

<400> SEQUENCE: 137
gaggaggatt tgcagagggc                                                20

<210> SEQ ID NO 138
<211> LENGTH: 20
<212> TYPE: RNA
<213> ORGANISM: Artificial
<220> FEATURE:
<223> OTHER INFORMATION: AON hATXN3Ex8_3

<400> SEQUENCE: 138
gcccucugca aauccuccuc                                                20

<210> SEQ ID NO 139
<211> LENGTH: 20
<212> TYPE: DNA
<213> ORGANISM: Artificial
<220> FEATURE:
<223> OTHER INFORMATION: target hATXN3Ex8_4

<400> SEQUENCE: 139
gaggaagcag atctccgcag                                                20

<210> SEQ ID NO 140
<211> LENGTH: 20
<212> TYPE: RNA
<213> ORGANISM: Artificial
<220> FEATURE:
<223> OTHER INFORMATION: AON hATXN3Ex8_4

<400> SEQUENCE: 140
cugcggagau cugcuuccuc                                                20

<210> SEQ ID NO 141
<211> LENGTH: 23
<212> TYPE: DNA
<213> ORGANISM: Artificial
<220> FEATURE:
<223> OTHER INFORMATION: target hATXN3Ex8_5

<400> SEQUENCE: 141
ggctattcag ctaagtatgc aag                                          23

<210> SEQ ID NO 142
<211> LENGTH: 23
<212> TYPE: RNA
<213> ORGANISM: Artificial
<220> FEATURE:
<223> OTHER INFORMATION: AON hATXN3Ex8_5

<400> SEQUENCE: 142
cuugcauacu uagcugaaua gcc                                          23

<210> SEQ ID NO 143
<211> LENGTH: 22
<212> TYPE: DNA
<213> ORGANISM: Artificial
<220> FEATURE:
<223> OTHER INFORMATION: target hATXN3Ex9_1

<400> SEQUENCE: 143
ggtagttcca gaaacatatc tc                                           22

<210> SEQ ID NO 144
<211> LENGTH: 22
<212> TYPE: RNA
<213> ORGANISM: Artificial
<220> FEATURE:
<223> OTHER INFORMATION: AON hATXN3Ex9_1

<400> SEQUENCE: 144
gagauauguu ucuggaacua cc                                           22

<210> SEQ ID NO 145
<211> LENGTH: 21
<212> TYPE: DNA
<213> ORGANISM: Artificial
<220> FEATURE:
<223> OTHER INFORMATION: target hATXN3Ex9_2

<400> SEQUENCE: 145
gcttcggaag agacgagaag c                                            21

<210> SEQ ID NO 146
<211> LENGTH: 21
<212> TYPE: RNA
<213> ORGANISM: Artificial
<220> FEATURE:
<223> OTHER INFORMATION: AON hATXN3Ex9_2

<400> SEQUENCE: 146
gcuucucguc ucuuccgaag c                                            21

<210> SEQ ID NO 147
<211> LENGTH: 22
<212> TYPE: DNA
<213> ORGANISM: Artificial
<220> FEATURE:

```
<223> OTHER INFORMATION: target hATXN3Ex10_1

<400> SEQUENCE: 147
cagcagcaaa agcagcaaca gc                                              22

<210> SEQ ID NO 148
<211> LENGTH: 22
<212> TYPE: RNA
<213> ORGANISM: Artificial
<220> FEATURE:
<223> OTHER INFORMATION: AON hATXN3Ex10_1

<400> SEQUENCE: 148
gcuguugcug cuuuugcugc ug                                              22

<210> SEQ ID NO 149
<211> LENGTH: 20
<212> TYPE: DNA
<213> ORGANISM: Artificial
<220> FEATURE:
<223> OTHER INFORMATION: target hATXN3Ex10_2

<400> SEQUENCE: 149
gacctatcag gacagagttc                                                 20

<210> SEQ ID NO 150
<211> LENGTH: 20
<212> TYPE: RNA
<213> ORGANISM: Artificial
<220> FEATURE:
<223> OTHER INFORMATION: AON hATXN3Ex10_2

<400> SEQUENCE: 150
gaacucuguc cugauagguc                                                 20

<210> SEQ ID NO 151
<211> LENGTH: 21
<212> TYPE: DNA
<213> ORGANISM: Artificial
<220> FEATURE:
<223> OTHER INFORMATION: target hATXN7Ex3_1

<400> SEQUENCE: 151
gagcggaaag aatgtcggag c                                               21

<210> SEQ ID NO 152
<211> LENGTH: 21
<212> TYPE: RNA
<213> ORGANISM: Artificial
<220> FEATURE:
<223> OTHER INFORMATION: AON hATXN7Ex3_1

<400> SEQUENCE: 152
gcuccgacau ucuuuccgcu c                                               21

<210> SEQ ID NO 153
<211> LENGTH: 21
<212> TYPE: DNA
<213> ORGANISM: Artificial
<220> FEATURE:
<223> OTHER INFORMATION: target hATXN7Ex3_2

<400> SEQUENCE: 153
agcgggccgc ggatgacgtc a                                               21
```

```
<210> SEQ ID NO 154
<211> LENGTH: 21
<212> TYPE: RNA
<213> ORGANISM: Artificial
<220> FEATURE:
<223> OTHER INFORMATION: AON hATXN7Ex3_2

<400> SEQUENCE: 154
ugacgucauc cgcggcccgc u                                              21

<210> SEQ ID NO 155
<211> LENGTH: 20
<212> TYPE: DNA
<213> ORGANISM: Artificial
<220> FEATURE:
<223> OTHER INFORMATION: target hATXN7Ex3_3

<400> SEQUENCE: 155
agcagccgcc gcctccgcag                                                20

<210> SEQ ID NO 156
<211> LENGTH: 20
<212> TYPE: RNA
<213> ORGANISM: Artificial
<220> FEATURE:
<223> OTHER INFORMATION: AON hATXN7Ex3_3

<400> SEQUENCE: 156
cugcggaggc ggcggcugcu                                                20

<210> SEQ ID NO 157
<211> LENGTH: 19
<212> TYPE: DNA
<213> ORGANISM: Artificial
<220> FEATURE:
<223> OTHER INFORMATION: target hATXN7Ex3_4

<400> SEQUENCE: 157
acacggccgg aggacggcg                                                 19

<210> SEQ ID NO 158
<211> LENGTH: 19
<212> TYPE: RNA
<213> ORGANISM: Artificial
<220> FEATURE:
<223> OTHER INFORMATION: AON hATXN7Ex3_4

<400> SEQUENCE: 158
cgccguccuc cggccgugu                                                 19

<210> SEQ ID NO 159
<211> LENGTH: 21
<212> TYPE: DNA
<213> ORGANISM: Artificial
<220> FEATURE:
<223> OTHER INFORMATION: target hATXN7Ex3_5

<400> SEQUENCE: 159
gcgccgcctc cacctcggcc g                                              21

<210> SEQ ID NO 160
<211> LENGTH: 21
<212> TYPE: RNA
<213> ORGANISM: Artificial
<220> FEATURE:
<223> OTHER INFORMATION: AON hATXN7Ex3_5
```

<400> SEQUENCE: 160
cggccgaggu ggaggcggcg c                                              21

<210> SEQ ID NO 161
<211> LENGTH: 22
<212> TYPE: DNA
<213> ORGANISM: Artificial
<220> FEATURE:
<223> OTHER INFORMATION: target hATXN7Ex3_6

<400> SEQUENCE: 161
acctcggccg ccgcaatggc ga                                             22

<210> SEQ ID NO 162
<211> LENGTH: 22
<212> TYPE: RNA
<213> ORGANISM: Artificial
<220> FEATURE:
<223> OTHER INFORMATION: AON hATXN7Ex3_6

<400> SEQUENCE: 162
ucgccauugc ggcggccgag gu                                             22

<210> SEQ ID NO 163
<211> LENGTH: 22
<212> TYPE: DNA
<213> ORGANISM: Artificial
<220> FEATURE:
<223> OTHER INFORMATION: target hATXN7Ex3_7

<400> SEQUENCE: 163
ggcctctgcc cagtcctgaa gt                                             22

<210> SEQ ID NO 164
<211> LENGTH: 22
<212> TYPE: RNA
<213> ORGANISM: Artificial
<220> FEATURE:
<223> OTHER INFORMATION: AON hATXN7Ex3_7

<400> SEQUENCE: 164
acuucaggac ugggcagagg cc                                             22

<210> SEQ ID NO 165
<211> LENGTH: 23
<212> TYPE: DNA
<213> ORGANISM: Artificial
<220> FEATURE:
<223> OTHER INFORMATION: target hATXN7Ex3_8

<400> SEQUENCE: 165
tgatgctggg acagtcgtgg aat                                            23

<210> SEQ ID NO 166
<211> LENGTH: 23
<212> TYPE: RNA
<213> ORGANISM: Artificial
<220> FEATURE:
<223> OTHER INFORMATION: AON hATXN7Ex3_8

<400> SEQUENCE: 166
auuccacgac ugucccagca uca                                            23

<210> SEQ ID NO 167
<211> LENGTH: 23

<210> SEQ ID NO 167
<211> LENGTH: 23
<212> TYPE: DNA
<213> ORGANISM: Artificial
<220> FEATURE:
<223> OTHER INFORMATION: target hATXN7Ex3_9

<400> SEQUENCE: 167
aggcttccaa acttcctggg aag                                              23

<210> SEQ ID NO 168
<211> LENGTH: 23
<212> TYPE: RNA
<213> ORGANISM: Artificial
<220> FEATURE:
<223> OTHER INFORMATION: AON hATXN7Ex3_9

<400> SEQUENCE: 168
cuucccagga aguuuggaag ccu                                              23

<210> SEQ ID NO 169
<211> LENGTH: 29
<212> TYPE: DNA
<213> ORGANISM: Artificial
<220> FEATURE:
<223> OTHER INFORMATION: target hHTTEx12_1

<400> SEQUENCE: 169
catcagcgac agctcccaga ccaccaccg                                        29

<210> SEQ ID NO 170
<211> LENGTH: 29
<212> TYPE: RNA
<213> ORGANISM: Artificial
<220> FEATURE:
<223> OTHER INFORMATION: AON hHTTEx12_1

<400> SEQUENCE: 170
cggugguggu cugggagcug ucgcugaug                                        29

<210> SEQ ID NO 171
<211> LENGTH: 20
<212> TYPE: DNA
<213> ORGANISM: Artificial
<220> FEATURE:
<223> OTHER INFORMATION: target hHTTEx12_2

<400> SEQUENCE: 171
tcacagcaca cactgcaggc                                                  20

<210> SEQ ID NO 172
<211> LENGTH: 20
<212> TYPE: RNA
<213> ORGANISM: Artificial
<220> FEATURE:
<223> OTHER INFORMATION: AON hHTTEx12_2

<400> SEQUENCE: 172
gccugcagug ugugcuguga                                                  20

<210> SEQ ID NO 173
<211> LENGTH: 22
<212> TYPE: DNA
<213> ORGANISM: Artificial
<220> FEATURE:
<223> OTHER INFORMATION: target hHTTEx12_3

<400> SEQUENCE: 173

```
ggtcagcagg tcatgacatc at                                              22

<210> SEQ ID NO 174
<211> LENGTH: 22
<212> TYPE: RNA
<213> ORGANISM: Artificial
<220> FEATURE:
<223> OTHER INFORMATION: AON hHTTEx12_3

<400> SEQUENCE: 174
augaugucau gaccugcuga cc                                              22

<210> SEQ ID NO 175
<211> LENGTH: 20
<212> TYPE: DNA
<213> ORGANISM: Artificial
<220> FEATURE:
<223> OTHER INFORMATION: target hHTTEx12_4

<400> SEQUENCE: 175
agagctggct gcttcttcag                                                 20

<210> SEQ ID NO 176
<211> LENGTH: 20
<212> TYPE: RNA
<213> ORGANISM: Artificial
<220> FEATURE:
<223> OTHER INFORMATION: AON hHTTEx12_4

<400> SEQUENCE: 176
cugaagaagc agccagcucu                                                 20

<210> SEQ ID NO 177
<211> LENGTH: 20
<212> TYPE: DNA
<213> ORGANISM: Artificial
<220> FEATURE:
<223> OTHER INFORMATION: target hHTTEx12_5

<400> SEQUENCE: 177
gatgaggagg atatcttgag                                                 20

<210> SEQ ID NO 178
<211> LENGTH: 20
<212> TYPE: RNA
<213> ORGANISM: Artificial
<220> FEATURE:
<223> OTHER INFORMATION: AON hHTTEx12_5

<400> SEQUENCE: 178
cucaagauau ccuccucauc                                                 20

<210> SEQ ID NO 179
<211> LENGTH: 23
<212> TYPE: DNA
<213> ORGANISM: Artificial
<220> FEATURE:
<223> OTHER INFORMATION: target hHTTEx12_6

<400> SEQUENCE: 179
tcagtgaagg atgagatcag tgg                                             23

<210> SEQ ID NO 180
<211> LENGTH: 23
<212> TYPE: RNA
<213> ORGANISM: Artificial
```

```
<220> FEATURE:
<223> OTHER INFORMATION: AON hHTTEx12_6

<400> SEQUENCE: 180
ccacugaucu cauccuucac uga                                               23

<210> SEQ ID NO 181
<211> LENGTH: 20
<212> TYPE: DNA
<213> ORGANISM: Artificial
<220> FEATURE:
<223> OTHER INFORMATION: target hHTTEx12_7

<400> SEQUENCE: 181
atggacctga atgatgggac                                                   20

<210> SEQ ID NO 182
<211> LENGTH: 20
<212> TYPE: RNA
<213> ORGANISM: Artificial
<220> FEATURE:
<223> OTHER INFORMATION: AON hHTTEx12_7

<400> SEQUENCE: 182
gucccaucau ucagguccau                                                   20

<210> SEQ ID NO 183
<211> LENGTH: 20
<212> TYPE: DNA
<213> ORGANISM: Artificial
<220> FEATURE:
<223> OTHER INFORMATION: target hHTTEx12_8

<400> SEQUENCE: 183
tgacaagctc tgccactgat                                                   20

<210> SEQ ID NO 184
<211> LENGTH: 20
<212> TYPE: RNA
<213> ORGANISM: Artificial
<220> FEATURE:
<223> OTHER INFORMATION: AON hHTTEx12_8

<400> SEQUENCE: 184
aucaguggca gagcuuguca                                                   20

<210> SEQ ID NO 185
<211> LENGTH: 20
<212> TYPE: DNA
<213> ORGANISM: Artificial
<220> FEATURE:
<223> OTHER INFORMATION: target hHTTEx12_9

<400> SEQUENCE: 185
tccagccagg tcagcgccgt                                                   20

<210> SEQ ID NO 186
<211> LENGTH: 20
<212> TYPE: RNA
<213> ORGANISM: Artificial
<220> FEATURE:
<223> OTHER INFORMATION: AON hHTTEx12_9

<400> SEQUENCE: 186
acggcgcuga ccuggcugga                                                   20
```

```
<210> SEQ ID NO 187
<211> LENGTH: 21
<212> TYPE: DNA
<213> ORGANISM: Artificial
<220> FEATURE:
<223> OTHER INFORMATION: target hHTTEx12_10

<400> SEQUENCE: 187
actcagtgga tctggccagc t                                              21

<210> SEQ ID NO 188
<211> LENGTH: 21
<212> TYPE: RNA
<213> ORGANISM: Artificial
<220> FEATURE:
<223> OTHER INFORMATION: AON hHTTEx12_10

<400> SEQUENCE: 188
agcuggccag auccacugag u                                              21

<210> SEQ ID NO 189
<211> LENGTH: 18
<212> TYPE: DNA
<213> ORGANISM: Artificial
<220> FEATURE:
<223> OTHER INFORMATION: target hHTTEx13_1

<400> SEQUENCE: 189
cctgcagatt ggacagcc                                                  18

<210> SEQ ID NO 190
<211> LENGTH: 18
<212> TYPE: RNA
<213> ORGANISM: Artificial
<220> FEATURE:
<223> OTHER INFORMATION: AON hHTTEx13_1

<400> SEQUENCE: 190
ggcuguccaa ucugcagg                                                  18

<210> SEQ ID NO 191
<211> LENGTH: 20
<212> TYPE: DNA
<213> ORGANISM: Artificial
<220> FEATURE:
<223> OTHER INFORMATION: target hHTTEx13_2

<400> SEQUENCE: 191
ggtaccgaca accagtattt                                                20

<210> SEQ ID NO 192
<211> LENGTH: 20
<212> TYPE: RNA
<213> ORGANISM: Artificial
<220> FEATURE:
<223> OTHER INFORMATION: AON hHTTEx13_2

<400> SEQUENCE: 192
aaauacuggu ugucgguacc                                                20

<210> SEQ ID NO 193
<211> LENGTH: 21
<212> TYPE: DNA
<213> ORGANISM: Artificial
<220> FEATURE:
<223> OTHER INFORMATION: target hHTTEx14_1
```

```
<400> SEQUENCE: 193
aacatgagtc actgcaggca g                                         21

<210> SEQ ID NO 194
<211> LENGTH: 21
<212> TYPE: RNA
<213> ORGANISM: Artificial
<220> FEATURE:
<223> OTHER INFORMATION: AON hHTTEx14_1

<400> SEQUENCE: 194
cugccugcag ugacucaugu u                                         21

<210> SEQ ID NO 195
<211> LENGTH: 22
<212> TYPE: DNA
<213> ORGANISM: Artificial
<220> FEATURE:
<223> OTHER INFORMATION: target hHTTEx14_2

<400> SEQUENCE: 195
gccttctgac agcagtgttg at                                        22

<210> SEQ ID NO 196
<211> LENGTH: 22
<212> TYPE: RNA
<213> ORGANISM: Artificial
<220> FEATURE:
<223> OTHER INFORMATION: AON hHTTEx14_2

<400> SEQUENCE: 196
aucaacacug cugucagaag gc                                        22

<210> SEQ ID NO 197
<211> LENGTH: 20
<212> TYPE: DNA
<213> ORGANISM: Artificial
<220> FEATURE:
<223> OTHER INFORMATION: target hHTTEx14_3

<400> SEQUENCE: 197
gttgagagat gaagctactg                                           20

<210> SEQ ID NO 198
<211> LENGTH: 20
<212> TYPE: RNA
<213> ORGANISM: Artificial
<220> FEATURE:
<223> OTHER INFORMATION: AON hHTTEx14_3

<400> SEQUENCE: 198
caguagcuuc aucucucaac                                           20

<210> SEQ ID NO 199
<211> LENGTH: 22
<212> TYPE: DNA
<213> ORGANISM: Artificial
<220> FEATURE:
<223> OTHER INFORMATION: target hTBPEx3_1:

<400> SEQUENCE: 199
gccatgactc ccggaatccc ta                                        22

<210> SEQ ID NO 200
```

```
<211> LENGTH: 22
<212> TYPE: RNA
<213> ORGANISM: Artificial
<220> FEATURE:
<223> OTHER INFORMATION: AON hTBPEx3_1:

<400> SEQUENCE: 200
uagggauucc gggagucaug gc                                              22

<210> SEQ ID NO 201
<211> LENGTH: 22
<212> TYPE: DNA
<213> ORGANISM: Artificial
<220> FEATURE:
<223> OTHER INFORMATION: target hTBPEx3_2:

<400> SEQUENCE: 201
cctatcttta gtccaatgat gc                                              22

<210> SEQ ID NO 202
<211> LENGTH: 22
<212> TYPE: RNA
<213> ORGANISM: Artificial
<220> FEATURE:
<223> OTHER INFORMATION: AON hTBPEx3_2:

<400> SEQUENCE: 202
gcaucauugg acuaaagaua gg                                              22

<210> SEQ ID NO 203
<211> LENGTH: 22
<212> TYPE: DNA
<213> ORGANISM: Artificial
<220> FEATURE:
<223> OTHER INFORMATION: target hTBPEx3_3:

<400> SEQUENCE: 203
tatggcactg gactgacccc ac                                              22

<210> SEQ ID NO 204
<211> LENGTH: 22
<212> TYPE: RNA
<213> ORGANISM: Artificial
<220> FEATURE:
<223> OTHER INFORMATION: AON hTBPEx3_3:

<400> SEQUENCE: 204
guggggucag uccagugcca ua                                              22

<210> SEQ ID NO 205
<211> LENGTH: 21
<212> TYPE: DNA
<213> ORGANISM: Artificial
<220> FEATURE:
<223> OTHER INFORMATION: target hTBPEx3_4:

<400> SEQUENCE: 205
gcagctgcag ccgttcagca g                                               21

<210> SEQ ID NO 206
<211> LENGTH: 21
<212> TYPE: RNA
<213> ORGANISM: Artificial
<220> FEATURE:
<223> OTHER INFORMATION: AON hTBPEx3_4:

<400> SEQUENCE: 206
```

-continued

```
cugcugaacg gcugcagcug c                                         21

<210> SEQ ID NO 207
<211> LENGTH: 22
<212> TYPE: DNA
<213> ORGANISM: Artificial
<220> FEATURE:
<223> OTHER INFORMATION: target hTBPEx3_5:

<400> SEQUENCE: 207
gttcagcagt caacgtccca gc                                        22

<210> SEQ ID NO 208
<211> LENGTH: 22
<212> TYPE: RNA
<213> ORGANISM: Artificial
<220> FEATURE:
<223> OTHER INFORMATION: AON hTBPEx3_5:

<400> SEQUENCE: 208
gcugggacgu ugacugcuga ac                                        22

<210> SEQ ID NO 209
<211> LENGTH: 22
<212> TYPE: DNA
<213> ORGANISM: Artificial
<220> FEATURE:
<223> OTHER INFORMATION: target hTBPEx3_6:

<400> SEQUENCE: 209
aacctcaggc caggcaccac ag                                        22

<210> SEQ ID NO 210
<211> LENGTH: 22
<212> TYPE: RNA
<213> ORGANISM: Artificial
<220> FEATURE:
<223> OTHER INFORMATION: AON hTBPEx3_6:

<400> SEQUENCE: 210 cugguggugcc uggccugagg uu                                       22

<210> SEQ ID NO 211
<211> LENGTH: 21
<212> TYPE: DNA
<213> ORGANISM: Artificial
<220> FEATURE:
<223> OTHER INFORMATION: target hTBPEx3_7:

<400> SEQUENCE: 211
gcaccacagc tcttccactc a                                         21

<210> SEQ ID NO 212
<211> LENGTH: 21
<212> TYPE: RNA
<213> ORGANISM: Artificial
<220> FEATURE:
<223> OTHER INFORMATION: AON hTBPEx3_7:

<400> SEQUENCE: 212
ugaguggaag agcugguggug c                                        21

<210> SEQ ID NO 213
<211> LENGTH: 21
<212> TYPE: DNA
```

```
<213> ORGANISM: Artificial
<220> FEATURE:
<223> OTHER INFORMATION: target hTBPEx3_8:

<400> SEQUENCE: 213
ctcacagact ctcacaactg c                                              21

<210> SEQ ID NO 214
<211> LENGTH: 21
<212> TYPE: RNA
<213> ORGANISM: Artificial
<220> FEATURE:
<223> OTHER INFORMATION: AON hTBPEx3_8:

<400> SEQUENCE: 214
gcaguuguga gagucuguga g                                              21

<210> SEQ ID NO 215
<211> LENGTH: 22
<212> TYPE: DNA
<213> ORGANISM: Artificial
<220> FEATURE:
<223> OTHER INFORMATION: target hTBPEx3_9:

<400> SEQUENCE: 215
ggcaccactc cactgtatcc ct                                             22

<210> SEQ ID NO 216
<211> LENGTH: 22
<212> TYPE: RNA
<213> ORGANISM: Artificial
<220> FEATURE:
<223> OTHER INFORMATION: AON hTBPEx3_9:

<400> SEQUENCE: 216
agggauacag uggaguggug cc                                             22

<210> SEQ ID NO 217
<211> LENGTH: 22
<212> TYPE: DNA
<213> ORGANISM: Artificial
<220> FEATURE:
<223> OTHER INFORMATION: target hTBPEx3_10:

<400> SEQUENCE: 217
catcactcct gccacgccag ct                                             22

<210> SEQ ID NO 218
<211> LENGTH: 22
<212> TYPE: RNA
<213> ORGANISM: Artificial
<220> FEATURE:
<223> OTHER INFORMATION: AON hTBPEx3_10:

<400> SEQUENCE: 218
agcuggcgug gcaggaguga ug                                             22

<210> SEQ ID NO 219
<211> LENGTH: 22
<212> TYPE: DNA
<213> ORGANISM: Artificial
<220> FEATURE:
<223> OTHER INFORMATION: target hTBPEx3_11:

<400> SEQUENCE: 219
agagttctgg gattgtaccg ca                                             22
```

```
<210> SEQ ID NO 220
<211> LENGTH: 22
<212> TYPE: RNA
<213> ORGANISM: Artificial
<220> FEATURE:
<223> OTHER INFORMATION: AON hTBPEx3_11:

<400> SEQUENCE: 220
ugcgguacaa ucccagaacu cu                                              22

<210> SEQ ID NO 221
<211> LENGTH: 22
<212> TYPE: DNA
<213> ORGANISM: Artificial
<220> FEATURE:
<223> OTHER INFORMATION: target hTBPEx4_1:

<400> SEQUENCE: 221
tgtatccaca gtgaatcttg gt                                              22

<210> SEQ ID NO 222
<211> LENGTH: 22
<212> TYPE: RNA
<213> ORGANISM: Artificial
<220> FEATURE:
<223> OTHER INFORMATION: AON hTBPEx4_1:

<400> SEQUENCE: 222
accaagauuc acuggaua ca                                                22

<210> SEQ ID NO 223
<211> LENGTH: 21
<212> TYPE: DNA
<213> ORGANISM: Artificial
<220> FEATURE:
<223> OTHER INFORMATION: target hTBPEx4_2:

<400> SEQUENCE: 223
ggttgtaaac ttgacctaaa g                                               21

<210> SEQ ID NO 224
<211> LENGTH: 21
<212> TYPE: RNA
<213> ORGANISM: Artificial
<220> FEATURE:
<223> OTHER INFORMATION: AON hTBPEx4_2:

<400> SEQUENCE: 224
cuuuagguca aguuuacaac c                                               21

<210> SEQ ID NO 225
<211> LENGTH: 23
<212> TYPE: DNA
<213> ORGANISM: Artificial
<220> FEATURE:
<223> OTHER INFORMATION: target hTBPEx4_3:

<400> SEQUENCE: 225
cattgcactt cgtgcccgaa acg                                             23

<210> SEQ ID NO 226
<211> LENGTH: 23
<212> TYPE: RNA
<213> ORGANISM: Artificial
<220> FEATURE:
```

<223> OTHER INFORMATION: AON hTBPEx4_3:

<400> SEQUENCE: 226
cguuucgggc acgaagugca aug        23

<210> SEQ ID NO 227
<211> LENGTH: 240
<212> TYPE: PRT
<213> ORGANISM: Homo sapiens

<400> SEQUENCE: 227

Ser Ile Val Glu Leu Ile Ala Gly Gly Ser Ser Cys Ser Pro Val
1               5                   10                  15

Leu Ser Arg Lys Gln Lys Gly Lys Val Leu Leu Gly Glu Glu Ala
            20                  25                  30

Leu Glu Asp Asp Ser Glu Ser Arg Ser Asp Val Ser Ser Ala Leu
        35                  40                  45

Thr Ala Ser Val Lys Asp Glu Ile Ser Gly Glu Leu Ala Ala Ser
    50                  55                  60

Gly Val Ser Thr Pro Gly Ser Ala Gly His Asp Ile Ile Thr Glu Gln
65                  70                  75                  80

Pro Arg Ser Gln His Thr Leu Gln Ala Asp Ser Val Asp Leu Ala Ser
                85                  90                  95

Cys Asp Leu Thr Ser Ser Ala Thr Asp Gly Asp Glu Glu Asp Ile Leu
                100                 105                 110

Ser His Ser Ser Ser Gln Val Ser Ala Val Pro Ser Asp Pro Ala Met
                115                 120                 125

Asp Leu Asn Asp Gly Thr Gln Ala Ser Ser Pro Ile Ser Asp Ser Ser
130                 135                 140

Gln Thr Thr Thr Glu Gly Pro Asp Ser Ala Val Thr Pro Ser Asp Ser
145                 150                 155                 160

Ser Glu Ile Val Leu Asp Gly Thr Asp Asn Gln Tyr Leu Gly Leu Gln
                165                 170                 175

Ile Gly Gln Pro Gln Asp Glu Asp Glu Ala Thr Gly Ile Leu Pro
                180                 185                 190

Asp Glu Ala Ser Glu Ala Phe Arg Asn Ser Ser Met Ala Leu Gln Gln
                195                 200                 205

Ala His Leu Leu Lys Asn Met Ser His Cys Arg Gln Pro Ser Asp Ser
            210                 215                 220

Ser Val Asp Lys Phe Val Leu Arg Asp Glu Ala Thr Glu Pro Gly Asp
225                 230                 235                 240

<210> SEQ ID NO 228
<211> LENGTH: 16
<212> TYPE: DNA
<213> ORGANISM: Homo sapiens

<400> SEQUENCE: 228
cagccaggtc agcgcc        16

<210> SEQ ID NO 229
<211> LENGTH: 16
<212> TYPE: DNA
<213> ORGANISM: Artificial
<220> FEATURE:
<223> OTHER INFORMATION: skipped PCR product of HDEx12_1

<400> SEQUENCE: 229

```
cagccagGTG ttagac                                                            16
```

<210> SEQ ID NO 230
<211> LENGTH: 172
<212> TYPE: PRT
<213> ORGANISM: Homo sapiens
<220> FEATURE:
<221> NAME/KEY: DOMAIN
<222> LOCATION: (49)..(52)
<223> OTHER INFORMATION: caspase cleavage motif
<220> FEATURE:
<221> NAME/KEY: DOMAIN
<222> LOCATION: (88)..(91)
<223> OTHER INFORMATION: caspase cleavage motif
<220> FEATURE:
<221> NAME/KEY: DOMAIN
<222> LOCATION: (122)..(125)
<223> OTHER INFORMATION: caspase cleavage motif

<400> SEQUENCE: 230

Asp Val Ser Ser Ser Ala Leu Thr Ala Ser Val Lys Asp Glu Ile Ser
1               5                   10                  15

Gly Glu Leu Ala Ala Ser Ser Gly Val Ser Thr Pro Gly Ser Ala Gly
            20                  25                  30

His Asp Ile Ile Thr Glu Gln Pro Arg Ser Gln His Thr Leu Gln Ala
        35                  40                  45

Asp Ser Val Asp Leu Ala Ser Cys Asp Leu Thr Ser Ser Ala Thr Asp
    50                  55                  60

Gly Asp Glu Glu Asp Ile Leu Ser His Ser Ser Ser Gln Val Ser Ala
65                  70                  75                  80

Val Pro Ser Asp Pro Ala Met Asp Leu Asn Asp Gly Thr Gln Ala Ser
                85                  90                  95

Ser Pro Ile Ser Asp Ser Ser Gln Thr Thr Thr Glu Gly Pro Asp Ser
            100                 105                 110

Ala Val Thr Pro Ser Asp Ser Ser Glu Ile Val Leu Asp Gly Thr Asp
        115                 120                 125

Asn Gln Tyr Leu Gly Leu Gln Ile Gly Gln Pro Gln Asp Glu Asp Glu
    130                 135                 140

Glu Ala Thr Gly Ile Leu Pro Asp Glu Ala Ser Glu Ala Phe Arg Asn
145                 150                 155                 160

Ser Ser Met Ala Leu Gln Gln Ala His Leu Leu Lys
                165                 170

<210> SEQ ID NO 231
<211> LENGTH: 78
<212> TYPE: DNA
<213> ORGANISM: Homo sapiens
<220> FEATURE:
<221> NAME/KEY: CDS
<222> LOCATION: (1)..(78)

<400> SEQUENCE: 231 tcc agc cag gtc agc gcc gtc cca tct gac cct gcc atg gac ctg aat    48
Ser Ser Gln Val Ser Ala Val Pro Ser Asp Pro Ala Met Asp Leu Asn
1               5                   10                  15 gat ggg acc cag gcc tcg tcg ccc atc agc                            78
Asp Gly Thr Gln Ala Ser Ser Pro Ile Ser
            20                  25

<210> SEQ ID NO 232
<211> LENGTH: 26
<212> TYPE: PRT
<213> ORGANISM: Homo sapiens -continued

<400> SEQUENCE: 232

Ser Ser Gln Val Ser Ala Val Pro Ser Asp Pro Ala Met Asp Leu Asn
1               5                   10                  15

Asp Gly Thr Gln Ala Ser Ser Pro Ile Ser
            20                  25

<210> SEQ ID NO 233
<211> LENGTH: 78
<212> TYPE: DNA
<213> ORGANISM: Homo sapiens
<220> FEATURE:
<221> NAME/KEY: CDS
<222> LOCATION: (1)..(78)

<400> SEQUENCE: 233 gac agc tcc cag acc acc acc gaa ggg cct gat tca gct gtt acc cct        48
Asp Ser Ser Gln Thr Thr Thr Glu Gly Pro Asp Ser Ala Val Thr Pro
1               5                   10                  15 tca gac agt tct gaa att gtg tta gac ggt                                78
Ser Asp Ser Ser Glu Ile Val Leu Asp Gly
            20                  25

<210> SEQ ID NO 234
<211> LENGTH: 26
<212> TYPE: PRT
<213> ORGANISM: Homo sapiens

<400> SEQUENCE: 234

Asp Ser Ser Gln Thr Thr Thr Glu Gly Pro Asp Ser Ala Val Thr Pro
1               5                   10                  15

Ser Asp Ser Ser Glu Ile Val Leu Asp Gly
            20                  25

<210> SEQ ID NO 235
<211> LENGTH: 20
<212> TYPE: RNA
<213> ORGANISM: Artificial Sequence
<220> FEATURE:
<223> OTHER INFORMATION: AON hHTTEx12_7

<400> SEQUENCE: 235
gucccaucau ucagguccau                                                  20

<210> SEQ ID NO 236
<211> LENGTH: 20
<212> TYPE: RNA
<213> ORGANISM: Artificial Sequence
<220> FEATURE:
<223> OTHER INFORMATION: AON hHTTEx12_5

<400> SEQUENCE: 236
cucaagauau ccuccucauc                                                  20

<210> SEQ ID NO 237
<211> LENGTH: 18
<212> TYPE: RNA
<213> ORGANISM: Artificial Sequence
<220> FEATURE:
<223> OTHER INFORMATION: AON hHTTEx13_1

<400> SEQUENCE: 237
ggcuguccaa ucugcagg                                                    18

```
<210> SEQ ID NO 238
<211> LENGTH: 19
<212> TYPE: RNA
<213> ORGANISM: Artificial Sequence
<220> FEATURE:
<223> OTHER INFORMATION: Control AON

<400> SEQUENCE: 238
uccuuucauc ucgggcuc                                                  19

<210> SEQ ID NO 239
<211> LENGTH: 23
<212> TYPE: RNA
<213> ORGANISM: Artificial Sequence
<220> FEATURE:
<223> OTHER INFORMATION: mAON12.1

<400> SEQUENCE: 239
ggcucaagau guccuccuca ucc                                            23

<210> SEQ ID NO 240
<211> LENGTH: 23
<212> TYPE: RNA
<213> ORGANISM: Artificial Sequence
<220> FEATURE:
<223> OTHER INFORMATION: mAON12.2

<400> SEQUENCE: 240
uuucagaacu guccgaagga guc                                            23

<210> SEQ ID NO 241
<211> LENGTH: 18
<212> TYPE: RNA
<213> ORGANISM: Artificial Sequence
<220> FEATURE:
<223> OTHER INFORMATION: mAON13

<400> SEQUENCE: 241
ggcuguccua ucugcaug                                                  18

<210> SEQ ID NO 242
<211> LENGTH: 19
<212> TYPE: RNA
<213> ORGANISM: Artificial Sequence
<220> FEATURE:
<223> OTHER INFORMATION: Scrambled AON

<400> SEQUENCE: 242
cugaacuggu cuacagcuc                                                 19

<210> SEQ ID NO 243
<211> LENGTH: 20
<212> TYPE: RNA
<213> ORGANISM: Artificial Sequence
<220> FEATURE:
<223> OTHER INFORMATION: Alexa488 AON

<400> SEQUENCE: 243
gguacaccua gcggaacaau                                                20

<210> SEQ ID NO 244
<211> LENGTH: 22
<212> TYPE: RNA
<213> ORGANISM: Artificial Sequence
<220> FEATURE:
<223> OTHER INFORMATION: AON9.1 hATXN3Ex9_1
```

```
<400> SEQUENCE: 244
gagauauguu ucuggaacua cc                                          22

<210> SEQ ID NO 245
<211> LENGTH: 21
<212> TYPE: RNA
<213> ORGANISM: Artificial Sequence
<220> FEATURE:
<223> OTHER INFORMATION: AON9.2 hATXN3Ex9_2

<400> SEQUENCE: 245
gcuucucguc ucuuccgaag c                                           21

<210> SEQ ID NO 246
<211> LENGTH: 22
<212> TYPE: RNA
<213> ORGANISM: Artificial Sequence
<220> FEATURE:
<223> OTHER INFORMATION: AON10 hATXN3Ex10_1

<400> SEQUENCE: 246
gcuguugcug cuuuugcugc ug                                          22

<210> SEQ ID NO 247
<211> LENGTH: 21
<212> TYPE: RNA
<213> ORGANISM: Artificial Sequence
<220> FEATURE:
<223> OTHER INFORMATION: mAON9.1

<400> SEQUENCE: 247
gcuucucguc uccuccgcag c                                           21

<210> SEQ ID NO 248
<211> LENGTH: 22
<212> TYPE: RNA
<213> ORGANISM: Artificial Sequence
<220> FEATURE:
<223> OTHER INFORMATION: mAON10

<400> SEQUENCE: 248
gaacuugugg ucggucuuuc ac                                          22

<210> SEQ ID NO 249
<211> LENGTH: 12
<212> TYPE: DNA
<213> ORGANISM: Artificial Sequence
<220> FEATURE:
<223> OTHER INFORMATION: AON 12.1 (exon 12/13)

<400> SEQUENCE: 249
agccaggtgt ta                                                     12

<210> SEQ ID NO 250
<211> LENGTH: 12
<212> TYPE: DNA
<213> ORGANISM: Artificial Sequence
<220> FEATURE:
<223> OTHER INFORMATION: AON 12.1 (exon 11/14)

<400> SEQUENCE: 250
taacagccct tc                                                     12

<210> SEQ ID NO 251
<211> LENGTH: 13
```

```
<212> TYPE: DNA
<213> ORGANISM: Artificial Sequence
<220> FEATURE:
<223> OTHER INFORMATION: AON9.1 + AON 10 (exon 8/11)

<400> SEQUENCE: 251
atgcaagtga tgc                                                    13

<210> SEQ ID NO 252
<211> LENGTH: 14
<212> TYPE: DNA
<213> ORGANISM: Artificial Sequence
<220> FEATURE:
<223> OTHER INFORMATION: AON9.2+AON10 (exon 9/11)

<400> SEQUENCE: 252
acatcaggtg atgc                                                   14

<210> SEQ ID NO 253
<211> LENGTH: 14
<212> TYPE: DNA
<213> ORGANISM: Artificial Sequence
<220> FEATURE:
<223> OTHER INFORMATION: mAON9 + mAON10 (exon 8/11)

<400> SEQUENCE: 253
atgcaaggag gcga                                                   14

<210> SEQ ID NO 254
<211> LENGTH: 115
<212> TYPE: PRT
<213> ORGANISM: Homo sapiens
<220> FEATURE:
<221> NAME/KEY: MISC_FEATURE
<222> LOCATION: (1)..(115)
<223> OTHER INFORMATION: Amyloid Precursor Protein 770 exons 16-18

<400> SEQUENCE: 254

Ser Gly Leu Thr Asn Ile Lys Thr Glu Glu Ile Ser Glu Val Lys Met
1               5                   10                  15

Asp Ala Glu Phe Arg His Asp Ser Gly Tyr Glu Val His His Gln Lys
            20                  25                  30

Leu Val Phe Phe Ala Glu Asp Val Gly Ser Asn Lys Gly Ala Ile Ile
        35                  40                  45

Gly Leu Met Val Gly Gly Val Val Ile Ala Thr Val Ile Val Ile Thr
    50                  55                  60

Leu Val Met Leu Lys Lys Lys Gln Tyr Thr Ser Ile His His Gly Val
65                  70                  75                  80

Val Glu Val Asp Ala Ala Val Thr Pro Glu Glu Arg His Leu Ser Lys
                85                  90                  95

Met Gln Gln Asn Gly Tyr Glu Asn Pro Thr Tyr Lys Phe Phe Glu Gln
            100                 105                 110

Met Gln Asn
        115

<210> SEQ ID NO 255
<211> LENGTH: 114
<212> TYPE: PRT
<213> ORGANISM: Homo sapiens
<220> FEATURE:
<221> NAME/KEY: MISC_FEATURE
<222> LOCATION: (1)..(114)
<223> OTHER INFORMATION: Amyloid Precursor Protein 751 exons 15-17
```

```
<400> SEQUENCE: 255

Gly Leu Thr Asn Ile Lys Thr Glu Glu Ile Ser Glu Val Lys Met Asp
1               5                   10                  15

Ala Glu Phe Arg His Asp Ser Gly Tyr Glu Val His His Gln Lys Leu
            20                  25                  30

Val Phe Phe Ala Glu Asp Val Gly Ser Asn Lys Gly Ala Ile Ile Gly
            35                  40                  45

Leu Met Val Gly Gly Val Val Ile Ala Thr Val Ile Val Ile Thr Leu
        50                  55                  60

Val Met Leu Lys Lys Lys Gln Tyr Thr Ser Ile His His Gly Val Val
65                  70                  75                  80

Glu Val Asp Ala Ala Val Thr Pro Glu Glu Arg His Leu Ser Lys Met
                85                  90                  95

Gln Gln Asn Gly Tyr Glu Asn Pro Thr Tyr Lys Phe Phe Glu Gln Met
                100                 105                 110

Gln Asn

<210> SEQ ID NO 256
<211> LENGTH: 115
<212> TYPE: PRT
<213> ORGANISM: Mus musculus
<220> FEATURE:
<221> NAME/KEY: MISC_FEATURE
<222> LOCATION: (1)..(115)
<223> OTHER INFORMATION: Amyloid Precursor Protein mouse exons 14-16

<400> SEQUENCE: 256

Ser Gly Leu Thr Asn Ile Lys Thr Glu Glu Ile Ser Glu Val Lys Met
1               5                   10                  15

Asp Ala Glu Phe Gly His Asp Ser Gly Phe Glu Val Arg His Gln Lys
            20                  25                  30

Leu Val Phe Phe Ala Glu Asp Val Gly Ser Asn Lys Gly Ala Ile Ile
            35                  40                  45

Gly Leu Met Val Gly Gly Val Val Ile Ala Thr Val Ile Val Ile Thr
        50                  55                  60

Leu Val Met Leu Lys Lys Lys Gln Tyr Thr Ser Ile His His Gly Val
65                  70                  75                  80

Val Glu Val Asp Ala Ala Val Thr Pro Glu Glu Arg His Leu Ser Lys
                85                  90                  95

Met Gln Gln Asn Gly Tyr Glu Asn Pro Thr Tyr Lys Phe Phe Glu Gln
                100                 105                 110

Met Gln Asn
        115
```